(12) United States Patent
Jimenez et al.

(10) Patent No.: US 11,357,569 B2
(45) Date of Patent: Jun. 14, 2022

(54) OPTICAL-GUIDED ABLATION SYSTEM FOR USE WITH PULSED FIELDS OR OTHER ENERGY SOURCES

(71) Applicant: Medlumics S.L., Madrid (ES)

(72) Inventors: Jorge Jimenez, Atlanta, GA (US); David Herranz, Alpedrete (ES); James Greene, Shelfield Green (GB); Michael Nagy, Glen Ellyn, IL (US); Tyler Panian, Naperville, IL (US); Juan Sancho, Tres Cantos (ES); Matthieu Duperron, Madrid (ES)

(73) Assignee: Medlumics S.L., Madrid (ES)

( * ) Notice: Subject to any disclaimer, the term of this patent is extended or adjusted under 35 U.S.C. 154(b) by 0 days.

(21) Appl. No.: 17/148,506

(22) Filed: Jan. 13, 2021

(65) Prior Publication Data
US 2021/0212755 A1    Jul. 15, 2021

(30) Foreign Application Priority Data

Jan. 13, 2020 (EP) .................................... 20382014
Aug. 31, 2020 (EP) .................................... 20382774

(51) Int. Cl.
*A61B 18/14* (2006.01)
*A61B 18/12* (2006.01)
*A61B 18/00* (2006.01)

(52) U.S. Cl.
CPC ...... *A61B 18/1492* (2013.01); *A61B 18/1206* (2013.01); *A61B 2018/00178* (2013.01);
(Continued)

(58) Field of Classification Search
CPC ............ A61B 18/1492; A61B 18/1206; A61B 2018/00577; A61B 2018/00178;
(Continued)

(56) References Cited

U.S. PATENT DOCUMENTS

| 5,947,977 A | 9/1999 | Slepian et al. |
| 6,056,745 A | 5/2000 | Panescu et al. |

(Continued)

FOREIGN PATENT DOCUMENTS

| CA | 3083870 A1 | 6/2019 |
| EP | 2120758 A2 | 11/2009 |

(Continued)

OTHER PUBLICATIONS

Bouchard, Richard, et al. "Photoacoustic characterization of radiofrequency ablation lesions." Photons Plus Ultrasound: Imaging and Sensing 2012. vol. 8223. International Society for Optics and Photonics, 2012. 10 pages.

(Continued)

*Primary Examiner* — Michael F Peffley
*Assistant Examiner* — Bo Ouyang
(74) *Attorney, Agent, or Firm* — Sterne, Kessler, Goldstein & Fox P.L.L.C.

(57) ABSTRACT

Described herein is a system including a catheter, an optical circuit, a pulsed field ablation energy source, and a processing device. The catheter includes a proximal section, a distal section, and a shaft coupled between the proximal section and the distal section. The optical circuit is configured to transport light at least partially from the proximal section to the distal section and back. The pulsed field ablation energy source is coupled to the catheter and configured to transmit pulsed electrical signals to a tissue sample. The processing device is configured to analyze one or more optical signals received from the optical circuit to determine changes in polarization or phase retardation of light reflected or scattered by the tissue sample, and determine changes in a birefringence of the tissue sample based on the changes in polarization or phase retardation.

25 Claims, 24 Drawing Sheets

(52) U.S. Cl.
CPC ............. *A61B 2018/00577* (2013.01); *A61B 2018/00934* (2013.01); *A61B 2018/126* (2013.01); *A61B 2018/1253* (2013.01)

(58) Field of Classification Search
CPC .. A61B 2018/00934; A61B 2018/1253; A61B 2018/126
See application file for complete search history.

(56) References Cited

U.S. PATENT DOCUMENTS

| | | | |
|---|---|---|---|
| 10,779,904 | B2 | 9/2020 | Ransbury et al. |
| 2001/0031942 | A1 | 10/2001 | Tollner et al. |
| 2003/0208252 | A1 | 11/2003 | O'Boyle et al. |
| 2006/0229515 | A1* | 10/2006 | Sharareh ............. A61B 5/0084 600/476 |
| 2007/0270792 | A1 | 11/2007 | Hennemann et al. |
| 2007/0287998 | A1 | 12/2007 | Sharareh et al. |
| 2008/0089641 | A1 | 4/2008 | Feldchtein |
| 2009/0018393 | A1 | 1/2009 | Dick et al. |
| 2009/0306520 | A1 | 12/2009 | Schmitt et al. |
| 2010/0041986 | A1 | 2/2010 | Nguyen et al. |
| 2010/0046953 | A1 | 2/2010 | Shaw et al. |
| 2011/0028967 | A1 | 2/2011 | Rollins et al. |
| 2011/0144524 | A1 | 6/2011 | Fish et al. |
| 2012/0265184 | A1* | 10/2012 | Sliwa ............. A61B 5/0084 606/15 |
| 2014/0052126 | A1* | 2/2014 | Long ............. A61B 18/1492 606/34 |
| 2014/0171936 | A1 | 6/2014 | Govari et al. |
| 2015/0209105 | A1 | 7/2015 | Margallo Balbas et al. |
| 2015/0359593 | A1* | 12/2015 | Fiser ............. A61B 18/245 606/11 |
| 2017/0202619 | A1 | 7/2017 | Lim |
| 2018/0168729 | A1 | 6/2018 | Pratten et al. |
| 2018/0214202 | A1 | 8/2018 | Howard et al. |
| 2021/0045834 | A1 | 2/2021 | Ransbury et al. |

FOREIGN PATENT DOCUMENTS

| | | |
|---|---|---|
| EP | 2208475 A1 | 7/2010 |
| EP | 2736434 A1 | 6/2014 |
| EP | 3141181 A1 | 3/2017 |

OTHER PUBLICATIONS

Iskander-Rizk, Sophinese, et al. "Real-time photoacoustic assessment of radiofrequency ablation lesion formation in the left atrium." Photoacoustics 16 (2019): 100150. 10 pages.

Fleming, Christine, et al., "Optical Coherence Tomography Imaging of Cardiac Radiofrequency Ablation Lesions," Poster presented at Biomedical Optics 2008, St. Petersburg, Florida, Mar. 16-19, 2008; 7 pages.

Fleming, Christine, et al., "Real-Time Imaging of Radiofrequency Cardiac Ablation Using Optical Coherence Tomography," OSA Technical Digest (CD) (Optical Society of America, Mar. 2008), paper BMD88, Mar. 2008; 3 pages.

Boppart, Stephen A., et al., "Real-Time Optical Coherence Tomography for Minimally Invasive Imaging of Prostrate Ablation," Computer Aided Surgery 6:94-103, Accepted Feb. 2001, published online Jan. 2010; 10 pages.

Patel, Nirlep A., et al., "Guidance of Aortic Ablation Using Optical Coherence Tomography," The International Journal of Cardiovascular Imaging 19:171-178, Apr. 2003; 8 pages.

De Boer, Johannes F., et al., "Two-Dimensional Birefringence Imaging in Biological Tissue Using Polarization Sensitive Optical Coherence Tomography," SPIE vol. 3196, 0277, pp. 32-37, Jan. 1998; 6 pages.

Everett, M.J., et al., "Birefringence Characterization of Biological Tissue By Use of Optical Coherence Tomography," Optics Letters, vol. 23, No. 3, Feb. 1, 1998; 3 pages.

Fleming, Christine, "Characterization of Cardiac Tissue Using Optical Coherence Tomography," Department of Biomedical Engineering, Case Western Reserve University, May 2010; 210 pages.

Gonzalez-Suarez, et al., "Relation between denaturation time measured by optical coherence reflectometry and thermal lesion depth during radio frequency cardiac ablation: Feasibility numerical study," Lasers and Surgery in Medicine, 50(3):222-229, Mar. 2018.

Herranz, D., et al., "Novel catheter enabling simultaneous radio frequency ablation and optical coherence reflectometry," Biomedical Optics Express, 6(9):3268-75, Aug. 2015.

Herranz, D., et al., "Percutaneous RF Ablation Guided by Polarization-sensitive Optical Coherence Reflectometry in an Integrated Catheter: Experimental Evaluation of the Procedure," Journal of Innovaations in Cardiac Rhythm Management, 6(8):2086-91, Aug. 2015.

Wittkampf,F., et al., "Electroporation and its Relevance for Cardiac Catheter Ablation," JACC: Clinical Electophysiology, 4(8):977-986, Aug. 2018.

International Search Report and Written Opinion of the International Searching Authority directed to related International Patent Application No. PCT/EP2021/050602, dated Apr. 6, 2021; 20 pages.

International Search Report and Written Opinion of the International Searching Authority directed to related International Patent Application No. PCT/EP2021/050603, dated Apr. 12, 2021; 13 pages.

International Search Report and Written Opinion of the International Searching Authority directed to related International Patent Application No. PCT/EP2021/050604, dated Apr. 30, 2021; 11 pages.

\* cited by examiner

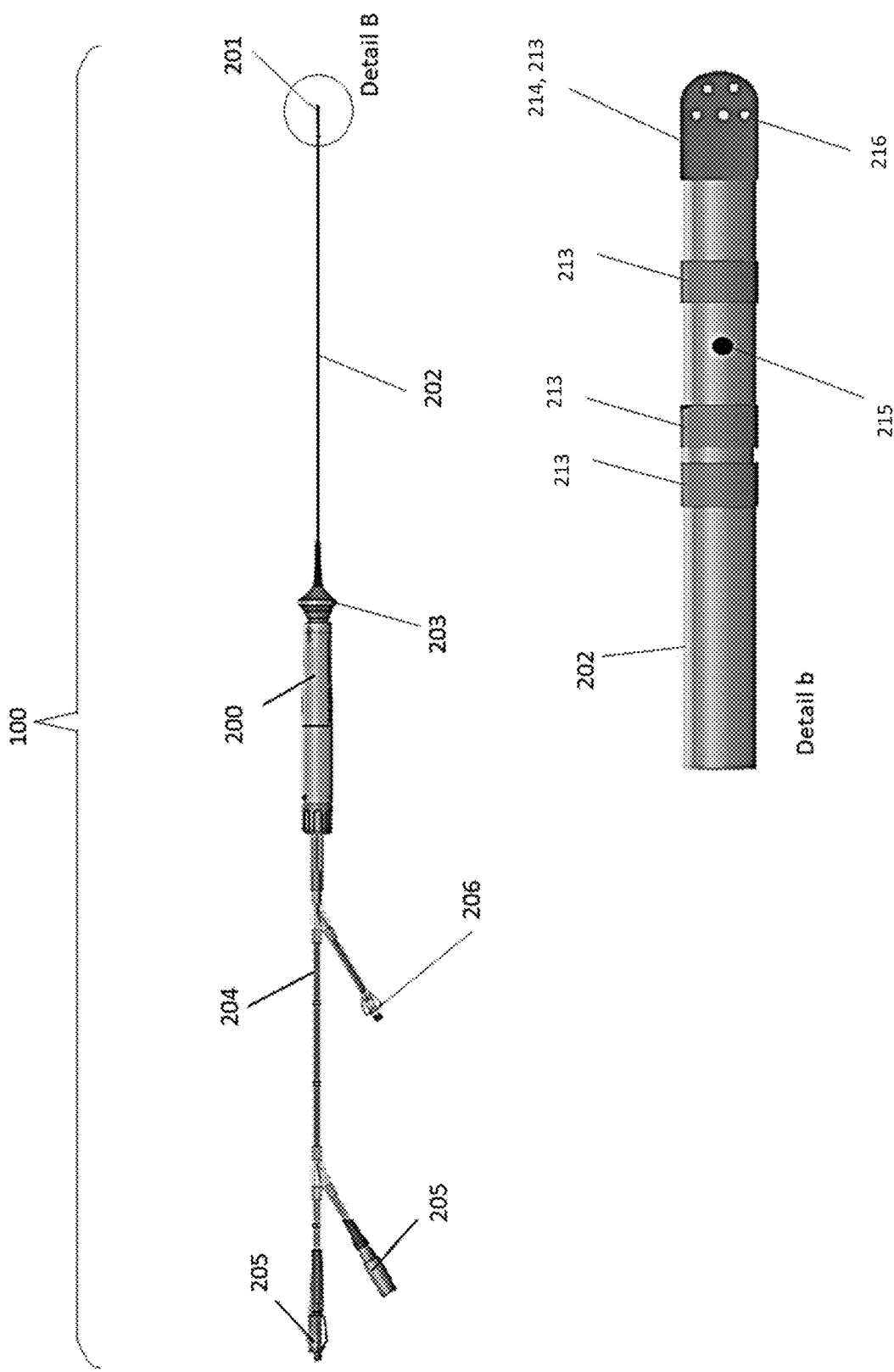

OPTICAL-GUIDED ABLATION SYSTEM FOR USE WITH PULSED FIELDS OR OTHER ENERGY SOURCES

CROSS-REFERENCE TO RELATED APPLICATIONS

This application claims priority to EP App. No. 20382014.7 filed on Jan. 13, 2020 and EP App. No. 20382774.6 filed on Aug. 31, 2020, the disclosures of which are incorporated by reference herein in their entireties.

BACKGROUND

Field

Embodiments of the application relate to catheters, systems, and methods utilizing optical and photonic technology to determine or predict structural changes in tissue associated with ablation-based lesions.

Background

Several medical conditions are treated by ablating healthy tissue to create a lesion in order to affect local tissue or end organ function. Primary examples of such treatments include myocardial ablation for patients with cardiac rhythm abnormalities, renal nerve ablation (e.g., renal-denervation) for patients with hypertension, and neural ablation for treatment of patients with epilepsy. In such procedures, catheters are used to locally deliver the energy needed to ablate the tissue via endovascular access or small incisions. Energy used to create the lesion may include traditional radiofrequency (RF) based heat, cryogenic cooling, and pulsed field ablation.

Atrial fibrillation (AF) is a common type of cardiac arrhythmia with an estimated 33.5 million people worldwide suffering from this condition in 2010. AF increases the risk of stroke by a factor 5 and is a leading healthcare problem in the developed world. Commonly used, available drug therapies to control heart rhythm in AF patients may have significant shortcomings in terms of effectiveness and may cause serious side effects, resulting in reduced quality of life for patients. Cardiac catheter ablation therapy may be a minimally invasive procedure that employs a thin, steerable therapeutic catheter that uses energy to create lesions in cardiac tissue to treat cardiac rhythm abnormalities. Therapy success depends on the clinician's ability to ablate tissue fully through the heart wall and without missing any gaps between ablation points that can be opportunities for AF recurrence. Currently, clinicians cannot determine the quality of catheter contact, contract stability, energy delivered, or quality of ablations performed in real-time. Traditional RF cardiac ablation may also result in significant complications associated with perforations or unintended thermal damage to adjacent structures, as such ablation uses thermal means to create the lesion. To that extent, pulsed field ablation (PFA) uses electromagnetic pulses to generate non-thermal lesions during the ablation process. PFA may use electrodes to cause irreversible electroporation of the cells within it, ultimately leading to cell death. Although this technique reduces complications associated to thermal damage, only a limited or minimal necrosis due to thermal damage might be present in the tissue at the surface of the electrode. Current technologies are limited in showing the clinician if the lesion created by the PFA energy at the selected parameters will result in irreversible electroporation and a subsequent permanent lesion. Lack of such information may lead to significant levels of recurrence of fibrillation. Having the capability to directly assess lesion creation through use of photonics, would enable to clinicians to create safer, more durable and continuous lesions to treat AF and prevent its recurrence.

Epilepsy is the fourth most common neurological disorder and affects people of all ages. Treatment options to date include medication, neurostimulation, surgery, and ablation. Laser ablation using a catheter is one of the most recently used procedures as it is less invasive than surgery, and is able to remove a seizure focus by ablating the area causing the seizures. Limitations in effectiveness and safety for this procedure are associated with the inability of precisely gauging the amount of energy (e.g., heat) delivered into the tissue, as too much energy can damage surrounding neurons and too little energy will necessitate re-ablation. Thus, a catheter that can determine the amount of energy or local temperature at the tissue site would alleviate some of the shortcomings of current technologies.

Several clinical studies have shown that ablation of the renal nerve can reduce blood pressure in hypertensive patients. This procedure and other ablation procedures may be limited by correct delivery of energy to generate a desired lesion geometry. Too little energy results in a lesion that might not penetrate enough into the tissue, leaving transmission gaps and a subsequent need for re-intervention, whereas too much energy may result in complications such as renal artery stenosis or dissection. Therefore, renal denervation would benefit from the use of a photonics-based catheter that could predict lesion geometry based on measurement of real time tissue temperature at the ablated site.

Low coherence interferometry (LCI) is often used in the medical imaging field to provide depth-resolved information of both internal and external tissue. Example LCI techniques include optical coherence reflectometry (OCR) and optical coherence tomography (OCT), which can each provide depth-resolved information with high axial resolution by means of a broadband light source and an interferometric detection system. LCI techniques can be used to determine structural characteristics of tissue and their changes when an ablation lesion occurs. Some of the optical variables that can be used to determine changes in tissue properties are frequency, time of flight, polarization, and intensity.

Spectroscopic techniques based on elastic optical scattering, fluorescence, and Raman scattering are capable of disease diagnosis by characterizing cellular/subcellular structures, cell metabolism states, and molecular signatures of normal and diseased tissues, respectively. Optical spectroscopy techniques have been used to determine the geometry of different anatomical structures within a tissue, and spectroscopy techniques have the benefit of increased penetration depth when compared to some LCI techniques.

As stated above, cardiac ablation, renal denervation, and neural ablation catheter-based interventions suffer from significant limitations associated with the lack of real-time information during a clinical procedure to evaluate lesion progression after energy (e.g., RF, cryogenic, and/or pulsed field) is delivered to the selected site.

BRIEF SUMMARY

Accordingly, there may be a need for providing new catheters, systems, and methods for using optical techniques such as LCI and spectroscopy during and after energy delivery to assess lesion geometry, to improve safety and ensure the accuracy of the ablation in order to reduce the need for re-intervention.

Thus, described herein are embodiments of an optically-guided ablation system that includes a catheter, optical source, an optical circuit, an ablation energy source, and a ablation energy circuit. The ablation system may be used with pulse field ablation energy or RF ablation energy to treat cardiac fibrillation, epilepsy, or conduct renal denervation in various embodiments. Changes in polarization and phase retardation of light used by the optical-based catheter systems described herein may be used to predict thermal lesion geometries during RF ablation or structural changes in tissue and cells associated with cell death in pulsed field ablation procedures.

In an embodiment, an ablation system includes a catheter with optical waveguides or fibers, a data processing device, an optical source, an optical circuit and an ablation energy source. The catheter includes a proximal section, a distal section, and a shaft connecting the proximal section to the distal section. In some embodiments, the proximal section includes a handle as interface with the clinical user. In some embodiments, optical fibers and/or waveguides, as well as electrical wires and/or cables, travel at least partially through the shaft of the catheter in order to transport optical signals and ablation energy to/from a patient's body. In some embodiments, the optical fibers and/or waveguides are part of an optical circuit that allows for the transmission and control of the optical signal emitted by the optical source. In an embodiment, the optical circuit includes optical splitters and or switches to divide the optical signal from the optical source into different paths of the optical circuit in order to send the optical signal to different locations within or on the surface of the patient's body.

In some embodiments, electrical wires are used to transmit ablation energy from the ablation energy source to an ablation site inside or on the surface of the patient's body. In some embodiments, the ablation energy source is a pulsed field ablation (PFA) generator. In some embodiments, the PFA generator sends pulsed electrical signals (monophasic or biphasic) that generate a pulsed RF field to generate a localized lesion in tissue at the ablation site. Electrical signal of the ablation energy source may travel through wires or cables to electrodes located on the surface of the catheter shaft 202. A lesion may be generated by electric field pulses from the electrodes in contact with or penetrated into the tissue at the ablation site. The lesion may be thermal or non-thermal depending on the amount of energy transmitted into the tissue. In some embodiments, the energy source may be modulated to create lesions that are mostly associated with non-thermal damage of the tissue structure. Non-thermal damage occurs when the ablation energy that enters the tissue, causes or increases the size of pores in the membranes of the cells of the tissue to open or increase in size to the extent that cellular edema is caused. Such cellular edema may alter cell function to which the cells may react by initiation of an apoptotic or other delayed cell death process leading to cell death. Alterations to cell wall structure and subsequent cell death through apoptotic, pyroptosis, necroptosis, and/or necrotic processes may change the birefringence characteristics of the ablated tissue as denaturization and/or fragmentation of cellular membrane proteins, cellular cytoskeletons proteins, or proteins in the extracellular matrix alter how the light interacts with such proteins. Thus, optical characteristics, such as polarization, phase retardation, and the like of light that reflects or refracts from such denatured or fragmented structures, leads to changes in tissue birefringence.

In some embodiments, optical signals from the optical source travel through the optical circuit to the ablation site within or on the surface of the patient's body at the same time or after ablation energy is transmitted into the tissue. In some embodiments, light from the optical circuit penetrates the tissue and is reflected, refracted, or scattered back into the optical circuit. The reflected, refracted, or scattered light travels back at least partially through the optical circuit to optical detectors. Optical detectors are used to gather optical data on the characteristics of the returning light, such as intensity, frequency, polarization state, time of flight, phase retardation, and the like. In some embodiments, the optical data and characteristics are analyzed to determine changes in birefringence of the treated tissue associated with the use of pulse field energy for ablation. In some embodiments, data from the returning optical signal, including changes in birefringence of the tissue, may then be sent to a computer or processor unit coupled to the optical detectors. The computer or processor unit may apply interpolation, extrapolation, artificial intelligence (e.g., machine learning), and/or other statistical algorithms to the data from the returning optical signal in order to correlate changes in the received signals to durability and/or geometry of the ablated lesion and to possible re-incidence of cardiac fibrillations or other types of cardiac pacing abnormalities.

In an embodiment, an example system is described. The system includes a catheter, an optical circuit, a pulsed field ablation energy source, and a processing device. The catheter includes a proximal section, a distal section, and a shaft coupled between the proximal section and the distal section. The optical circuit is configured to transport light at least partially from the proximal section to the distal section and back. The pulsed field ablation energy source is coupled to the catheter and configured to transmit pulsed electrical signals to a tissue sample. The processing device is configured to analyze one or more optical signals received from the optical circuit to determine changes in polarization or phase retardation of light reflected or scattered by the tissue sample, and determine changes in a birefringence of the tissue sample based on the changes in polarization and phase retardation.

In another embodiment, an example method for performing ablation in a patient is described. The method includes inserting a catheter into vasculature of the patient, moving a distal end of the catheter to an ablation site in the vasculature of the patient, establishing tissue contact at the distal end of the catheter through optical means using light delivered to the ablation site through the distal end of the catheter, delivering energy from the distal end of the catheter into the tissue from an energy source coupled to the catheter, optically interrogating the ablation tissue site to determine changes in polarization or phase retardation of light delivered to the ablation tissue site through the catheter, and removing the catheter from the vasculature.

In another embodiment, a catheter for ablating tissue in a cardiac wall is described. The catheter includes a proximal end, a distal end, a plurality of electrodes disposed on the distal end at a distance from each other, and at least one optical port positioned on the distal end at a location relative to the plurality of electrodes. The catheter is configured to be placed in an outer sheath such that the distal end is in a straight configuration compatible with vascular delivery, the distal end assuming a circular shape when pushed through the sheath. The plurality of electrodes are connected by wire to an external electrical energy generating device via an electrical connector on the proximal end of the catheter. The plurality of electrodes are configured to deliver electrical energy to the cardiac wall when energized by the external electrical energy generating device, Further features and advantages, as well as the structure and operation of various embodiments, are described in detail below with reference to the accompanying drawings. It is noted that the specific embodiments described herein are not intended to be limiting. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

FIG. 2 illustrates a diagram of example components of a catheter that may be used for controlled ablation, according to embodiments of the present disclosure.

FIGS. 18A and 18B illustrate misalignment and alignment, respectively, of the electrodes and openings in the catheter.

Embodiments of the present disclosure will be described with reference to the accompanying drawings.

DETAILED DESCRIPTION

Although specific configurations and arrangements are discussed, it should be understood that this is done for illustrative purposes only. A person skilled in the pertinent art will recognize that other configurations and arrangements can be used without departing from the spirit and scope of the present disclosure. It will be apparent to a person skilled in the pertinent art that this disclosure can also be employed in a variety of other applications.

It is noted that references in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure or characteristic is described in connection with an embodiment, it would be within the knowledge of one skilled in the art to effect such feature, structure or characteristic in connection with other embodiments whether or not explicitly described.

It should be noted that although this application may refer specifically to cardiac ablation, the embodiments described herein may target other pathologies as well, along with additional energy sources for ablation, including but not limited to cryogenic, radiofrequency (RF), microwave, laser, ultrasound, and pulsed electric fields.

Described herein are embodiments of a medical system, that uses optical signals to characterize changes in tissue during and after ablation energy is delivered to create a lesion in tissue.

In some embodiments, low coherence interferometry (LCI) and/or spectroscopy may be used with optical signals to provide depth-resolved information about the sample tissue being imaged. Although portions of the application may focus on catheters and the transmittance of optical signals through parts of the catheters, it should be understood that the embodiments discussed herein may apply to any medical device that utilizes optical signals.

Exemplary System Embodiments

Figure 1:
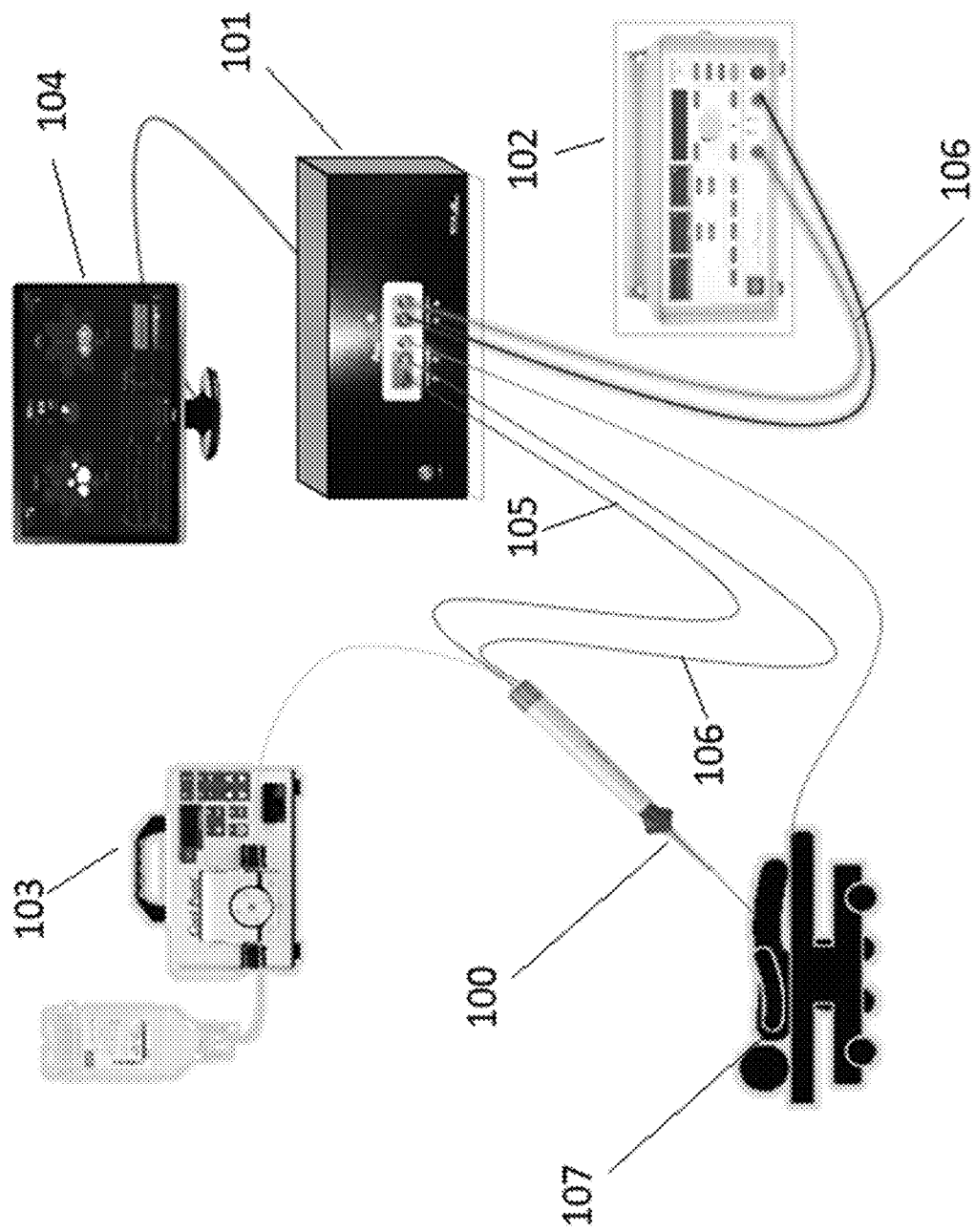
FIG. 1 illustrates a diagram of an example ablation system with optical technology for controlled tissue ablation, according to embodiments of the present disclosure.

FIG. 1 illustrates a diagram of an example ablation system, which includes a catheter 100, a console 101, an ablation energy source 102, a cooling source 103, and a user interface 104. In some embodiments, a distal section of catheter 100 is positioned at a portion of tissue in patient 107. In some embodiments, elements outside the catheter 100 (e.g., referred herein as external elements) may be held in a single enclosure or in multiple enclosures as determined by system design. In some embodiments, elements in different enclosures may be connected through external data cables, optical fibers 105, and/or electrical cabling or wires 106. In some embodiments, the system might not include a cooling source 103. In some embodiments, the ablation system may use traditional radio frequency (RF) ablation means to create thermal lesions in tissue, which may include a cooling source 103 in the form of an irrigation pump to prevent charring of blood. In other embodiments, the ablation system may use pulsed field ablation energy or cryogenic energy, and the cooling source 103 might not be included in the ablation system.

Exemplary Catheter Embodiments

FIG. 2 illustrates catheter 100 according to embodiments of the present disclosure. Catheter 100 includes a proximal section 200, a distal section 201, and a shaft 202 coupled between proximal section 200 and distal section 201. In some embodiments, the proximal section 200 includes a handle to interface with a clinical user. The handle may include one or more buttons, sliders, levers, lights, dials and other elements that allow for mechanical and functional control of the catheter shaft 202 and the distal section 201. In some embodiments, the proximal section 200 of the catheter may also include wiring 204 and one or more connectors 205. The wiring 204 may include a wire harness or grouped cables and optical fibers and/or wave guides. The one or more connectors 205 may serve as an interface for the catheter 100 and connect the catheter 100 directly or indirectly to other elements of the ablation system, including the ablation energy source 102, an optical source, console 101 and/or user interface 104. In some embodiments, the proximal section 200 of the catheter may also have a port to connect to the cooling source 103. In some embodiments, the wiring 204, wiring harness elements, and one or more connectors 205 may be detachable from the handle in the proximal section. In other embodiments, communication between the catheter 100 and other elements of the ablation system may be wireless, using technologies such as Bluetooth, WiFi, cellular, etc.

Proximal section 200 may include further interface elements, with which a user of catheter 100 can control the operation of catheter 100. For example, proximal section 200 may include a deflection control mechanism that controls a deflection angle of distal section 201. The deflection control mechanism may use a mechanical movement of an element on proximal section 200, or the deflection control mechanism may use electrical connections to control the movement of distal section 201. Proximal section 200 may include various buttons or switches that allow a user to control when RF energy is applied at distal section 201, or when beams of radiation and/or light are transmitted from distal section 201, allowing for the acquisition of optical data. In some embodiments, these buttons or switches are located at a separate user interface coupled to a processing device or the handle itself.

The deflection control mechanism may include electrical or mechanical elements designed to provide a signal to distal section 201 in order to change a deflection angle of distal section 201. The deflection system enables guidance of distal section 201 by actuating a mechanical control placed in proximal section 200, according to an embodiment. This deflection system may be based on a series of aligned and uniformly spaced cutouts in catheter shaft 202 aimed at providing unidirectional or multidirectional deflection of distal section 201, in combination with a wire that connects the deflection mechanism control in proximal section 200 with the catheter tip 214 at distal section 201. In this way, a certain movement of the proximal section 200 may be projected to the distal section 201. In some embodiments, the combination of several control wires attached to a catheter tip may enable the deflection of the catheter tip along different directions.

FIG. 2 further illustrates elements of the distal section 201 in an expanded view showing the catheter tip 214. In an embodiment, shaft 202 and distal segments of the catheter may include one or more radiopaque markers 215 for navigation purposes. Distal section 201 may include one or more external electrodes 213 for ablation, according to some embodiments. The electrodes 213 may be distributed over segments of the distal section 201 of the catheter or directly on the catheter tip 214 at the distal end of the distal section 201. In some embodiments, where cooling is needed, the distal section 201 of the catheter 100 may also include one or more irrigation orifices 216. In some embodiments, cooling fluids (e.g., compressible and/or incompressible) provided by the cooling source 103 travel through a channel partially at least through the shaft 202 of the catheter 100 and are then externalized through the irrigation orifices 216. These irrigation orifices 216 can be located in any segments of the catheter shaft 202, electrodes 216, or catheter tip 214.

Figure 3B:
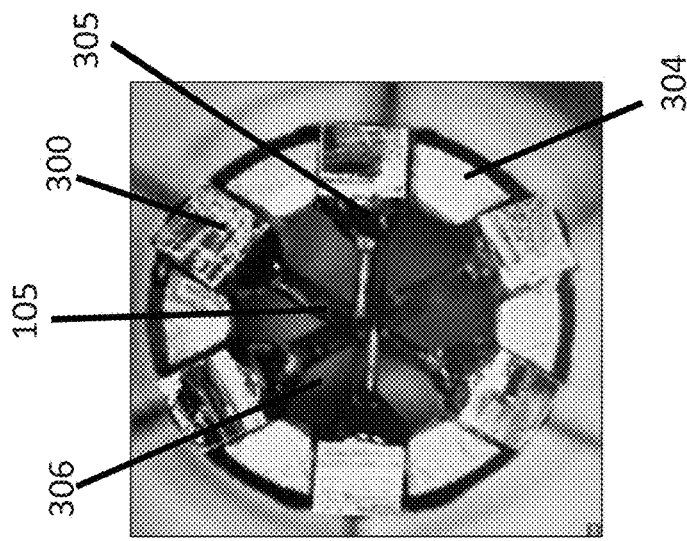
FIG. 3B illustrates a diagram showing an example radial cross-section view of a distal segment of a catheter, according to embodiments of the present disclosure.
Figure 3A:
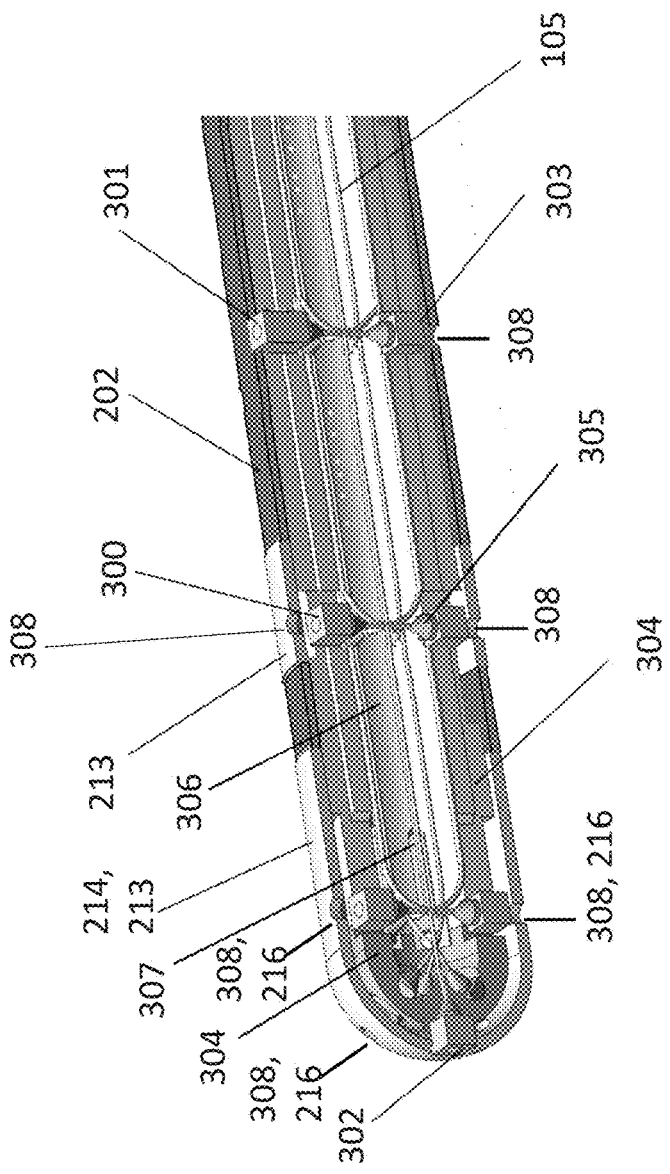
FIG. 3A illustrates a diagram showing an example axial cross-section view of a distal segment of a catheter, according to embodiments of the present disclosure.

FIGS. 3A and 3B illustrate diagrams of an example axial cross-section view and a radial cross section view, respectively, of a distal segment of a catheter, according to embodiments of the present disclosure. FIGS. 3A and 3B illustrate different configurations of electrodes, view ports, and lens-fiber assemblies in the catheter tip.

As shown in FIGS. 3A-3B, the distal section 201 of the catheter and shaft 202 may have a single electrode or multiple electrodes 213 to deliver ablation energy. In some embodiments, PFA energy may be used, and the electrode 213 configuration may be configured to deliver monophasic or biphasic pulse applications. In some embodiments, where cooling is implemented, a central cooling channel 306 and cooling communication paths 307 may guide cooling fluid through the shaft 202 to the distal section 201, and such fluid may then be externalized through irrigation orifices 216 to cool down surrounding tissues or blood.

Distal section 201 may also include a plurality of optical view ports 308 to transmit/collect light at various angles from distal section 201. In some embodiments, the optical view ports 308 may be distributed over the outside of distal section 201, resulting in a plurality of distinct viewing directions, In some embodiments, each of the plurality of viewing directions is substantially non-coplanar.

In some embodiments illustrated in FIGS. 3A-3B light is transported through the shaft 202 and distal section 201 by optical fibers 105. Such optical fibers 105 may be coated or uncoated. In some embodiments, optical fibers 105 are coated with a polymer for protection, insulation and structural integrity. In some embodiments, optical fibers 105 are attached to lenses 300 to focus the light that will then go into the tissue. In some embodiments the fibers may be attached mechanically or chemically through glue or adhesives 305. In some embodiments, the glue or adhesives 305 may be selected to provide mechanical strength and also optical index matching. As illustrated in FIG. 3B, in some embodiments, the lenses 300 and/or fibers 105 may be supported by an internal support structure 304 to localize and orient lenses 300 and fibers 105 in place. In other embodiments, the lenses 300 may be localized and/or oriented by the configuration of the shaft 202, electrodes 213, and the catheter tip 214. In some embodiments, the lenses 300 might not be external elements to the fibers 105, but may be created by curvatures manufactured (e.g., etched, machined, laser cut, or chemically formed) directly onto the distal end of the fiber 105 and the fiber core. In some embodiments, the distal section 201 may include a substrate with patterned waveguides and optical focusing or directing elements (e.g., lenses, mirrors, and the like) for guiding light to/from each of the plurality of optical view ports 308. The substrate may be a flexible or partially flexible substrate made from a material such as polyimide, polyethylene glycol, Parylene, or polydimethelsiloxane (PDMS).

In some embodiments, as shown in FIG. 3A, lenses 300 may be connected to optical fibers and placed within recesses 303 in the catheter. In some embodiments, lenses may be flush 301 with the catheter surface (e.g., shaft, electrodes, or tip), or may extend beyond surface 302 of the catheter shaft 202, electrodes 213, or tip 214. In some embodiments, lenses that are flush 301 with the catheter surface or extend beyond the surface 302 may be a contact point with the external tissue. In some embodiments, where cooling is implemented, lenses that are recessed into the catheter and use view ports 308 to allow for passage of light, may also use these same view ports 308 as irrigation orifices 216. In some embodiments, view ports 308 and irrigation orifices 216 may be distinct and separate elements.

FIGS. 4A-4D illustrate diagrams of example two-dimensional (2D) and three-dimensional (3D) geometries of the distal section 201 of the catheter according to embodiments of the present disclosure. As shown in FIGS. 4A-4D, the distal section 201 of the catheter may take on different 2D and 3D geometries. In some embodiments, the 2D and 3D geometries of the distal section may be the actual geometry of the catheter in its unloaded state. In some embodiments, the catheter geometry may be deflected and/or re-formed to temporarily fit within a delivery sheath for easy passage though vasculature in a patient. In other embodiments, the 2D and 3D geometries of the distal section may be created from a relatively straight catheter distal section through deformation associated to mechanical or electromagnetic forces controlled from the proximal section 200, so that after passage through at least a section of vasculature and prior to ablation energy delivery, the distal section forms such 2D and 3D geometries to improve the surface contact of the catheter with local anatomy.

Figure 4B:
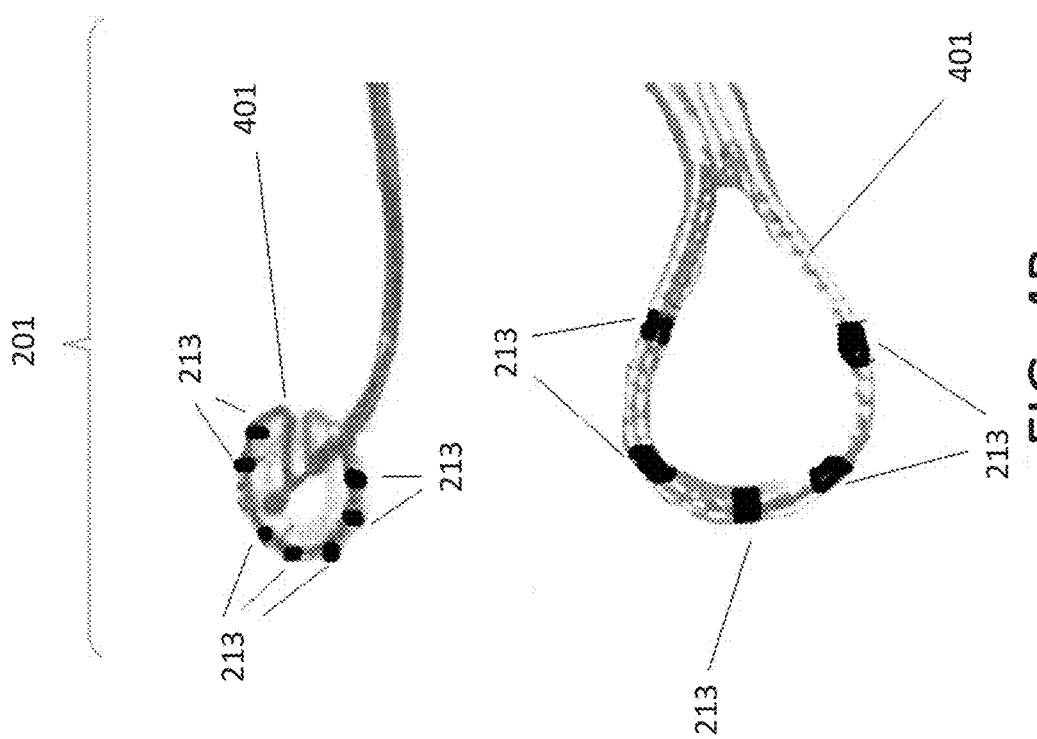
FIGS. 4A-4D illustrate diagrams of example 2D and 3D configurations of the distal segment of the catheter used to accommodate the ablation site geometry, according to embodiments of the present disclosure.
Figure 4A:
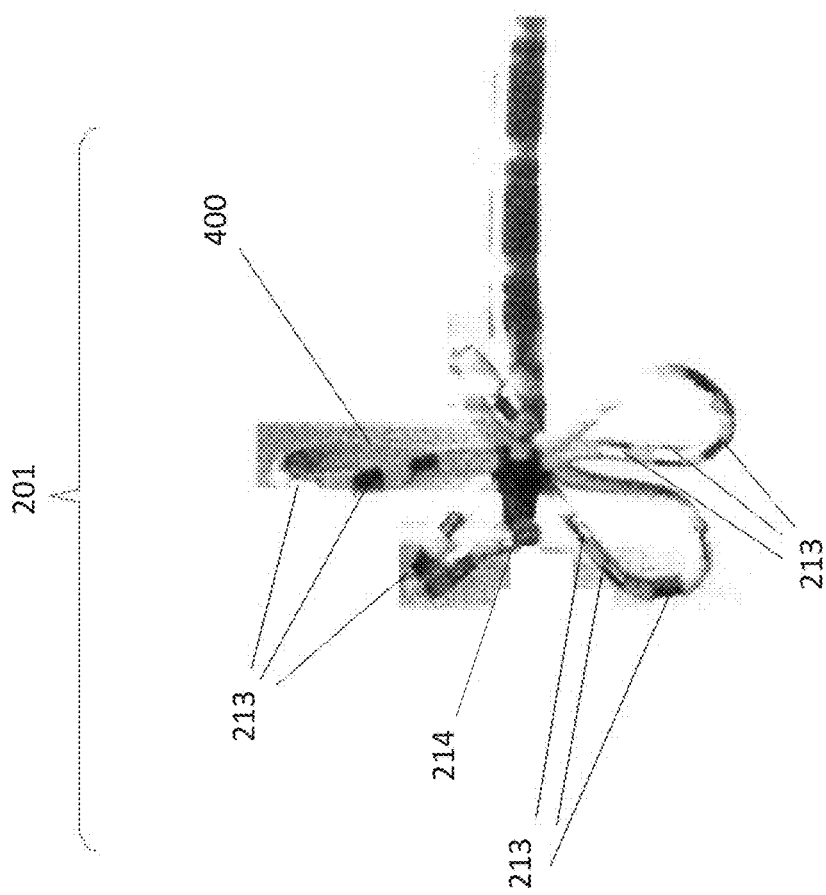
Figure 4D:
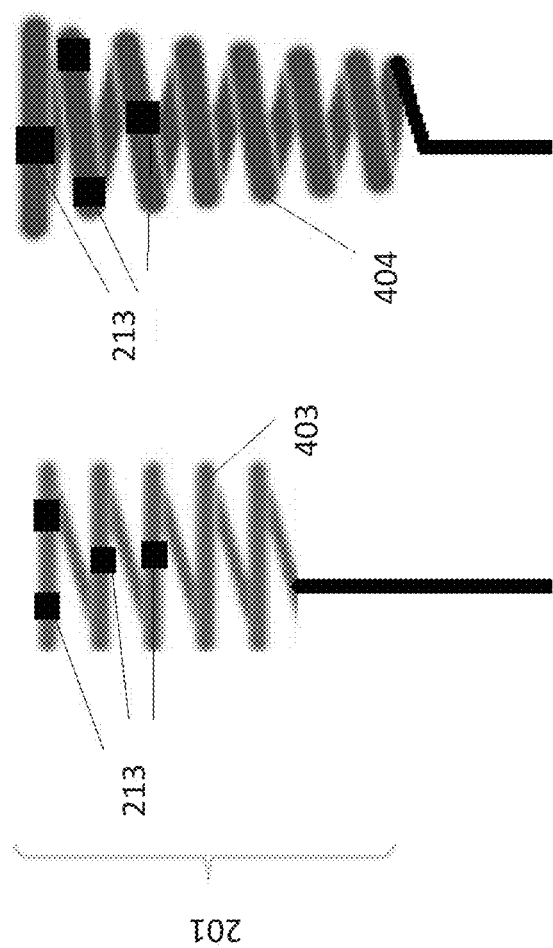
Figure 4C:
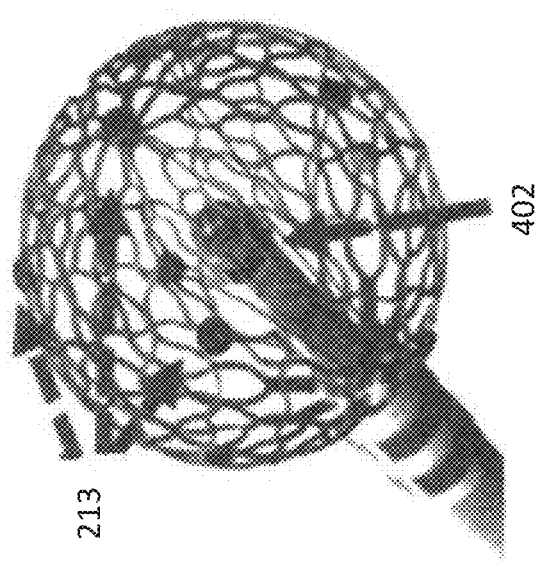

As illustrated in FIGS. 4A-4D, such 2D or 3D geometries may have electrodes 213 placed at different location in the catheter in order to maximize electrode contact and optical access to anatomy (e.g., tissue ablation site) where ablation may be needed. In some embodiments, electrodes 213 and other components of the catheter may have a similar configuration as FIG. 3, with lenses/optical view ports arranged through the shaft 202, distal segment 201, or tip 214. In some geometries, (as shown in FIG. 4B) the distal section 201 of the catheter 201 may at least partially have a loop configuration 401 during ablation. In some embodiments, the geometry with the loop configuration 401 may be beneficial during ablation of a perimeter around arteries and veins in a vasculature. In some embodiments, a radial petals configuration 400 shown in FIG. 4A may extend outwardly for better contact with surrounding tissue. In other embodiments, a 3D sphere configuration 402 (as shown in FIG. 4C), cone, cylinder or other irregular shape configuration may expand from the surface of the distal section 201 to increase its overall diameter for better tissue engagement. In some embodiments, such expanded geometries may be beneficial when ablating tissue of an internal diameter or vasculature or when ablating tissue in defined tissue cavities or chambers inside or on the surface of the human body. In some embodiments, the expanded 3D geometry configuration shown in FIG. 4C may be generated through mechanical deflections by using balloons, rods, wires or other mechanical elements to change the geometry of the distal section 201. In some embodiments, memory materials, such as memory metallic alloys (e.g., Nitinol, etc.) or memory polymers, may be used to generate such geometries/configurations. Other embodiments of the 3D structure of the distal section may include helical structures 403, 404, as shown in FIG. 4D. In some embodiments, the helical structures 403, 404 may be used to ablate the inner lumen of a vasculature or a cavity. In some embodiments, the distal section 201 geometries of a catheter may be implemented during ablation using traditional RF, PFA or cryogenic energy. In some of the exemplary embodiments described above where the distal section 201 changes geometry during the procedure, there may be a mechanism that allow for relative motion of the optical fibers 105 (which tend to be axially rigid) with respect to said distal section 201 or the shaft 202, in order to prevent unwanted tethering or bending of the optical fibers 105 and possible mechanical failure.

In some embodiments, the catheter may include some or all of the following elements interconnecting proximal section 200 with distal section 201, including but not limited to a shaft, an irrigation channel, RF conductive medium, deflection mechanism, electrical connections, and optical transmission media. In some embodiments, electrical connections may be used to provide signals to optical modulating components or to ablating elements located in distal section 201. In some embodiments, one or more optical transmission media may guide light generated from the optical source (e.g., exposure light) towards distal section 201, while another subset of optical transmission media guides light returning from distal section 201 (e.g., scattered or reflected light) back to proximal section 200. In some embodiments, the same one or more optical transmission media guides light in both directions. In some embodiments, optical transmission media includes polarization maintaining (PM) fibers or single mode fibers, multi-mode fibers, or waveguides (single or multi-mode). In some embodiments, the same optical transmission media is used to transport both exposure light and light returning from (scattered or reflected) tissue through at least a section of the length of the catheter, resulting in two-way communication pathways.

In some embodiments, the distal section 201 of the catheter may include other elements, such one or more thermal sensors, pressure sensors, force sensors, electrical sensors, optical splitters, optical mirrors, and multiplexers. In some embodiments, optical interferometer or RF energy source elements may also be contained within the proximal section 200/handle of the catheter. In some embodiments, the energy source 102 and most or all optical interferometry elements may be contained within an external element to the catheter, such as an external ablation energy source 102, console 101, or user interface 104. In some embodiments, console 101, energy source 102, and user interface 104 may be contained within a single enclosure or multiple enclosures.

Exemplary Embodiments of an Ablation Energy Circuit

In some embodiments, an ablation energy circuit may include an ablation energy source 102 and electrical transport elements such as wires and cables, insulating elements, switches, resistors, capacitors, transformers, modulation elements, connectors and electrodes as needed, so that the energy source may deliver electrical energy transported within the catheter through the electrodes into the tissue in order to ablate and create a lesion. In some embodiments, ablation energy is delivered through a pulsed field for PFA systems. In some embodiments, the frequency, amplitude, duration, and other characteristics of the electromagnetic pulses may be selected by the clinician prior to delivering the selected pulsed treatment at the selected ablation site. In some embodiments, PFA may be delivered in a biphasic or monophasic manner. In some embodiments, the PFA energy pulses may be synchronized with cardiac rhythm by sensing the cardiac electrical signals (e.g., QRS complex) using ECG/EKG or other sensing means, and then using the cardiac signal as reference to deliver synchronized PFA energy pulses to a selected ablation site in the heart.

Exemplary Embodiments of an Optical Circuit

Figure 5:
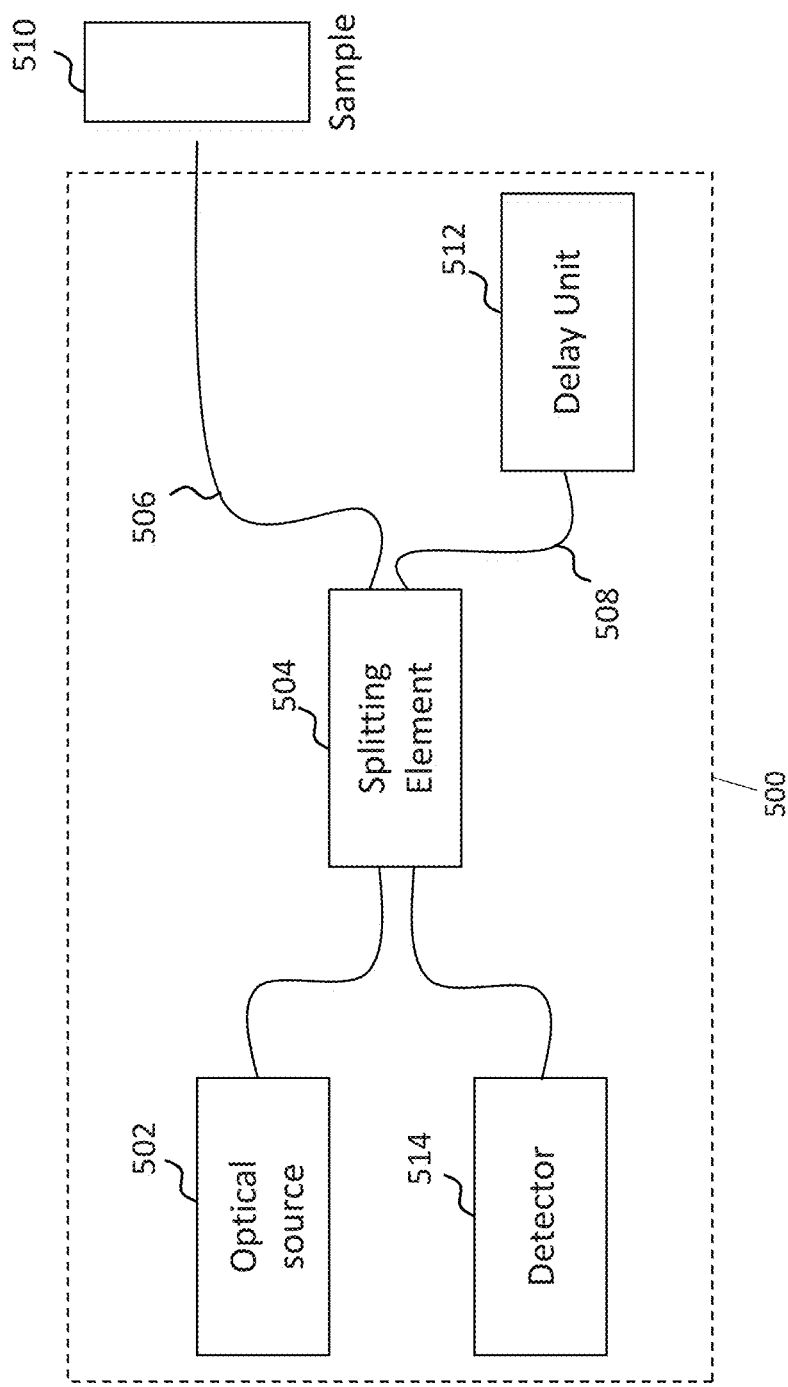
FIG. 5 illustrates a diagram of an example optical circuit, according to embodiments of the present disclosure.

FIG. 5 illustrates a diagram of an example optical circuit 500 according to embodiments of the present disclosure. In some embodiments, elements of the optical circuit 500 illustrated in FIG. 5 are present both within the catheter 100 and as external elements (e.g., external to catheter 100). In some embodiments, external elements of the optical circuit 500 may be housed in multiple or single enclosure. In some embodiments, external elements of the optical circuit 500 are housed within the console 101, which may or may not be housed in the same enclosure as the user interface 104 and ablation energy source 102.

The optical circuit 500 has an optical source 502 that may include one or more laser diodes or light emitting diodes (LEDs). For example, LEDs may be used when performing time domain and/or spectral domain analysis, while tunable lasers may be used to sweep the wavelength of the light across a range of wavelengths. The beam of radiation generated by the optical source 502 may have a wavelength within the infrared range (e.g., 750 nm to 1 mm), while other optical sources 502 may work within the visible range (e.g., 400 nm to 750 nm) or ultraviolet range (e.g, 400 nm to 10 nm). In an example, the beam of radiation has a central wavelength between 1000 nm and 1600 nm. The optical source 502 may be designed to output a beam of radiation at only a single wavelength, or it may be a swept source and be designed to output a range of different wavelengths. The range of wavelengths may include any wavelengths found in the near-infrared or mid-infrared spectral range. The generated beam of radiation may be guided towards distal section 201 via an optical transmission medium connected between proximal section 200 and distal section 201 within shaft 202. Some examples of optical transmission media include single mode and multimode optical fibers and integrated optical waveguides. In some embodiments, the electrical transmission medium and the optical transmission medium are provided by the same hybrid medium allowing for both electrical and optical signal propagation.

In some embodiments, the optical circuit 500 includes one or more components of an interferometer in order to perform LCI using the light generated from the optical source. In some embodiments, in performing LCI, the optical circuit 500 may analyze interferometric data. The interferometric data analysis may be associated with understanding changes in the polarization state of light reflected or scattered by the tissue, which may allow assessment of changes in the birefringence of tissue. In some embodiments, the optical transmission medium used for guiding the light to and from distal section 201 might not affect the state and degree of light polarization (e.g., single mode optical fiber). In other embodiments, for such a LCI circuit, the optical transmission medium may affect the polarization in a constant and reversible way. In further embodiments of the optical circuit 500, optical analysis of the light reflected or scattered back by the tissue may include methods associated with tissue spectroscopy. With tissue spectroscopy, the optical transmission medium used for guiding the light to and from distal section 201 may allow for multiple modes of light, such as a multi-mode optical fiber. In further embodiments of the optical circuit 500, both single mode fibers and multi-mode fibers may be used to determine different paths from one or more optical sources to the distal section 201 and back, so that both LCI methods and spectroscopy methods may be used by the system to better control the ablation procedure.

Various embodiments of the present application include a LCI system integrated within a medical device such as catheter 100 for optical interrogation of a sample 510 (e.g., at an ablation tissue site). In some embodiments, the LCI system may be implemented by optical circuit 500, and the optical circuit 500 may be referred to herein as an LCI system. The optical circuit 500 may include a delay unit 512 which may include various light modulating elements. These modulating elements may perform phase and/or frequency modulation to counteract undesired optical effects in the light, and to select one or more depths of sample to be imaged. The use of the term "light" may refer to any range of the electromagnetic spectrum. In an embodiment, the term "light" refers to infrared radiation.

The optical circuit further includes a splitting element 504, a sample arm 506, a reference arm 508, and a detector 514. In the embodiment shown, delay unit 512 is located within reference arm 508. However, it should be understood that delay unit 512 may instead be located in sample arm 506. Alternatively, various elements of delay unit 512 may be present in both sample arm 506 and reference arm 508. For example, elements of delay unit 512 that introduce a variable delay to the light may be located in sample arm 506, while elements that modulate different polarization modes of the light may be located in reference arm 508. In another example, elements of delay unit 512 that modulate different polarization modes of the light may be located in sample arm 506, while elements that introduce a variable delay to the light may be located in reference arm 508. In one example, sample arm 506 and reference arm 508 are optical waveguides, such as patterned waveguides or optical fibers. In an embodiment, all of the components of LCI system are integrated onto a planar lightwave circuit (PLC). In another embodiment, at least the components within delay unit 512 are integrated on the same substrate of a PLC. Other implementations may be considered as well, such as, for example, fiber optic systems, free-space optical systems, photonic crystal systems, etc.

It should be understood that the LCI system may include any number of other optical elements not shown for the sake of clarity. For example, LCI system may include mirrors, lenses, gratings, splitters, micromechanical elements, etc., along the paths of sample arm 506 or reference arm 508.

Splitting element 504 is used to direct light received from optical source 502 to both sample arm 506 and reference arm 508. Splitting element 304 may be, for example, a bi-directional coupler, an optical splitter, an adjustable splitting-ratio coupler, an optical switch, or any other modulating optical device that converts a single beam of light into two or more beams of light. In some embodiments, the splitting element 504 splits the light into one or more reference arms and multiple sample arms, such the light/radiation from the multiple sample arms can optically interrogate the sample at different locations or directions at the distal section 201. In some embodiments, an initial splitter element directs light into the reference arm 508 and the sample arm 506, and a second splitter element may further split the sample arm 506 into multiple beams. It is understood that any combination of one or multiple numbers of splitter elements 504 in different parts of the radiation/light path may be used to create multiple beams for reference and to interrogate the sample as needed by the optical analysis procedure.

Light that travels down sample arm 506 ultimately impinges upon sample 510. Sample 510 may be any suitable sample to be imaged, such as tissue. The light scatters and reflects back from various depths within sample 510 and the scattered/reflected radiation is collected back into sample arm 506. In another embodiment, the scattered/reflected radiation is collected back into a different waveguide than the transmitting waveguide. The scan depth may be chosen via the delay imposed on the light within delay unit 512.

Light within sample arm 506 and reference arm 508 is recombined before being received at detector 514. In the embodiment shown, the light is recombined by splitting element 504. In another embodiment, the light is recombined at a different optical coupling element than splitting element 504. Detector 514 may include any number of photodiodes, charge-coupling devices, and/or CMOS structures to transduce the received light into an electrical signal. The electrical signal contains depth-resolved optical data related to sample 510 and may be received by a processing module. The processing module has an interface that converts such electrical signals into digital data that can then be processed and analyzed by a standard processing unit such as a computer, a data processor, reprogrammable hardware, ASICs or any other types of digital data processing circuits or systems.

As used herein, the term "depth-resolved" defines data in which one or more portions of the data related to specific depths of an imaged sample can be identified. LCI system is illustrated as an interferometer design similar to a Michelson interferometer, according to an embodiment. However, other interferometer designs are possible as well, including Mach-Zehnder or Mireau interferometer designs.

Exemplary Embodiments of External Elements of the System

As illustrated in FIG. 1, several elements of the system may be external to and directly or indirectly connected to the catheter 100. Such elements may be contained in multiple enclosures or a single enclosure. In the configuration shown in FIG. 1, a console 101, a user interface 104, and an ablation energy source 102 are housed in independent enclosures. In some embodiments, parts of the optical circuit 500 are encased within the console 101 and parts within the catheter 100. In further embodiments, the ablation energy source 102 may also be encased within the console 101. Elements of the user interface 104 may be enclosed within the console 101 and other elements within a display module. In some embodiments, the external elements of the system also include a processing module, which can be encased in combination with any of the other external elements, such as within the console 101. The processing module may contain some of the elements of the optical circuit 500 or just receive signals from the optical circuit 500. The processing module may also include additional circuitry to measure the signal generated at optical detector 514 and use it to produce data that may be further processed and analyzed. In some embodiments, a processing unit of the processing module, other elements of the processing module, the catheter 100, the ablation energy source 102, and the console 101 may be directly or indirectly connected to the user interface 104. The user interface 104 may send auditory, visual, and/or tactile data to a user to inform him or her of the characteristics of the sample 510 and status of the ablation system and treatment variables, before, during, and/or after ablation energy is delivered. The data provided by the user interface 104 may be used by clinicians to make a better informed decisions on ablation treatments.

Exemplary Embodiments of Determining Birefringence of Tissue

Birefringence is the optical property of a material, which is associated with the polarization and propagation direction of light. Most viable human soft tissue are generally considered to be birefringent (e.g., myocardium, renal, brain tissue, and the like). This birefringence comes from the organization and geometry of their internal components and structures. Most notably, the organization and geometry of proteins, and/or the organization and alignment of cells within a tissue, are significant determinants of tissue birefringence. Optical birefringence changes in tissue when some of its internal proteins pass from their normal state to a denatured state as the geometry of the proteins themselves and their arrangement within a matrix, changes. Collagen, elastin and fibrin are extracellular matrix proteins that when denatured can affect the birefringence property of a tissue, as the light reflected or scattered from such extracellular matrix may have a different polarization state (e.g, polarization and phase retardation) when compared to the optical signal received when these proteins are in a normal state. Further, other proteins in the cellular membrane and the intracellular cytoskeleton when denatured may also generate a change in the polarization state of light when denatured, or when the geometry of the cellular membrane or cytoskeleton changes, affecting the anisotropy of the tissue.

Exemplary Embodiments of RF Ablation and Determining Birefringence of Tissue

By using RF catheters or other medical delivery devices, RF energy may be delivered into the tissue to cause heating. After a tissue reaches approximately 50° C., a permanent thermal lesion may occur through necrosis. Protein denaturation may occur at approximately 70° C. Therefore, a catheter system as described herein uses polarization-sensitive LCI to interrogate the optical state of an ablated sample and allows direct visualization in real-time as tissue reaches 70° C. in a depth-resolved fashion by analyzing the signal of the reflected and scattered light and its polarization state and phase retardation, with further information of time of flight, frequency and amplitude of the optical signal. In additional embodiments, predictive algorithms using extrapolation, statistical fitting, interpolation, or artificial intelligence (e.g., machine learning) may be applied to lesion libraries to better predict permanently-ablated lesion geometry (e.g., width, length, and/or depth of a lesion). In some embodiments, the algorithms may consider the geometry of the lesion that has been directly visualized to reach 70° C. and calculate the geometry of the tissue sample that has reached 50° C. The geometry of the lesion that has reached 50° C. determines the region of tissue permanently ablated that will not have cardiac rhythm electrical conductivity. Determining and visualizing such geometry allows for the clinician to assess if the lesion has fully penetrated the tissue wall or reached the desired structures at the site of ablation and if there are gaps in the ablation line.

In some configuration of the optically guided ablation system, the penetration depth of the light, which can be used for direct visualization, and its extrapolation of the lesion size at 50° C. might not be enough to determine complete penetration into the tissue wall. In such cases, mathematical algorithms may be used to predict lesion size when the ablation time in that particular lesion needs to go beyond the time that it takes to reach a change in birefringence at the maximum depth of penetration of the light used for direct optical assessment in the tissue. Experimentation using the system described herein has shown that a ratio of a total ablation time over a time to denaturation may be the primary predictor of lesion size when used in a statistical fitting algorithm (e.g., interpolation, extrapolations, regressions, minimum residuals, ANOVA, MANOVA, etc.) or artificial intelligence algorithm (e.g., machine learning). In some embodiments, a time to denaturation may be defined as the time needed to reach denaturation at 70° C. at a known depth. In some embodiments, the known depth used may be the maximum depth for a resolvable optical signal to be analyzed for changes in polarization depth, which may be approximately 1.5 mm for infrared/near infrared. Therefore, the processing unit of the optically guided ablation system may be used in combination with such algorithms to predict in real-time lesion depth beyond the depth for direct visualization and transmit such information to the clinician through the user interface 104.

Exemplary Embodiments of Methods for PFA and Determining Birefringence of Tissue Pulsed field ablation (PFA) uses electromagnetic pulses to generate lesions in tissue during the ablation process. Generally, PFA pulses are applied across two electrodes at a time, spaced in relatively close proximity on the segment of tissue at which a lesion is desired. A series of high voltage pulses, either monophasic or biphasic, is imposed across the electrodes, briefly exposing the tissue between them to a high intensity electric field. In some embodiments, a series of pulses may be referred to herein as a pulse train. In some embodiments, if the energy density, intensity and overall strength of the pulse train is enough to cause cell/tissue necrosis through thermal damage, clinical applications and protocols for PFA may be aimed at creating non-thermal lesions through cell apoptosis or other types of non-necrotic delayed cell death.

During clinical protocols for PFA, a pulse train of a known frequency, amplitude, and duration is applied between two or more electrodes (e.g., in contact or in close proximity to the tissue) at the ablation site to cause opening of pores in the cell membrane of cells in the targeted tissue segment. Opening of such pores causes cell edema, and if such edema is sufficient, an apoptotic (or other delayed cell death) mechanism is activated in the cell, leading to subsequent cell death. Therefore, polarization-sensitive LCI methods directed at determining changes in tissue birefringence due to proteins denaturization at 70° C. may not be sufficient when using PFA, since that temperature might not be reached at the tissue, or only a minimal surface area of tissue in direct contact with the electrodes may undergo denaturization and necrosis. In some embodiments, all or a vast majority of the interrogated tissue sample may undergo delayed cell death with non-thermal damage.

Figure 6:
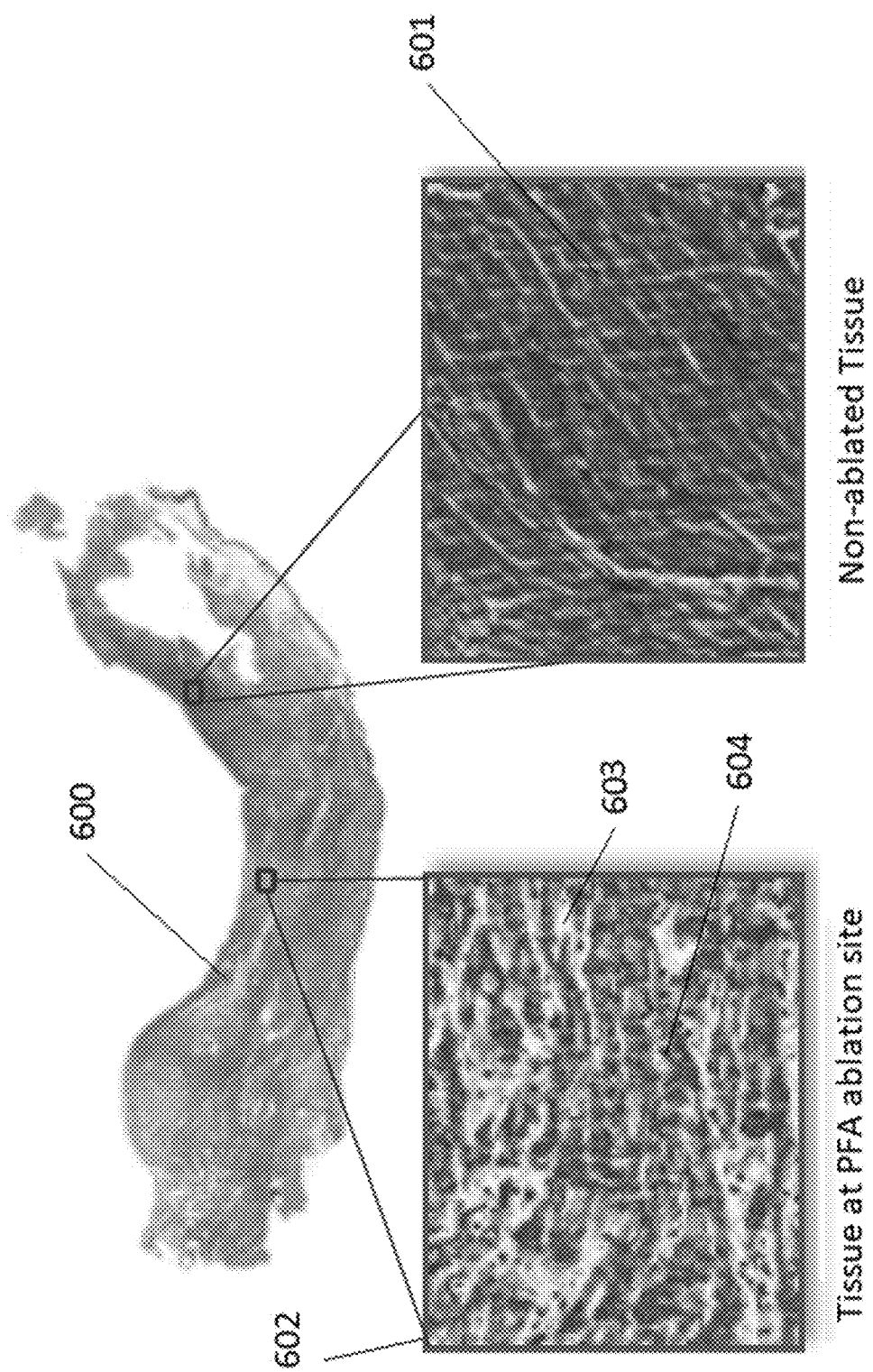
FIG. 6 illustrates a diagram of example experimental histological images of myocardial tissue for a non-ablated sample and a sample after PFA ablation, according to embodiments of the present disclosure.

Experimentation using the polarization-sensitive LCI ablation system described herein has shown to be sensitive to changes in birefringence of tissue associated with application of a PFA energy train in absence of thermal damage. FIG. 6 illustrates a diagram of example experimental histological images of myocardial tissue 600 for a non-ablated sample and a sample after PFA ablation, according to embodiments of the present disclosure. In particular, FIG. 6 shows histology results comparing non-ablated tissue to PFA-ablated tissue that showed changes in birefringence in the polarization sensitive LCI system. After a PFA ablation train is applied, the pulses cause disruptions in the cell membrane and cell membrane proteins, leading to cell edema and subsequent apoptosis (delayed cell death), as shown in FIG. 6 by the loss in tissue integrity and structure The myocardial tissue sample 600 shows two adjacent areas with two very different structures. The non-ablated area 601 shows an organized and densely packed cell structure supported by cell membranes, intracellular cytoskeletons, and extracellular matrixes. The sample of PFA ablated tissue 602 shows completely disrupted cell membranes and intracellular cytoskeletons, cell nuclei 604 outside such membranes, and enlarged gaps 603 in the cell structure and extracellular matrix.

Proteins and structures responsible for maintaining and organization in cell structure and therefore anisotropic (e.g., birefringence) of the tissue include: extracellular matrix (e.g., collagen, elastins), cytoskeleton/flagella or cilia (e.g., tubulin, actin, or lamin), and cellular membrane proteins (e.g., integral/transmembrane proteins). In some embodiments, PFA ablated tissue sample 602 showed a change in birefringence in the LCI system after ablation. For different PFA ablation lesions during experiments, changes in birefringence were observed within a few seconds (e.g., less than 30 sec) or within several minutes (e.g., up to 40 min) after delivery of the PFA energy (e.g., pulse train) to the tissue. The time for detection of changes in birefringence depended on the strength (e.g., amplitude of pulse), type (monophasic, biphasic), frequency (e.g., frequency of pulse) and duration of the pulse train (e.g., the total time for all pulses to be delivered to the tissue).

In some embodiments, delayed changes in birefringence might not be an immediate necrotic mechanism, but a delayed apoptotic/delayed cell death/remodeling response. Delayed changes in birefringence may be associated with delayed changes (reduction) in the anisotropy of the tissue structure. As seen in the histology of the PFA ablated tissue 602, structural integrity and geometrical and organizational changes are seen at a tissue and cellular level. The organization in the non-ablated sample 601 of the cellular structure with an organized matrix determines the anisotropy of the tissue, which is lost after PFA ablation (as shown in sample 602) due to subsequent cell death after apoptosis and cell edema. Therefore, loss in anisotropy in tissue after PFA ablation and subsequent cytoskeletal failure, protein denaturization or fragmentation leads to loss in birefringence, which may be detectable due to changes in polarization and phase retardation by an LCI optically-guided ablation system. Apoptotic process from cell edema may directly affect the intracellular cytoskeletons, its structural proteins, such as tubulin (the protein component of microtubules), actin (the component of microfilaments) and lamin (the component of intermediate filaments), and connection to the extracellular matrix. Disruption of such connections between the cytoskeleton and extracellular matrix may lead to general loss of structure and organization of the tissue segment. Therefore, loss in cytoskeleton integrity may be the primary element that leads to loss of anisotropy and birefringence on the tissue that may be detected by the LCI methodologies described herein.

Exemplary Embodiments of Optically Guided PFA Procedures for Cardiac Ablation

In some embodiments, for the use of a optically guided PFA system for cardiac ablation, a catheter 100 is introduced into the human vasculature directly or through an access sheath. The distal section 201 of the catheter is moved to the site of ablation using guide wires, access sheaths, steerable sheaths, or deflection of the catheter 100 itself. At the ablation site (e.g., atrium, ventricle, artery, vein, etc), at least one or multiple electrodes 213 on the surface of the catheter distal section 201 are placed in direct contact with the tissue at the ablation site. Using light or other forms of radiation emitted by optical source, which travels at least partially through PM optical transmission media to the distal section 201 of the catheter 100, contact or contact stability may be established between the distal section 201 and tissue ablation site. After contact or contact stability is established, a PFA pulse train may be transmitted to the tissue, in which the characteristics of the pulse train (e.g., frequency, amplitude, intensity, or duration) are determined by the clinical user. During and/or after delivery of the ablation pulse train, changes in birefringence of the interrogated tissue may be monitored through assessment of changes in the polarization state and phase retardation of the reflected/scattered light signal, sent into the tissue through the catheter 100. If a change or reduction in birefringence is not detected within a predetermined time frame (such as 1 sec to 1 hour), the clinician may re-ablate the tissue using a pulse train with the same or different characteristics.

In some embodiments, mathematical, statistical or artificial intelligence predictive algorithms or equations, that use time to loss in birefringence or a measure of the change/difference in the amount of birefringence in the ablated tissue, may be used to predict if the PFA lesion is permanent and thus may be associated with a probability of recurrence of cardiac fibrillation. Such algorithms may be used by clinicians to determine the need for re-ablating tissue at the selected ablation site. In some embodiments, such predictive algorithms may be directly programed into the ablation system, and results communicated to the clinician through the user interface 104, or such algorithms or equations may be provided to the clinician for their offline use.

In other embodiments of the ablation procedure, prior to establishing tissue contact at the ablation site, the distal section 201 of the catheter 100 may undergo geometrical changes to create 2D and 3D structures equivalent but not limited to those shown in FIGS. 4A-4D to provide better contact or accommodate the catheter to local anatomy.

In some embodiments of the PFA optically-guided ablation procedure, the catheter may be held in place for a predetermined amount of time needed after ablation, in which changes in birefringence are expected to occur. In other embodiments of the procedure, after ablation, the catheter 100 is moved to another ablation site in the body. After a predetermined amount of time, the catheter 100 is moved back to the first ablation site to monitor if the PFA pulse has generated a change in birefringence of the tissue. In a further embodiment, the catheter may be removed from the body, and the same catheter 100 or another similar catheter may be re-used at a later time of re-intervention to be moved again to the first ablation site to monitor if the tissue has shown changes in birefringence due to the initial PFA pulse train.

Exemplary Embodiments of Optically Guided Renal Denervation Procedure

In some embodiments, for the use of a optically-guided ablation system for renal denervation, a catheter 100 is introduced into the human vasculature directly or through an access sheath. The distal section 201 of the catheter is moved to the site of ablation (e.g., renal artery) using guide wires, access sheaths, steerable sheaths, or deflection of the catheter 100 itself. At the ablation site (e.g., renal artery), at least one or multiple electrodes 213 on the surface of the catheter distal section 201 are placed in direct contact with the tissue at the ablation site. Using light or other forms of radiation emitted by optical source, which travels at least partially through PM optical transmission media to the distal section 201 of the catheter 100, contact or contact stability may be established between the distal section 201 and tissue ablation site. After contact or contact stability is established, RF energy may be transmitted to the tissue, in which the characteristics of the RF energy (e.g., power, duration, etc.) are determined by the clinical user. During delivery of the ablation RF energy, changes in birefringence of the interrogated tissue may be monitored through assessment of changes in the polarization state and phase retardation of the reflected/scattered light signal, sent into the tissue through the catheter 100. The RF energy may be applied until the tissue is ablated up to the desired depth as predicted by the algorithms or equations in the system, which uses time to denaturization or the ratio between total ablation time and time to denaturization as predictive variables. In some embodiments, the catheter may be moved as needed to complete ablations through the complete circumference of the renal artery.

In some embodiments of an optically-guided ablation method for renal denervation, the user may move the catheter to the ablation site and re-interrogate the tissue using the optical signal to determine the loss in birefringence through the circumference to insure the absence of gaps.

In other embodiments of the ablation procedure for renal denervation, prior to establishing tissue contact at the ablation site, the distal section 201 of the catheter 100 may undergo geometrical changes to create 2D and 3D structures equivalent but not limited to those shown in FIGS. 4A-4D to provide better contact or accommodate the catheter to local anatomy.

In some embodiments of the renal denervation procedure described above, prior to delivery of the ablation energy, radiation/light travelling at least partially through a multi-mode optical transmission media (multimode fiber or waveguide) may be used, in which the light is processed and analyzed using optical spectroscopy methods to determine the depth at which the renal nerve is located with relation to the renal artery wall. In some embodiments, the system may include both independent single mode optical paths and multi-mode optical paths to use both LCI and spectroscopy in the same ablation catheter system. In some embodiments, ultrasonic technology may also be added to the LCI catheter. In such an exemplary ultrasonic technology catheter, the ultrasonic signal may be used to determine the depth of the renal nerve prior to ablation.

Exemplary Embodiments of Optically Guided Ablation for Treatment of Epilepsy

In some embodiments, for the use of a optically guided ablation system for treatment of epilepsy, a catheter 100 is introduced into the human vasculature directly or through an access sheath. The distal section 201 of the catheter is moved to the site of ablation using guide wires, access sheaths, steerable sheaths, or deflection of the catheter 100 itself. At the ablation site (e.g., discrete epilepsy foci) at least one or multiple electrodes 213 on the surface of the catheter distal section 201 are placed in direct contact with the tissue at the ablation site. Using light or other forms of radiation emitted by optical source which travels at least partially through PM optical transmission media to the distal section 201 of the catheter 100, contact or contact stability may be established between the distal section 201 and tissue ablation site. After contact or contact stability is established, RF energy may be transmitted to the tissue, in which the characteristics of the RF energy (e.g., power, duration, etc.) are determined by the clinical user. During delivery of the ablation RF energy, changes in birefringence of the interrogated tissue may be monitored through assessment of changes in the polarization state and phase retardation of the reflected/scattered light signal, sent into the tissue through the catheter 100. The RF energy may be applied until the tissue is ablated up to the desired depth as predicted by the algorithms or equations in the system, which uses time to denaturization or the ratio between total ablation time and time to denaturization as a predictive variables. In some embodiments, the catheter may be moved to other epileptic foci as desired to repeat ablation steps.

Figure 7:
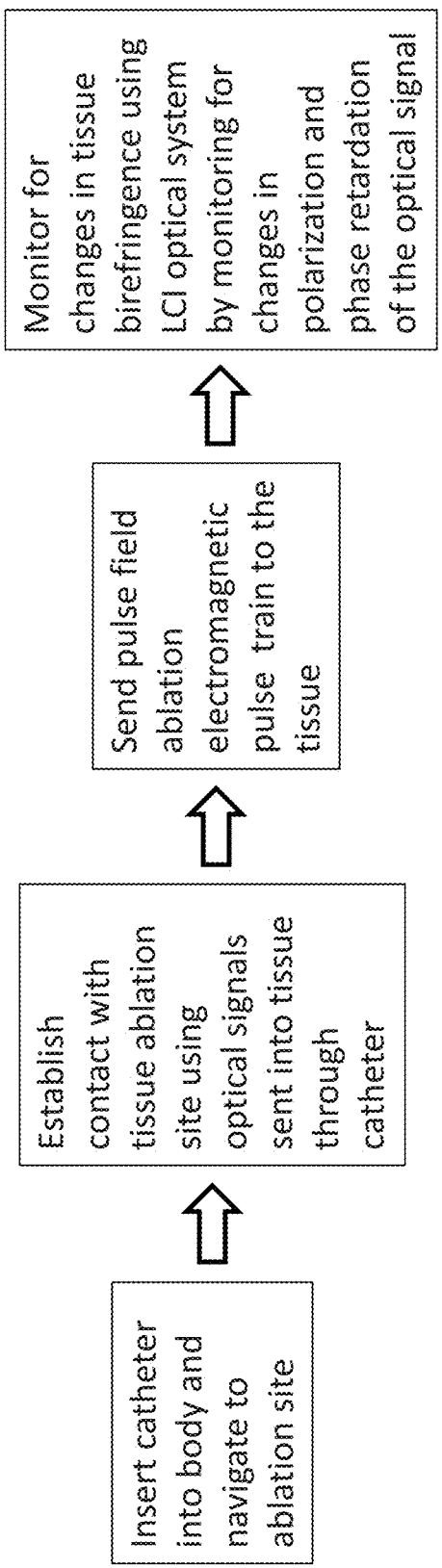
FIG. 7 illustrates an example method for the clinical use of an optically guided pulsefield ablation system, according to embodiments of the present disclosure.

FIG. 7 illustrates an example method for the clinical use of an optically guided pulse field ablation (PFA) system, according to embodiments of the present disclosure. In some embodiments, the method may include inserting a catheter into a patient's body and navigating to a tissue ablation site and establishing contact with the tissue ablation site using optical signals transmitted into tissue through the catheter. The method further includes sending a PFA electromagnetic pulse train to the tissue through the catheter, and monitoring for changes in tissue using an LCI optical system by monitoring for changes polarization and/or phase retardation of an optical signal.

Exemplary Embodiments of Pulse Field Ablation Catheters with Integrated Optics

As described herein, catheter devices may be configured to deliver pulse field ablation (PFA). Specific applications include PFA delivered to the left atrium of the heart in a non-invasive procedure, to treat atrial fibrillation.

Generally, PFA pulses are applied across two electrodes at a time, spaced in relatively close proximity on the segment of tissue at which a lesion is desired. A series of high voltage pulses, either monophasic or biphasic, is imposed across the electrodes, briefly exposing the tissue between them to a high intensity electric field. Pulse trains may be on the order of 500-1500 Vpp (voltage peak-peak) and may be centered on zero volts (biphasic) or be single-ended going from zero to peak voltage. In some cases, the pulses may be square or sinusoidal, each pulse typically of a duration of 10-100 microseconds, and between 10 and 25 pulses applied at intervals between 0.5 and 2 seconds. The electric field, and thus the resultant lesion in the tissue, may extend from one electrode to the other. The lowest current density in the lesion zone will be at the midpoint between the electrodes, with current density increasing as one approaches either electrode. The electric field is intended to cause irreversible electroporation of the cells within it, which eventually causes delayed cell death. Depending on the location of the cell within the field, that delayed cell death can be processed through apoptosis, pyroptosis, necroptosis, and the like.

When delivered correctly, PFA has been shown to effectively ablate tissue at selected locations, creating a permanent lesion that prevents spurious electrical signals from propagating across the atrial wall and further into the heart, and preventing further unwanted fibrillation. However, if the PFA pulses are not delivered optimally, the lesion may be incomplete and may fail to interrupt spurious signals, resulting in remodeling that leads to a resumption of fibrillations later on, (e.g., sometimes as long as several years after the procedure). Suboptimal PFA delivery can result from numerous causes, including improper positioning of electrodes, poor electrode contact, contact motion during delivery, or an inadequate combination of pulse train parameters such as voltage, current, pulse width, number of pulses, pulse duration, decay time, mono versus biphasic modality, etc. Should deficiency in any of these parameters lead to resumption of fibrillation days or years after the procedure, a second procedure may be needed, exposing the patient to additional risk and incurring additional cost.

Medical catheters may also contain optical systems that use Optical Coherence Reflectometry (OCR) to sense parameters such as endocardial wall contact, tissue viability, lesion formation, and lesion depth and width, among others. OCR methods may include measuring reflection amplitude, birefringence, degree of polarization, etc, to determine contact quality, cell status, and lesion dimensions. Some devices incorporate micro-optics within the catheter for probing the target tissue, and fiberoptic cables that extend through the catheter to connect proximally to an external console that provides optical sources and receivers, switches, reference arm, control electronics, data processing, and a display. Current optical devices, however, are generally directed toward combination optical and electrical catheters that employ Radiofrequency Ablation (RFA), rather than PFA.

Thus, there is an unmet need for reliable devices and methods that increase the probability of creating a permanent lesion with PFA during a single minimally invasive surgical procedure. The means should allow the physician performing the procedure to assess, in real time during the procedure: (i) contact between the stimulating electrodes and the target anatomy, and (ii) effectiveness of the ablation after stimulus is applied, including the depth and area of the lesion. If poor contact is detected, the physician can reposition the catheter prior to applying energy to the catheter's electrodes. If insufficient lesion depth or width is detected, the physician can apply additional PFA pulses to the problem area until a satisfactory lesion is observed. These assessments will enable the physician to create and verify an uninterrupted, effective lesion at the time of surgery, and thus reduce the risk of fibrillation reoccurrence and repeat procedures.

Generally, PFA pulses are applied across two electrodes at a time, spaced in relatively close proximity on the segment of atrial wall at which a lesion is desired. This is typically in the atrial wall area surrounding each of the four pulmonary vein ostia. A series of high voltage pulses, either monophasic or biphasic, is imposed across the electrodes, briefly exposing the tissue between them to a high intensity electric field. In exemplary embodiments, pulse trains may be on the order of 500-1500 Vpp and may be centered on zero volts (biphasic) or be single ended going from zero to peak voltage. The pulses may be square, each pulse typically of duration 10-100 microseconds, and between 10 and 25 pulses applied at intervals between 0.5 and 2 seconds. The electric field, and thus the resultant lesion, will extend from one electrode to the other. The lowest current density in the lesion zone will be at the midpoint between the electrodes, with current density increasing as one approaches either electrode. The electric field is intended to cause irreversible electroporation of the cells within it, which eventually causes apoptosis.

To optically assess the lesion, at least one optical viewport may be placed at a precisely known point—either the midpoint or some other point—in the space between the electrodes. In practice such placement is difficult due to precision limitations of location visualization systems such as fluoroscopy, ultrasound, RF-based or other mapping/navigation systems.

Depending on the specific optical measurement technology and electrical stimulus selected, there may be a time lag between application of voltage and the appearance of detectable changes in the ablated cells. This time lag may last anywhere from 30 seconds to 30 minutes. Once electrical stimulus is applied, it may be necessary to hold the device in the same location during the time lag in order to observe the desired changes and confirm successful or unsuccessful ablation.

Figure 8:
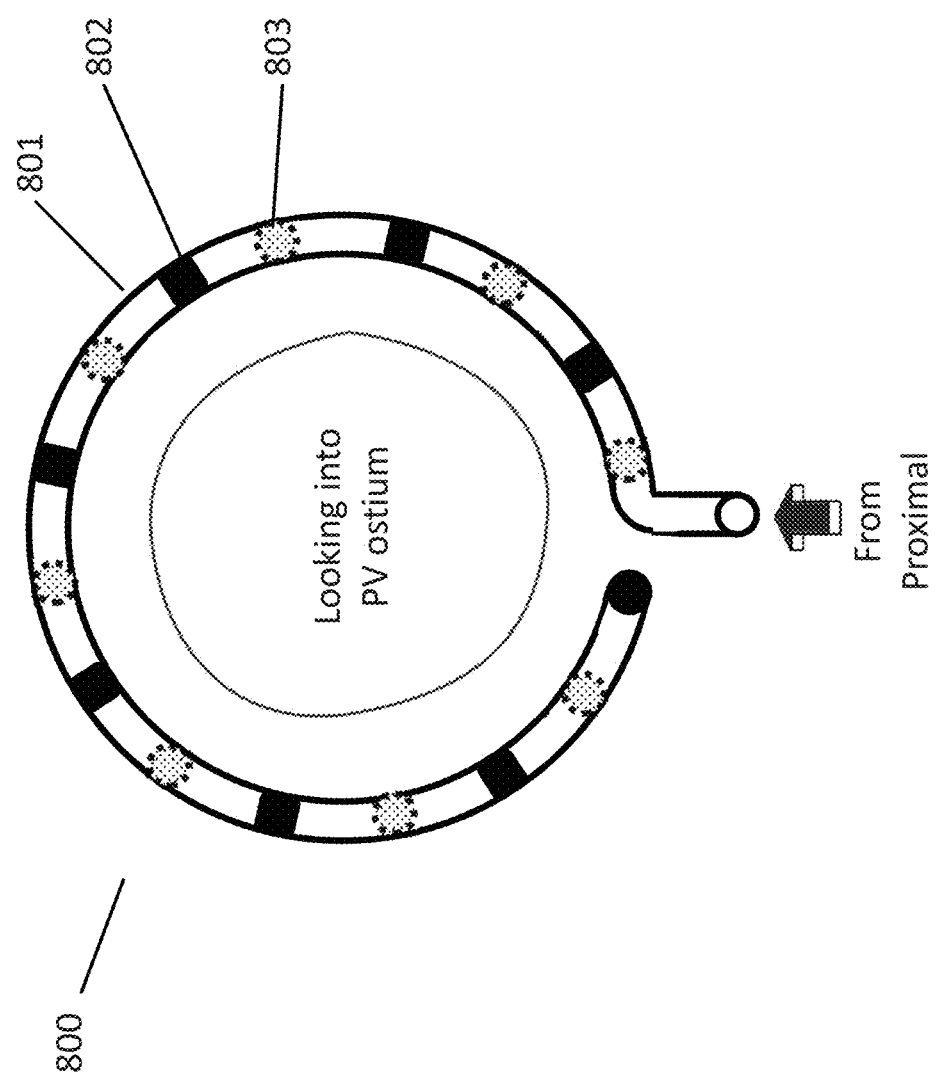
FIG. 8 illustrates a diagram of an example distal end of a PFA-OCR catheter with a circular shape, according to embodiments of the present disclosure.

FIG. 8 illustrates a diagram of an example distal end of a PFA-OCR catheter with a circular shape, according to embodiments of the present disclosure. An embodiment of a PFA-OCR catheter 800, shown in FIG. 8, may outwardly resemble a generic circular mapping catheter at its distal end. A circular shape is shown as an exemplary embodiment, but the catheter distal section may be configured as a circle, oval, or any polygon or combination of polygons. The shape may be configured to surround a pulmonary vein ostium and be deployed through a delivery catheter. FIG. 8 provides a front view looking into the pulmonary vein ostium, the pulmonary vein extending into the plane of the page. In some embodiments, the delivery catheter may be of size 8 Fr or smaller (e.g., 2.66 mm or smaller). The body 801 of the circular distal end of catheter 800 may be formed from a nonconductive polymer such as polyvinyl chloride (PVC), a polyamide, or PeBax®. The body 801 may have metal electrodes 802 spaced evenly along its length, made of a biocompatible material such as platinum, platinum iridium, gold, or stainless steel, as well as other metals or metal plating. While the catheter 800 shown in FIG. 8 illustrates 8 electrodes, the device may have between 24 and 32 electrodes 802. The electrodes 802 are on the outside of the polymer body 801, exposed to allow contact with the endocardial wall. The electrodes 802 may partially or fully encircle the body 801, but may have sufficient area to contact the vessel wall in light of surface irregularities. Inside a lumen in the body 801, each electrode 802 may attach to a wire that may extend down the catheter's shaft, the wires terminating in an electrical connector at the proximal end. The connector may plug into a dedicated console that provides electrical and optical energy to the catheter, and senses optical and electrical signals coming back from the catheter.

Between each pair of neighboring electrodes 802 is an optical port 803, which may be configured as an opening on the side of body 801 that faces the endocardium—the reverse side of body 801 in FIG. 8. While FIG. 8 shows eight optical ports 803 for illustrative purposes, any number of port counts may be used. In some embodiments, any number of optical ports 803 and electrodes 802 may be placed in any configuration as long as a port 803 is not in the same location as an electrode 802, with a minimum of two electrodes 802 and one port 803. In some embodiments, optical ports 803 may be referred to herein as orifices or openings (e.g., openings 803A and 803B as shown in FIG. 9) formed in the catheter body 801.

Figure 9:
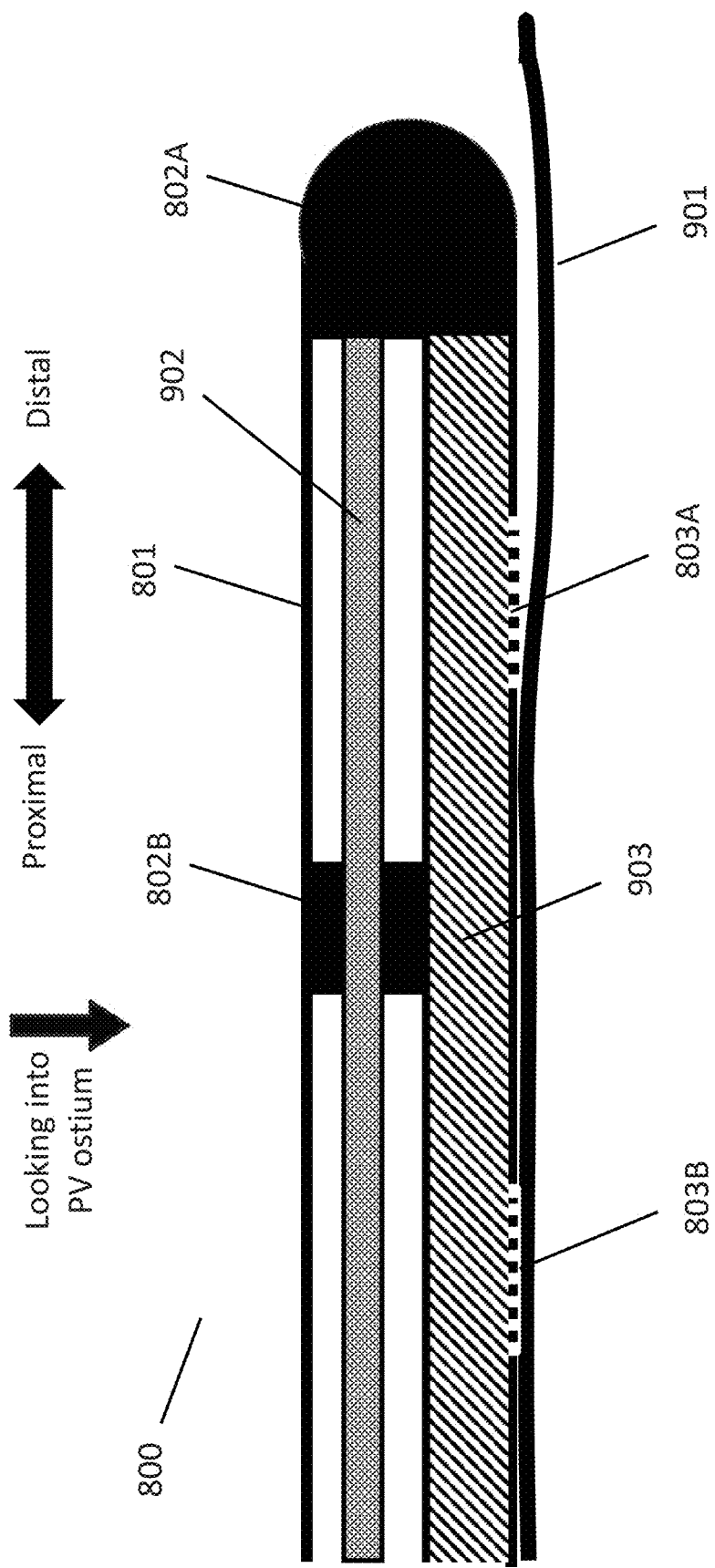
FIG. 9 illustrates a diagram of an example cross-section of a side view of a distal tip portion of the distal section of a PFA catheter with OCR diagnostic functionality, according to embodiments of the present disclosure.

FIG. 9 provides a close-up cross-section side view of the distal tip of the catheter 800's circular distal end. For clarity, it is shown in a straight uncurled position, as it would be when contained in its delivery catheter (not shown). When deployed, distal end of catheter 800 is positioned with the distal plane of its circular shape in contact with endocardial wall 901 as in FIGS. 8 and 9. The outside of catheter body 801 is provided with electrodes 802A and 802B, with additional electrodes 802 spaced along the body 801 shown in FIG. 8 but not shown in FIG. 9. Electrode 802B is shown in cutaway but may encircle the outer surface of body 801 completely or partially. Electrodes 802 are positioned on body 801 such that at least a portion of each electrode 802 faces into the distal plane of body 801's circular shape and contacts wall 901 when mild force is applied to the catheter.

Inside catheter body 801, at least one wire lumen 902 may extend down the length of the catheter. Holes, skives, or slots at intervals along wire lumen 902 may allow the passage of electrical wires through to connect to each of the electrodes 802. The electrode wires (not shown) may extend down the length of wire lumen 902 and may terminate at an electrical connector at the catheter's proximal end (not shown). Wires may attach to electrodes 802 by solder, crimp, wedge bond, ultrasonic weld, laser weld, conductive epoxy, or other means. In one embodiment, each electrode 802 is attached to a dedicated wire, allowing each electrode 802 to be accessed similarly by the control circuitry in the console (not shown). The console electronics may use electrodes 802 for several functions: (i) to apply PFA stimulus; (ii) to measure electrogram signals; (iii) to interface with a navigation or mapping system, or; (iv) to measure tissue impedance. Electrodes 802 may be multiple use across several of these functions, or may be dedicated to a single function. The set of electrodes 802 may include any combination of single use or multi-use electrodes.

In an alternative embodiment, a plurality of electrodes 802 may be connected together in parallel to form a single node. For example, when referring to the electrodes 802 in FIG. 8, a user may move sequentially around the circle in a counterclockwise direction and connect every other electrode 802 together. Thus the $1^{st}$, $3^{rd}$, $5^{th}$, and $7^{th}$ electrodes 802 may form one node, and the $2^{nd}$, $4^{th}$, $6^{th}$, and $8^{th}$ electrodes 802 may form a second node. In this configuration, a PFA stimulus event may use the even numbered electrodes 802 as one pole and the odd numbered electrodes 802 as the other pole, thus ablating the entire circular area all at once.

Although a single wire lumen 902 is shown in FIG. 9, other embodiments may provide a plurality of lumens, each containing a subset of the electrical wires used in the system.

Returning to the cross-section in FIG. 9, catheter body 801 may further provide internal optical lumen 903, that may extend down the length of catheter 800. Optical lumen 903 may be located near to or abutting with the distal plane of the circular distal portion of 800 that is in contact with endocardial wall surface 901. One or more openings 803

(e.g., openings 803A, 803B) may be provided in optical lumen 903, exposing optical lumen 903 to the outside of catheter. The openings 803 may be used to project light out of the catheter and into endocardial wall 901, and to receive back-reflected light into the catheter for measurement. The openings 803 may be holes, slots or skives formed in catheter body 801. They may be open to the outside or may be covered by an appropriate optically transparent covering, such as glass, polymer, or other ceramic material. FIG. 9 depicts two openings 803A and 803B, but an arbitrary number of openings may be placed at any desired locations around the circular distal section of catheter 800 as shown in FIGS. 8 and 9. In another embodiment, catheter 800's distal section body 801 may be entirely made of an optically transparent material. In some embodiments, openings 803A, 803B may ensure optical transparency between optical lumen 903 and endocardial wall 901 at the wavelengths being used for optical analysis.

Figure 10:
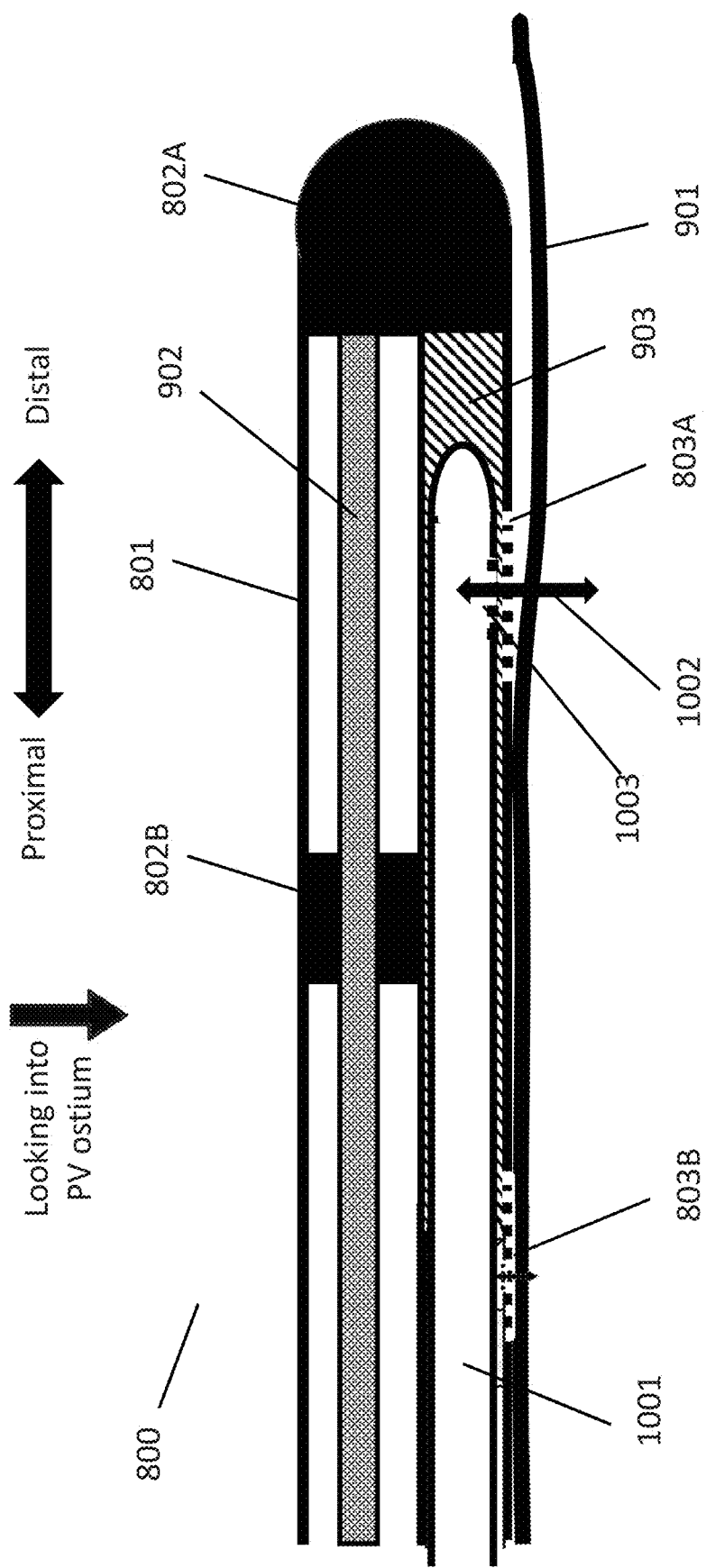
FIG. 10 illustrates a diagram of an example cross-section of a side view of the distal section of a PFA catheter with OCR diagnostic functionality with a separately movable optical catheter inserted in its optical lumen, according to embodiments of the present disclosure.

FIG. 10 illustrates the device shown in FIG. 9, but with optical catheter 1001 inserted into optical lumen 903 from the proximal end at left. Optical catheter 1001 may be moved independently of the distal end of the main catheter 800 system. Movement of optical catheter 1001 may be accomplished by a control at the proximal end of the system (not shown). The control may be part of a proximal handle assembly or may reside in one of the external devices to which the catheter connects. The control may be a simple push/pull wire. The control may be a rotary knob, wheel, lever, slider, pushbutton, or the like. The control may be geared or pinioned to provide precision movement of optical catheter 1001 through optical lumen 903. The control may provide a locking function to hold optical catheter 1001 in place relative to optical lumen 903 and release it again for movement to a new location. The control may be manual or motorized, including stepper motors or linear displacement drives. It may provide a user interface to indicate location of optical catheter 1001 relative to optical lumen 903 or other physical components of the system. The user interface may provide visual, audible, or haptic feedback to the catheter operator.

Near the distal end of optical catheter 1001 is optical opening 1003. When the console projects optical energy 1002 through optical catheter 1001, it may exit catheter 1001 through opening 1003. When opening 1003 is aligned with one of the openings 803 in outer catheter body 801, the optical energy 1002 may exit catheter body 801 and enter endocardium 901. Further, at least some of the optical energy 1002 may reflect back from tissue at or below the surface of endocardium 901 and re-enter optical catheter 1001.

The optical lumen opening 1003 may take any of the forms described previously for openings 803 in the outer catheter body 801. The form of the opening 1003 may be different from openings 803. Optical lumen 903 and optical catheter 1001 may provide features to ensure rotational alignment between opening 1003 and openings 803. The catheter operator may advance and retract optical catheter 1001 along optical lumen 903, stopping at any location where the optical catheter's opening 1003 aligns with an opening 803 on outer catheter body 801. At these locations, the operator may take optical readings to assess tissue parameters of interest. The system may be configured with optical catheter 1001 already partially or fully inserted into optical lumen 903 when catheter 800 is introduced into the target anatomy, which may be the heart. In an alternative embodiment, catheter 800 may enter the target anatomy with optical lumen 903 empty, with optical catheter 1001 being introduced later in the procedure.

In other embodiments, different types of catheters may be exchanged for optical catheter 1001. Optical lumen 903 may accommodate alternative catheters that can perform different functions when aligned with openings 803 on catheter body 801. Examples of exchangeable alternative catheters include catheters for OCR, spectroscopy including near infrared spectroscopy, degree of polarization uniformity or other optical measurements; electrical stimulation or ablation with PFA or radiofrequency energy; electrical sensing including electrogram or impedance measurement; mechanical location marking including placement of markers such as pins clips, or suture wire; other location marking including dye injection or tissue staining for fluoroscopic viewing, ultrasonic viewing, or for compatible electrophysiology navigation systems; biopsy; drug injection into the tissue or elution into the bloodstream; photography or videography; chemical properties measurement; mechanical properties measurement including durometer; local ultrasound; laser suturing or ablation. The outer structure of catheter 800 may allow for precision placement of catheters and precision targeting of locations at windows (e.g., openings 803) for these and other example catheter types. The operator may exchange different catheter types, including variations of the same catheter type, as desired throughout a procedure.

Figure 11:
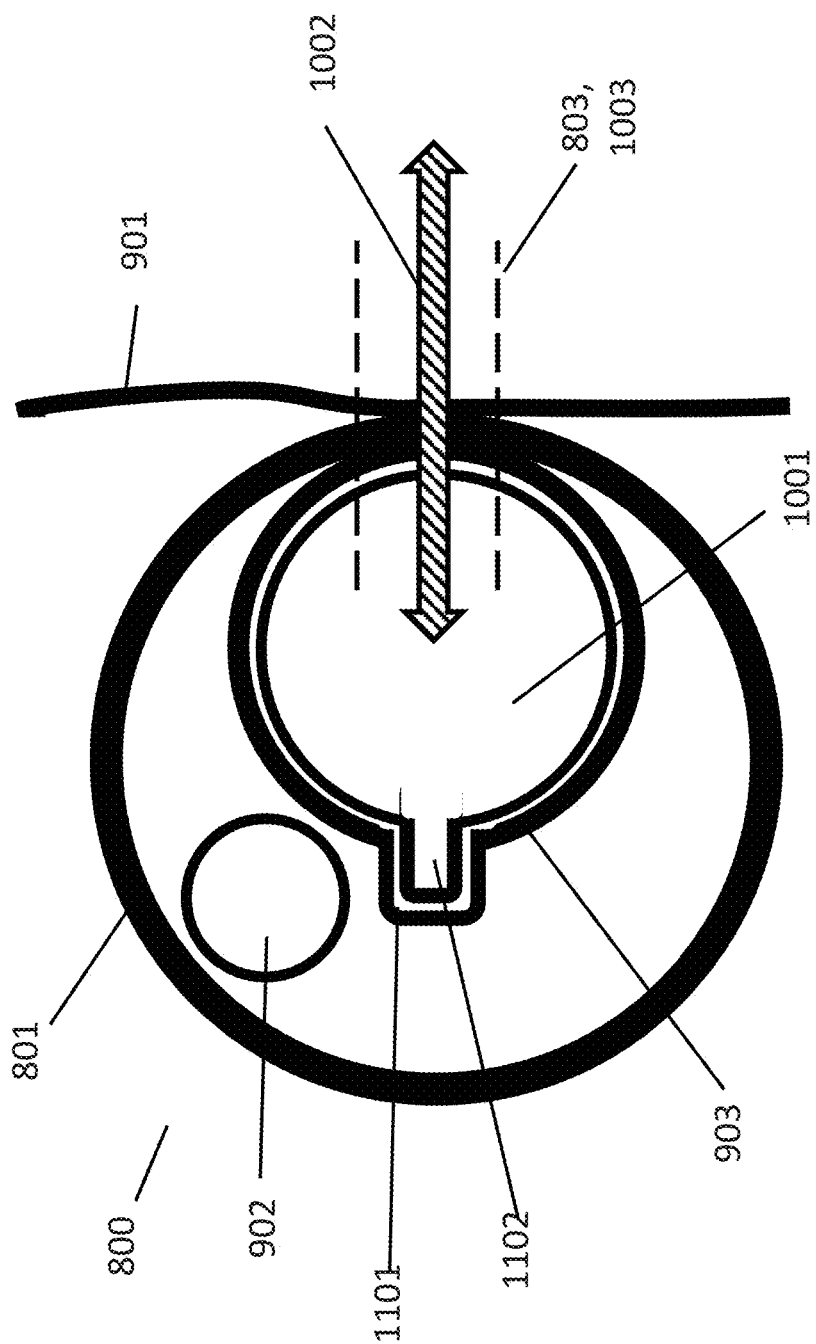
FIG. 11 illustrates a diagram of an example cross-section of a distal section of PFA-OCR catheter, according to embodiments of the present disclosure.

FIG. 11 provides a cross-section of the distal end of catheter 800, looking from proximal towards the distal end, at a location between or outside of electrodes 802 (not shown). The figure is oriented such that endocardial wall 901 is on the right side of the catheter 800. Within catheter 800's body 801 are wire lumen 902, optical lumen 903, and optical catheter 1001, drawn at different scale than in previous figures. Optical lumen 903 abuts with the side of catheter body 801 that is configured to contact endocardial wall 901. Openings 803 and 1003 are cut into catheter body 801, optical lumen 903, and optical catheter 1001 respectively, at the location shown by the two horizontal hashed lines, allowing optical energy 1002 to exit and re-enter optical catheter 1001. Optical lumen 903 is provided with groove 1101, to accept and tongue 502 on optical catheter 1001. Tongue 502 and groove 1101 extend down the length of catheter 800 and ensure rotational alignment between openings 803 and 1003. Optical catheter 1001 may be translated proximal or distal (into or out of the plane of the page in the figure) relative to optical lumen 903, without misaligning openings 803 and 1003. Although a tongue-and-groove alignment is shown in this embodiment, other embodiments may employ different alignment means, including but not limited to: ovular, polygonal, or other interlocking cross-sectional shapes for optical catheter 1001 and optical lumen 903; multiple polygonal tongue-and-groove shapes; a guidewire extending down optical lumen 903 that fits into a smaller lumen inside of optical catheter 1001.

Figure 12:
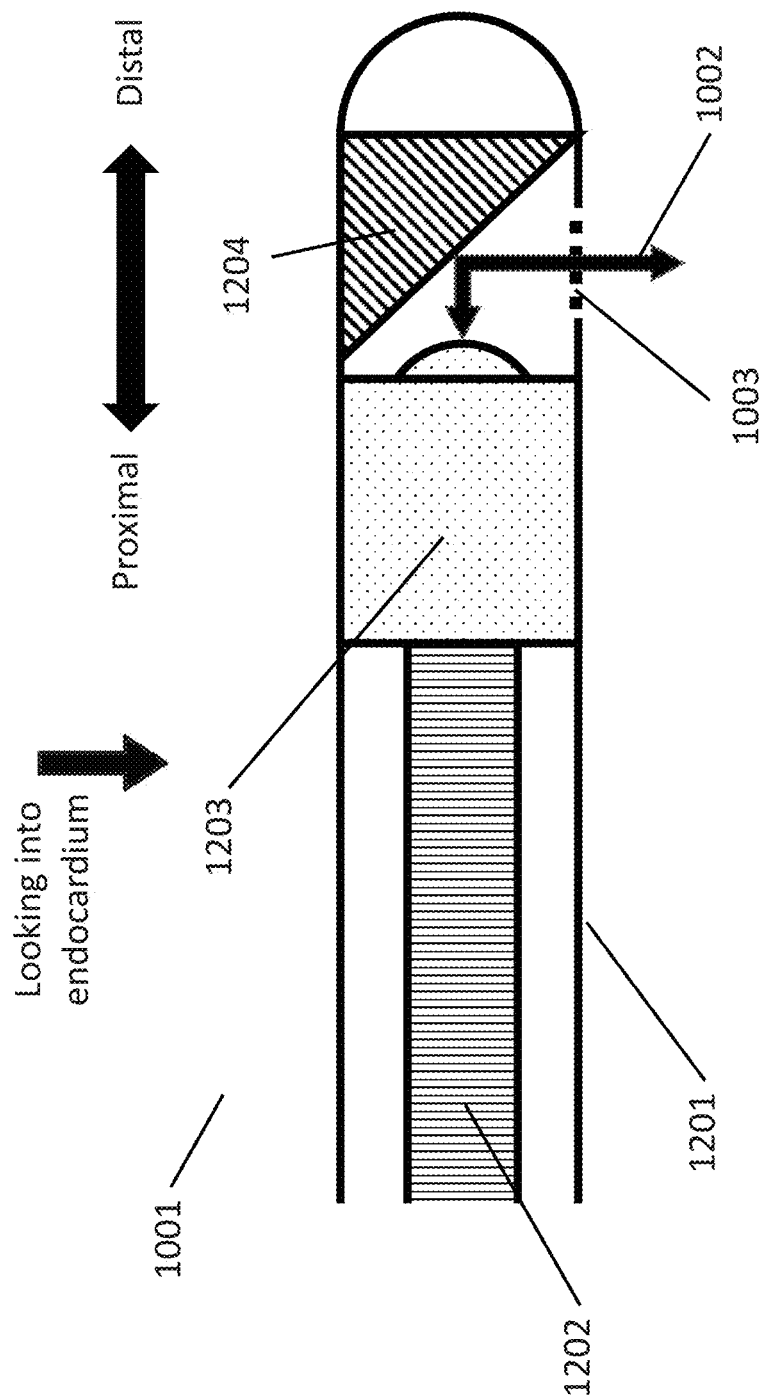
FIG. 12 illustrates a diagram of an example cross-section of a side view of the distal section of the PFA catheter, showing internal components, according to embodiments of the present disclosure.

FIG. 12 is a cross-section sideview of the distal end of optical catheter 1001, showing several internal structures. Catheter body 1201 may contain the rotational locking feature (not shown in FIG. 12) exemplified as tongue 502 in FIG. 11. The body 1201 may contain structures (not shown) such as metal coils to facilitate distal and proximal motion between openings 803, while retaining flexibility to navigate tortuous anatomy during introduction and accommodate the circular or other shape shown in FIG. 8. Inside body 1201, a focusing lens 1203 is rigidly fixed to body 1201. Lens 1203 may be a microlens made of glass, fused silica, silicon dioxide, sapphire, or other materials. Fiber optic cable 1202 may be connected to lens 1203 by an adhesive such as index matching epoxy, laser welding, or other means. In an embodiment, the distal end of fiber optic cable 1202 may be directly polished to act as a lens. Fiber optic cable 1202 may extend down the length of catheter 800 and may terminate at an optical connector (not shown) at catheter 800's proximal end. The optical connector may connect to the console (not shown) to transfer optical energy between the console and the catheter. Focused optical energy 1002 may exit lens 1203 from left to right in the figure and may be turned by angled mirror 1204 to project through opening 1003 and into the endocardium 901 (not shown). Optical energy 1002 may penetrate the tissue layers of endocardium 901 and a portion of it may back-reflect into optical catheter 1001 along the same path by which it entered. Turning mirror 1204 may also be rigidly fixed to optical catheter body 1201, preserving optical alignment by precluding relative motion between lens 1203, mirror 1204, opening 1003, and rotational positioning tongue 502 (not shown in FIG. 12).

Figure 13:
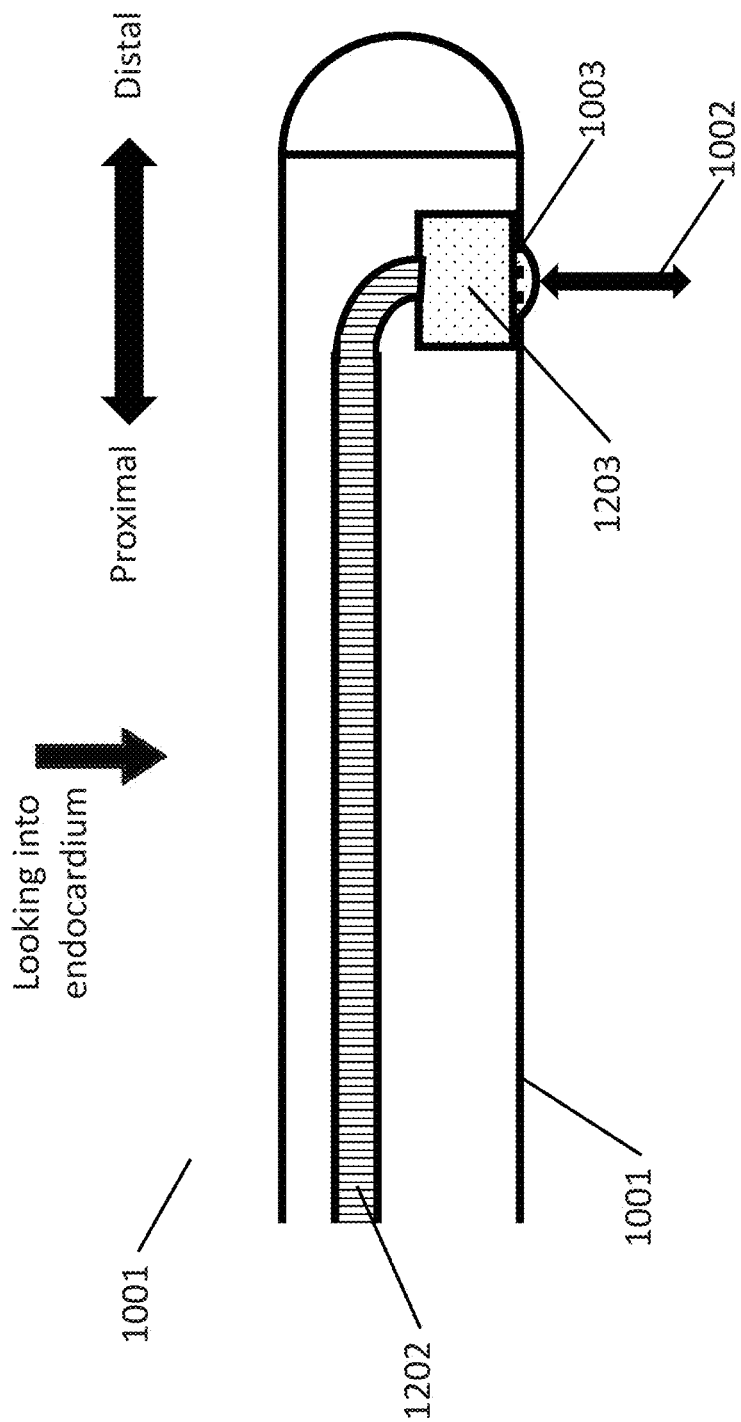
FIG. 13 illustrates a diagram of another example cross-section of a side view of the distal section of the PFA catheter, according to embodiments of the present disclosure.

FIG. 13 provides a cross-section side view to illustrate an alternative embodiment of optical catheter 1001. In some embodiments, mirror 1204 might not be needed as shown in FIG. 13. Instead, a highly flexible optical fiber 1202 is employed that can turn 90 degrees at the attachment point to lens 1203, which is rigidly affixed directly to opening 1003 by adhesive, a separate holder, a shaped structure for accepting the lens, or other means. Other concepts for internal arrangement of optical components within optical Both the external structures in catheter 800 and the internally movable optical catheter 1001 may be provided with coatings or materials at selected locations that facilitate visualization on fluoroscope, navigation mapping, ultrasound, computer tomography, or other imaging systems.

Figure 14:
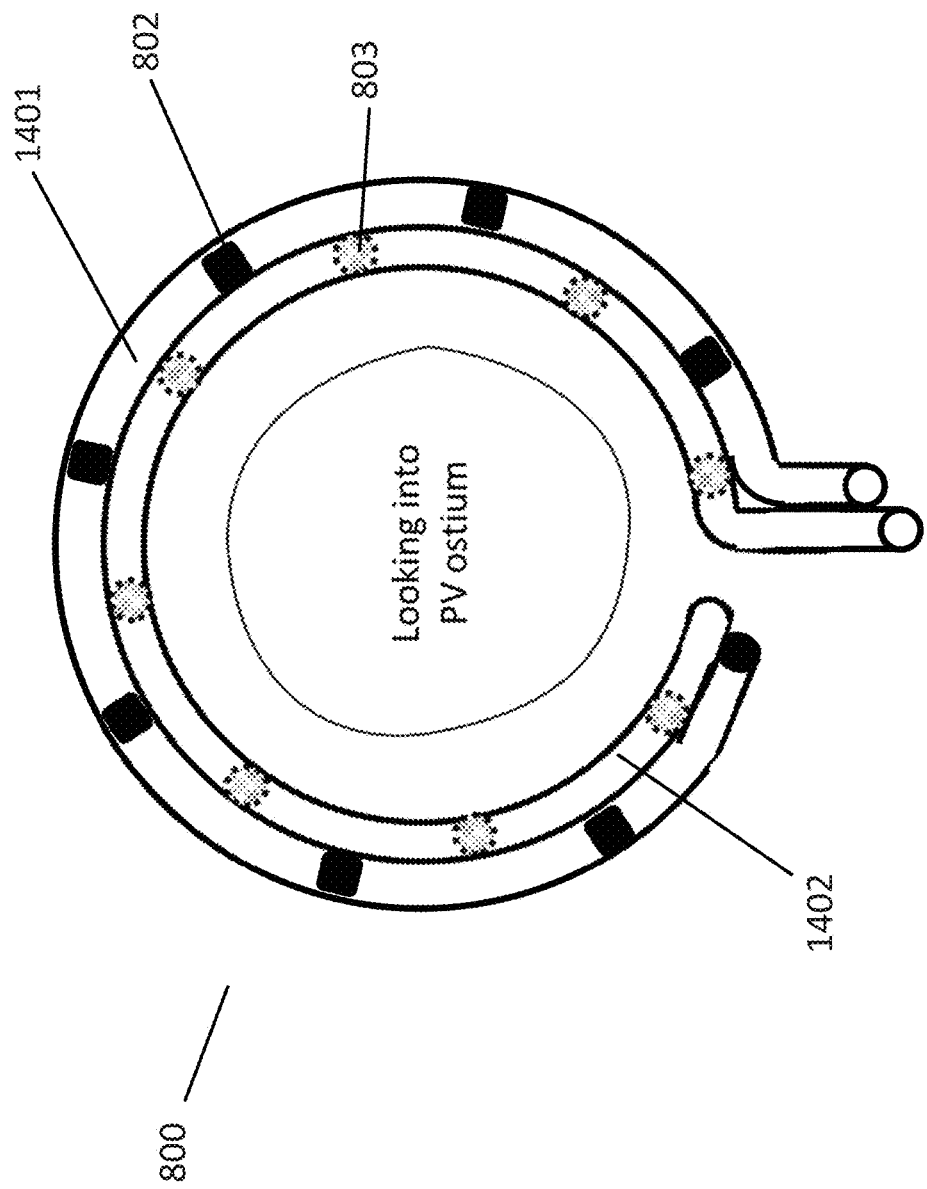
FIG. 14 illustrates a diagram of an example distal end of a PFA-OCR catheter system with two concentric catheters, according to embodiments of the present disclosure.

In an alternative embodiment, the electrodes 802 and the openings 803 may be located on separate catheters that are attached at the side as shown in FIG. 14. In this example, an outer catheter 1401 may resemble the circular distal end of catheter body 801 shown in FIG. 8, and may have electrodes 802 positioned on it at intervals, each electrode 802 connected to an internal wire, and wire may extend proximally through catheter 800 as in FIG. 8 through FIG. 12 embodiments. However, in the FIG. 14 embodiment an inner catheter 1402 may attach laterally to outer catheter 1401 such that the two form concentric shapes. Inner catheter 1402 may be provided with openings 803 to allow light to transfer into and out of inner catheter 1402. Inner catheter 1402 may essentially be a hollow sheath that can accept, orient, and guide an optical catheter 1001 in the manner of optical lumen 903 in FIG. 10. Alternatively, inner catheter 1402 may be a slot, wire frame, track, or rail on the inside of outer catheter 1401, that accepts optical catheter 1001 directly and routes it around the inside of inner catheter 1402 when optical catheter 1001 is pushed. In these embodiments, inner catheter 1402 would not have an outer covering, only a guide track, etc, and the outside of catheter 1001 would be exposed to the outside. In this and other illustrations, openings 803 are shown as discrete windows, but in other embodiments they may be slotted windows to allow more flexibility in viewing locations. Inner catheter 1402 may also be made completely of an optically transparent materials for maximum locational flexibility.

In another embodiment, the positions of inner catheter 1402 and outer catheter 1401 may be reversed such that outer catheter 1401 provides optical openings and inner catheter 1402 provides electrodes.

In another embodiment, a third catheter (not shown) resembling inner catheter 1402 may be placed on the outside of outer catheter 1401. In this three-catheter embodiment, the middle catheter may have openings 803 and the outer two catheters electrodes 802, or vice versa. The different embodiments may be advantageous in creating larger lesions versus having larger viewing area to assess lesions.

In another embodiment, both inner and outer catheters 1402 and 1401 may be provided with both electrodes 802 and openings 803 as in FIG. 8. Here, the operator may select between the two and insert a movable optical catheter 1001 through one or the other, or may insert an optical catheter 1001 in each one simultaneously for multiple location viewing. Alternatively, the catheter 800's shaft may contain a single optical lumen 903, which may be steerable to one or the other catheter 1401 or 1402 at a point near the distal portion, where catheters 1401 and 1402 may form a 'Y' connection.

Figure 15:
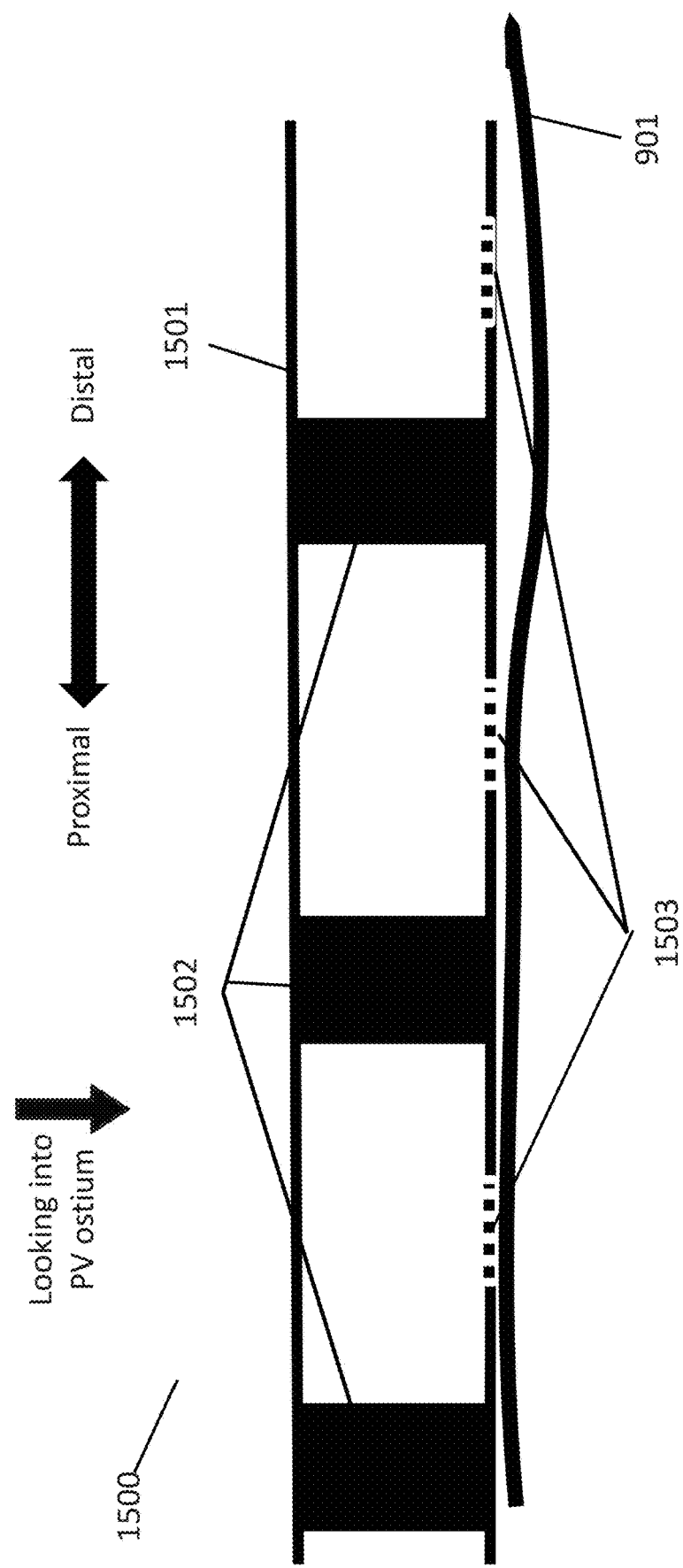
FIG. 15 illustrates a diagram of an example section of a distal end of a PFA-OCR outer catheter, according to embodiments of the present disclosure.

FIG. 15 through FIG. 20 illustrate an alternative embodiment. FIG. 15 illustrates a closeup section of a simplified version of the outer catheter 1500 shown in FIG. 8 and FIG. 9. In this version outer body 1501 may be provided with electrodes 1502 and openings 1503 in the same manner described in FIG. 8 and FIG. 9. As in the previous embodiment, conductive electrodes 1502 may be exposed to the outside of catheter body 1501 and may provide for connection from the inside of body 1501 to wires. However, in this embodiment outer catheter 1501's body may not contain wires or inner lumens to route wire.

Figure 16:
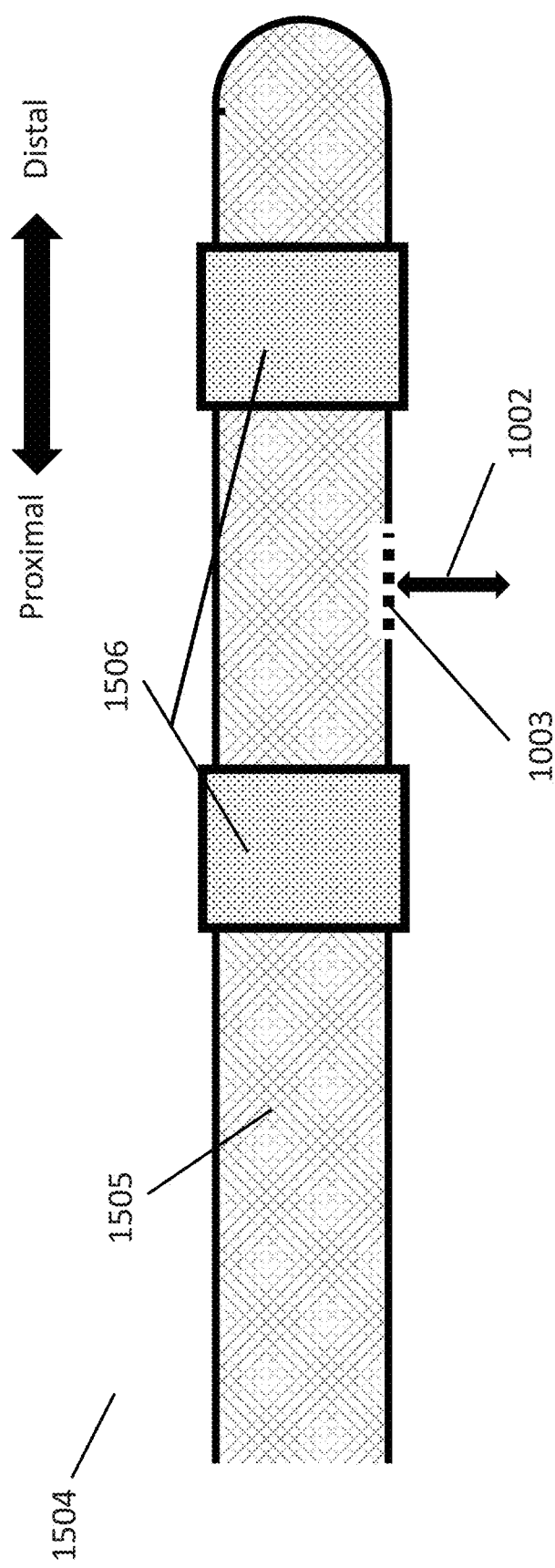
FIG. 16 illustrates a diagram of an example distal end of an inner catheter for translation within an outer catheter of a PFA-OCR catheter system, according to embodiments of the present disclosure.

FIG. 16 is a side view of the distal end of an inner catheter 1504 configured to translate linearly within the outer catheter 1500. Catheter body 1505 is formed of a material that is sufficiently flexible to navigate tortuous anatomy, and sufficiently stiff to be pushed distal and pulled proximal by a control in the catheter 1500 handle (not shown), of the control types previously disclosed. Catheter body 1505 may include a metal braid (not shown) for pushability. At least two conductive electrodes 1506 may be disposed on the outer surface of body 1505, spaced apart at a desired distance for application of PFA energy or for electrical sensing of impedance, cardiac signals, or catheter location. Electrodes 1506 may connect to the inner portion of catheter body 1505 for connection to wires and may be similar to electrodes 802 from FIG. 8 and FIG. 9. At least one opening 1003 is disposed between electrodes 1506 and is similar to openings 803 from FIG. 8 and FIG. 9. It may be a fully open aperture, or it may be covered by an optically transparent material. Optical energy 1002 can pass into and out of opening 1003. It will be obvious to those skilled in the art that the size, number of placement of openings 1003 and electrodes 1506 along body 1505 can vary in different embodiments, allowing design tradeoffs between robustness of functionality against complexity of assembly.

Figure 17:
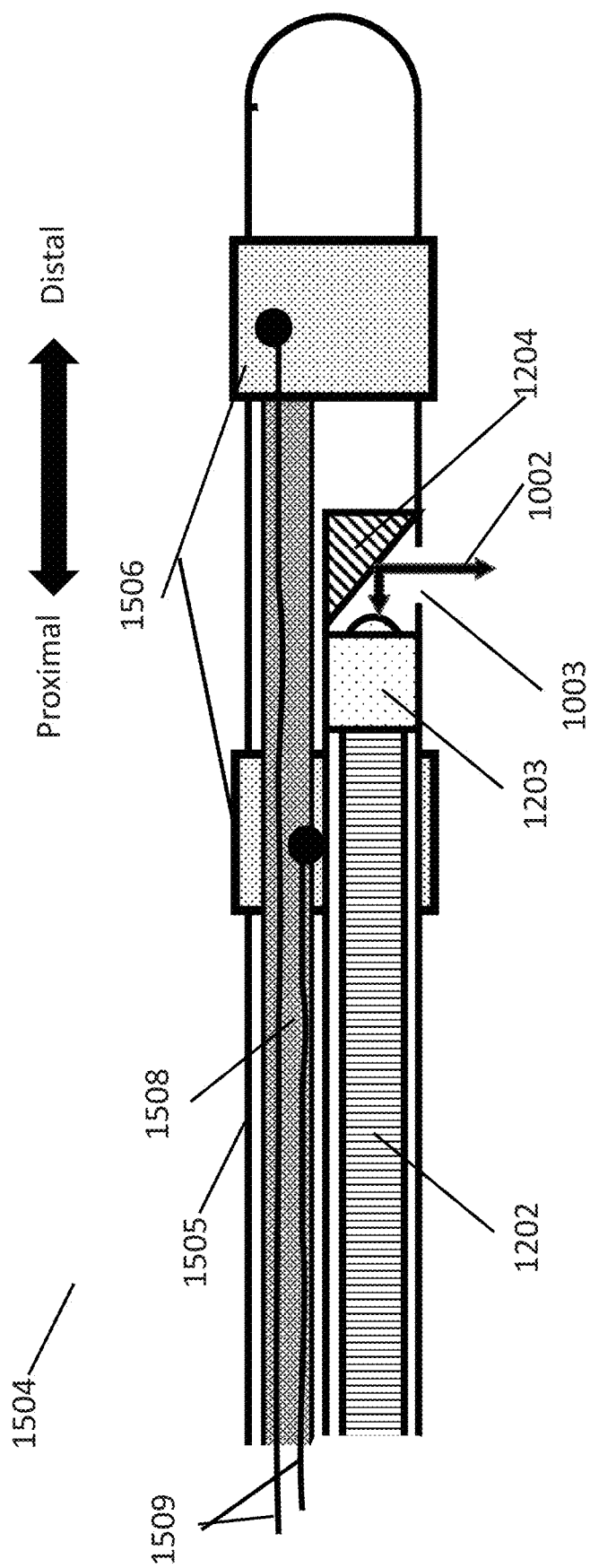
FIG. 17 illustrates a diagram of an example cross-section of a distal end of an inner catheter for translation within an outer catheter of a PFA-OCR catheter system, according to embodiments of the present disclosure.
Figure 18:
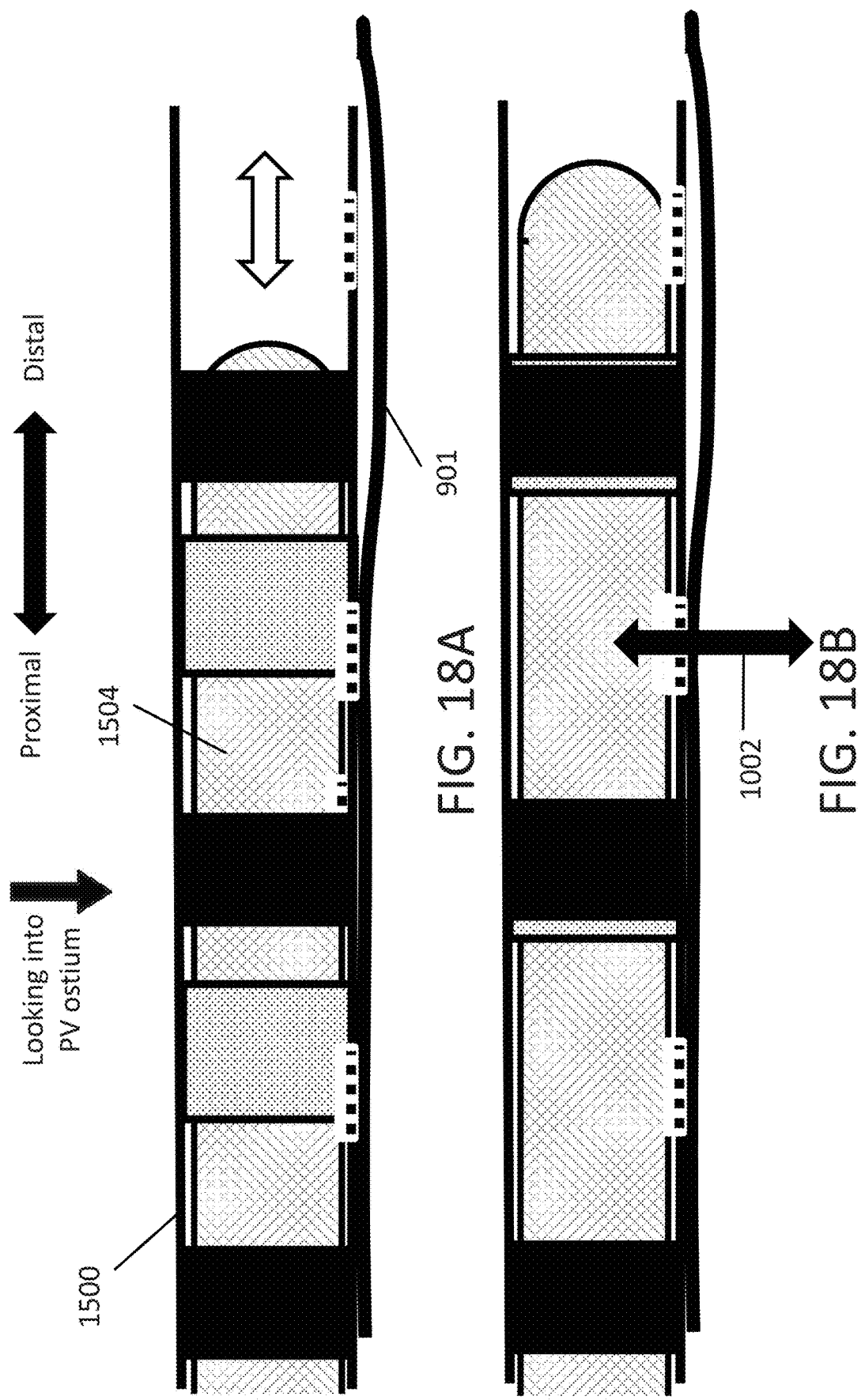
FIGS. 18A-18B illustrate diagrams of example an example distal section of a PFA-OCR catheter system, in which an inner catheter is inserted into an outer catheter, according to embodiments of the present disclosure.

FIG. 17 illustrates a cross-section side view of inner catheter 1504, showing internal components. Body 1505 contains wire lumen 1508, which may extend partially or fully down the length of inner catheter 1504. Wire lumen 1508 contains wires 1509, at least one per electrode 1506. As in FIG. 8 and FIG. 9, wires may be connected to electrodes by various means previously described, depicted in FIG. 17 as black circles at the terminus of each wire 1509. Body 1505 may also contain a set of optical components rigidly fixed to body 1505. These components may include lens 1203 and turning mirror 1204, as shown in FIG. 12. The rigidly fixed optical components may communicate optical energy 1002 between inner catheter 1504 and the outside through opening 1003, as previously described. Optical fiber 1202 may connect to lens 1203 as previously described and may guide optical energy in both directions through the length of inner catheter 1504.

It will be obvious to those skilled in the art that other arrangements and types of optical components are possible, including that depicted in FIG. 13 and elsewhere in this specification. Additionally, the separate wire lumen 1508 shown in FIG. 17 may be partially or fully omitted, and the entire volume within body 1505 may be used to contain wires 1509 and optical fiber or fibers 1202 for some or all of the length of inner catheter 1504.

FIGS. 18A and 18B illustrate diagrams showing translation of inner catheter 1504 when placed within outer catheter 1500. In FIG. 18A, inner catheter 1504 is shown at a location where its two electrodes 1506 are not aligned with outer catheter 1500's electrodes 1502, and consequently inner catheter 1500 openings 1003 are also misaligned with outer catheter openings 1503. As there is no electrical connection between inner and outer electrodes, no electrical functionality (stimulus or sensing) is possible. Likewise, because the inner and outer openings are misaligned, optical energy 1002 cannot transfer between the catheter system and endocardium tissue 901. Translating inner catheter 1504 distally causes inner electrodes 1506 to align with outer electrodes 1502, as shown in FIG. 18B, allowing full electrical and optical functionality to the catheter system by completing the electrical circuit the optical path between tissue 901 and the console (not shown).

Alignment or misalignment of electrodes and windows, as well as contact with the endocardial wall, can be detected by the PFA-OCR system by measuring electrical impedance between the inner electrodes 1506 using circuitry in the console or the catheter. Misaligned catheters will register high impedance. Aligned catheters with good endocardial contact will indicate the impedance of the endocardial wall, typically tens to hundreds of ohms. Likewise, the OCR system may be used to detect alignment between an inner opening 1003 and an outer opening 1503, as optical energy 1002 reflected from the inner wall of outer catheter body 1501 will typically provide a measurably different reflection than optical energy 1002 reflected from endocardial tissue 901.

As discussed relative to other embodiments, means for inserting inner catheter 1504 into outer catheter 1500 may be provided at the proximal end in a handle, and the handle may provide various controls for precise translation of inner catheter 1504 relative to outer catheter 1500. The system may also provide displays to indicate relative catheter locations, positions, and alignment status. As with other embodiments, inner catheter 1504 may be pre-loaded the full length of outer catheter 1500. Alternatively, inner catheter 1504 may be introduced into outer catheter 1500 later in the procedure after catheter 1500 is introduced into the target anatomy. Partial pre-loading is also possible.

Figure 19:
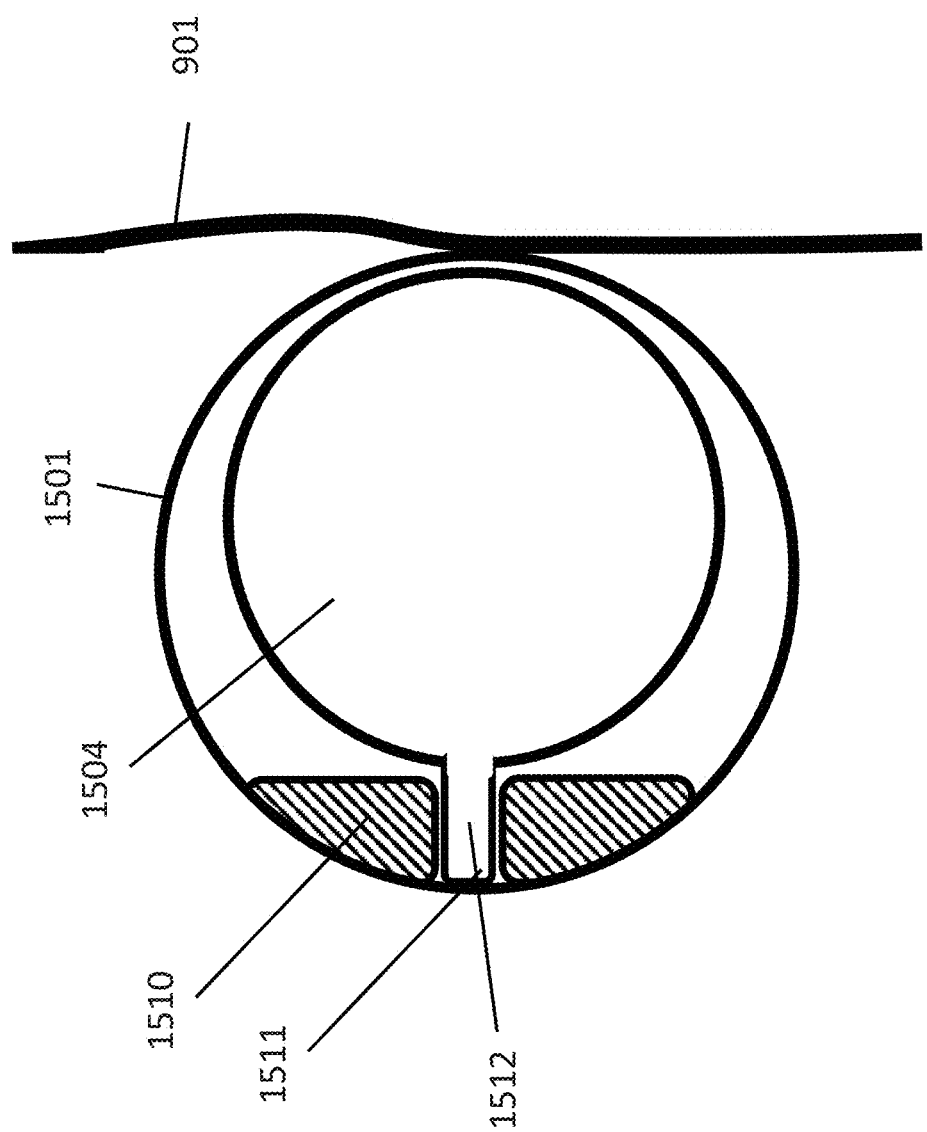
FIG. 19 illustrates a diagram of an example cross-section of inner and outer catheters in a two-catheter system for PFA-OCR, according to embodiments of the present disclosure.

FIG. 19 is a cross section of the catheter system embodiment comprising outer catheter 1500 and inner catheter 1504, and looking down the length of the catheter as in FIG. 11. Here, inner catheter 1504's outer body 1505 is shown in cross section with its internal components not shown. Outer catheter 1500 body 1501 may provide an internal mechanical structure 1510 that provides a groove 1511 or similar guide feature down the length of the catheter. Groove 1511 may interface with a tongue 1512 or similar feature on inner catheter body 1505, to ensure rotational stability and ensuring proper alignment between inner and outer catheter openings 1003 and 1503 (not shown), similar to the system described in FIG. 11. As in FIG. 11, the internal guides may also ensure that inner catheter body 1505 is oriented to abut the surface of outer catheter body 1501 at the side that will be nearest endocardium 901, bringing the optical components (not shown) within inner catheter 1504 as close as possible to endocardium 901.

Figure 20:
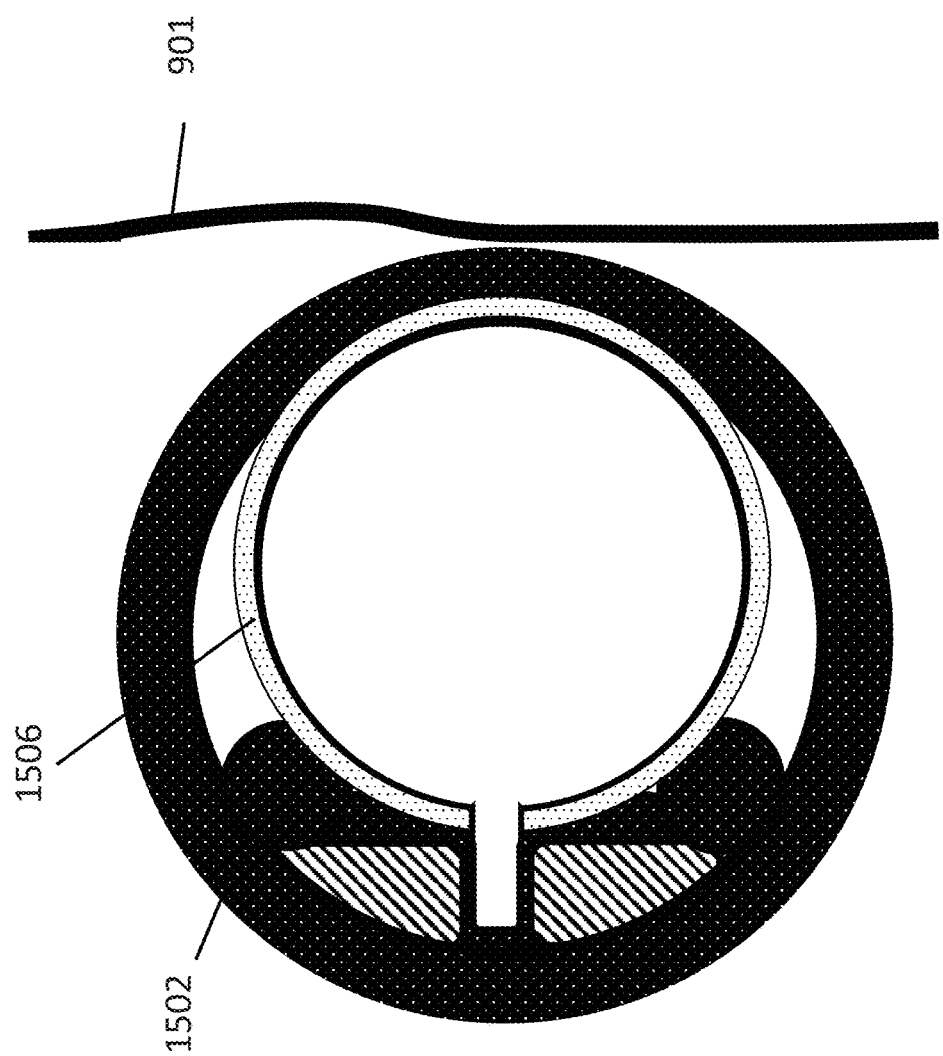
FIG. 20 illustrates a diagram of an example cross-section of inner and outer catheters in a two-catheter system for PFA-OCR, according to embodiments of the present disclosure.

The cross section of FIG. 19 is taken at a point on both inner and outer catheters 1504 and 1500 where no electrodes 1506 or 1502 are disposed. FIG. 20, in contrast, presents the same cross-section but at a location where both inner catheter 1504 and outer catheter 1500 are provided with one of their respective electrodes 1506 or 1502. The outer catheter's electrode 1502, shown in black with white dots, may encircle outer catheter 1500 externally, and penetrate the catheter body 1501 to be disposed internally on the surface of the inner walls on the mechanical guiding structure 1510, or within the groove of 1510. The internal portion of electrode 1502 may be thicker in areas near the guiding structure 1510 as shown on the left of the figure. The inner catheter 1504's electrode 1506 may encircle the outer surface of inner catheter 1504, and may penetrate into the interior of catheter 1504 to connect to its wire (interior penetration and wire not shown). Both electrodes 1502 and 1506 may be arranged such that they will provide good electrical contact when aligned, but will also allow full translational motion of inner catheter 1500 proximally and distally through the electrode. Those skilled in the art will recognize various means by which to accomplish this, with careful design of material selection, placement, and thickness. The wall of outer catheter 1500 may be designed to deform slightly when electrodes are in contact, providing elastic energy to press the metal together and ensure low resistance contact without stressing non-contact regions of the catheters and without inhibiting further translation. The slightly tight fit between contacting electrodes may also provide haptic feedback to the catheter system operator indicating when electrodes are aligned.

In another embodiment, outer catheter 1500 may not include electrodes 1502 as shown in FIG. 15. Here outer catheter body 1501 is a simple tube but may be provided with apertures disposed along its length in line with the optical openings 1503. The electrodes 1506 on inner catheter 1504 (FIG. 16) may be sized to deform flexible outer catheter 1500 when misaligned with the apertures, but when an electrode 1506 is aligned with an aperture, the electrode 1506 will protrude through the aperture a sufficient distance to ensure low ohmic contact with endocardium 901. Inner electrodes 1506 may be formed with a thicker region, or protruding cam, on the side of inner catheter 1504 that is aligned to the apertures (the right side of 1506 in FIG. 20, protruding cam not shown in the figure).

In some embodiments, the openings or apertures may take the form of discrete openings, or may be elongated slots that cover more area, allowing a design tradeoff between precise location and coverage of distance.

In yet another embodiment, the outer catheter 1500 may not be a full tube, but may be a rigid guide rail structure that assumes the same circular shape as FIG. 8 or a different circular or polygonal shape formed into a plane that is parallel to the endocardial wall. Inner catheter 1504 may feature both electrodes and optics as shown in FIG. 16, but may be provided with a mechanical means to attach to the guide rail structure. The guide rail structure may permit electrodes 1506 to contact endocardial surface 901 and may locate opening 1003 sufficiently near to surface 901 to effectively probe it optically, typically at a distance of about less than 500 µm. The guide rail structure may take the form of a wire frame, with longitudinal wires connected at intervals by circular or semi-circular support wires. The guard rail structure may also be a single rail with a tongue-and-groove or similar attachment feature, or a full tube with a wide slot or slots running longitudinally down the side that faces endocardium 901. In another embodiment, the guide rail structure may take the form of a single thick and rigid or semi-rigid wire that provides the appropriate rounded shape. Inner catheter 1504 may include a lumen external or internal to its main shaft to connect to the large wire.

As discussed previously, the openings 1003 and 1503 in the various embodiments may be fully open apertures or may be covered by a material that is optically transparent to the wavelengths used by the system. If open apertures are used, it may be necessary to provide a means to prevent blood or other optically opaque material from blocking the optical energy pathway 1002. Irrigation of the catheter system with a biocompatible optically transparent liquid, such as saline solution, may be used for thermal control and preventing buildup of tissue on the tips of RF ablation systems. The previously disclosed catheter systems may include an irrigation port at their proximal end to allow forced irrigation of the openings 1003 or 1503 to keep them optically clear, or to prevent backflow of blood into the catheter system. The irrigation fluid medium may be medical grade saline solution, or any liquid that is biocompatible and optically transparent. It may be desirable to formulate solutions that include index matching liquid or other materials to improve optical transmission or fluid properties such as viscosity or lubricity. In place of liquid, viscous gel may be added to the spaces behind the openings and remain there to keep the optical path clear.

Figure 21:
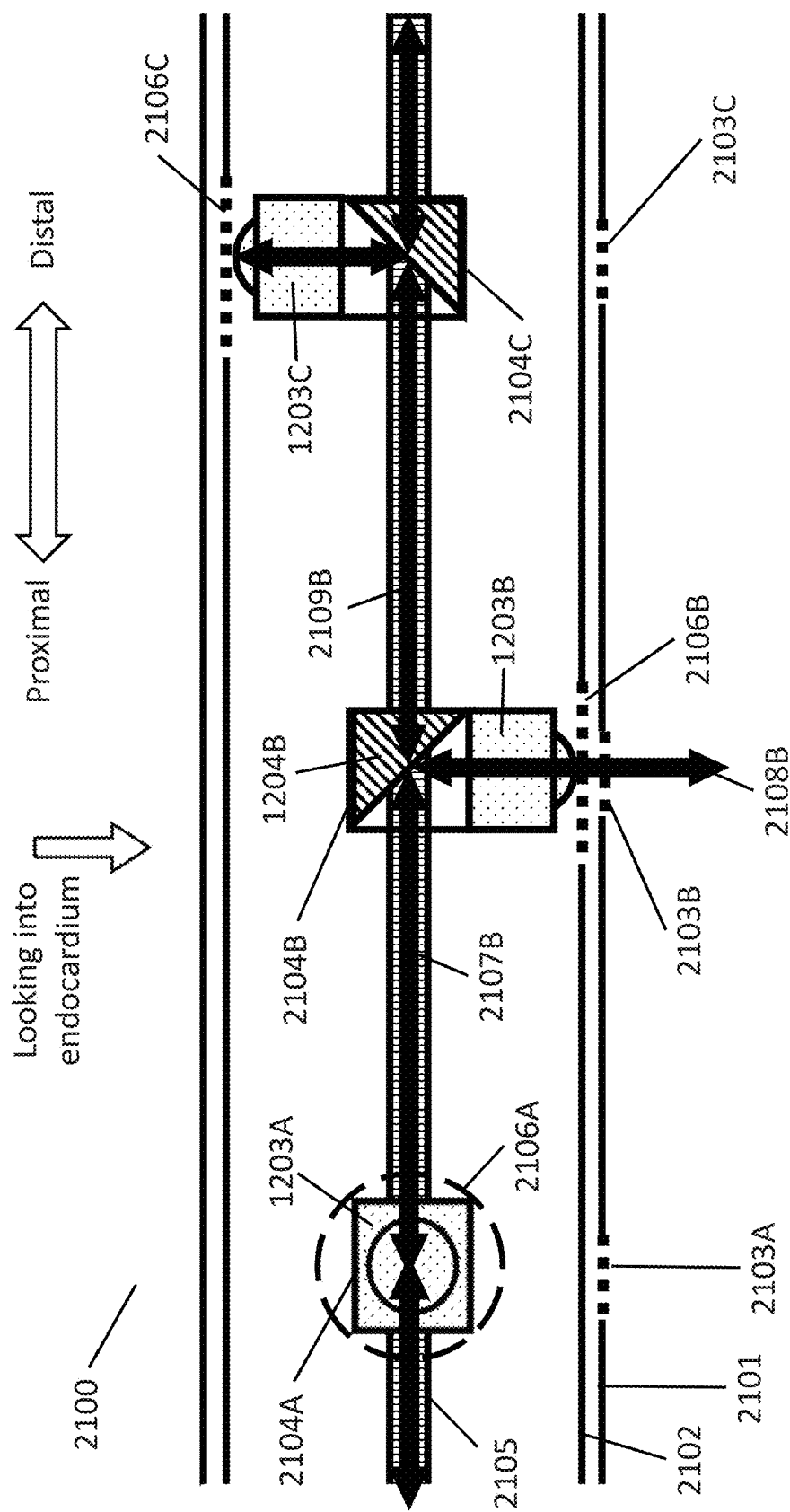
FIG. 21 illustrates a diagram of an example cross-section of a side view of a distal section of a PFA-OCR catheter system, in which a movable optical catheter is configured to rotate within a stationary outer catheter, according to embodiments of the present disclosure.

In another embodiment, a moving catheter is coupled to a relatively stationary catheter as in previous embodiments, but in this case the relative motion may be rotational rather than translational. FIG. 21 illustrates a cross-section view of a distal portion of a PFA-OCR catheter 2100, with the catheter's longitudinal axis running left to right on the page. This may be a two-catheter system, wherein inner optical catheter 2102 may reside within outer catheter 2101. Optical openings 2103 may be disposed along outer catheter 2101 along the side that contacts the endocardium (not shown, bottom of figure) as in previously described embodiments. Inside inner optical catheter 2102 may be a plurality of optical tap assemblies 2104, and running lengthwise through the optical tap assemblies 2104 may be optical fiber 2105. Throughout the figure, optical energy is symbolized by a two-sided solid dark arrow. Each optical tap assembly 2104 may be configured to tap a portion of the optical energy flowing into it from the laser source in the console (not shown) and through fiber 2105, and may transmit the tapped portion to a micro-lens 1203 for focusing and transmission through an inner catheter 2101 opening 2106. The untapped portion of the incoming optical energy may continue on through the fiber to the next optical assembly 2104. For example, optical energy from the console laser source may travel from left to right (proximal to distal) along fiber 2105. When input optical energy 2107B enters optical assembly 2104B, it may encounter semi-reflective turning mirror 1204B. This mirror may be manufactured with a partially reflective coating, causing a portion of the input energy 2108B to be reflected at a predetermined angle (90 degrees in the example figure), and the remainder of the input energy 2109B may be transmitted through mirror 1204B and further towards distal through fiber 2105. The tapped optical energy 2108B may be focused by lens 1203B and may project through inner catheter opening 2106B. Inner catheter 2102 may be configured to rotate about its longitudinal axis (left to right in the figure), while outer catheter 2102 may be configured to remain stationary. In the exemplary figure, inner catheter 2102 is rotated relative to outer catheter 2101 such that openings 2106B and 2103B align, allowing the optical energy 2108B to leave the catheters and enter the endocardium (not shown). The projected light 2108B then reflects from the endocardial or other tissue, and travels back in reverse along the same path by which it entered, to be coupled back to fiber 2105 and carried to the console for signal acquisition and measurement.

Figure 22:
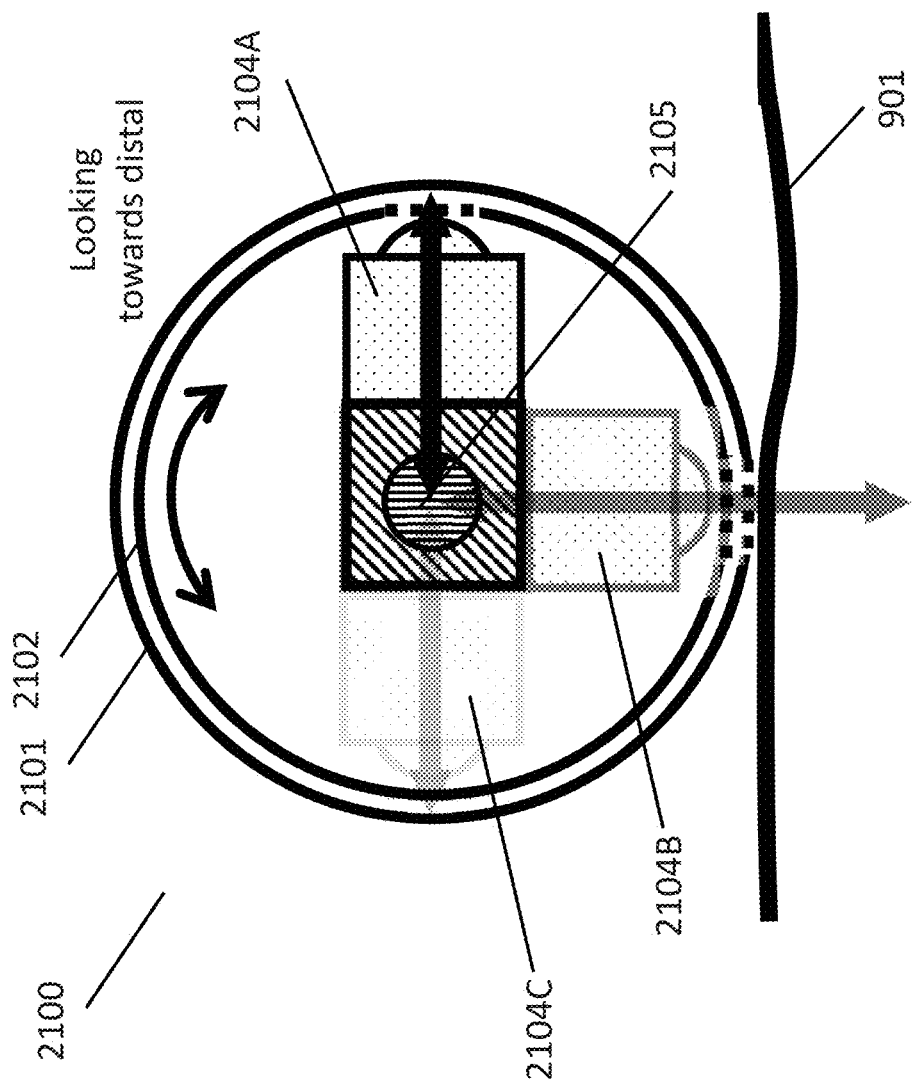
FIG. 22 illustrates a diagram of an example cross-section view of a two-catheter PFA-OCR system that allows selection of an active measurement location by rotation of one catheter relative to the other, according to embodiments of the present disclosure.

Optical assemblies 2104 are oriented about the longitudinal axis of inner catheter 2102, each at a unique angle, as shown in FIGS. 21 and 22. In the figures, the three optical assemblies 2104 are oriented at 90 degrees relative to one another. In FIG. 21 optical assembly 2104A, including opening 2106A, is shown with its lens and tapped optical energy facing out of the page, assembly 2104B including opening 2106B is oriented to send tapped optical energy 2108B downward, and optical assembly 2104C including opening 2106C is oriented to send its tapped optical energy upward. All items within inner catheter 2102 may be fixed relative to the catheter and may rotate together when an operator rotates inner catheter 2102 from a control at the catheter's proximal end. Optical assemblies 2104 and inner catheter openings 2106 may be oriented such that at most only one optical assembly's opening 2106 aligns with an outer catheter opening 2103 at any given time. Since all optical assemblies 2104 may be permanently fixed to fiber 2105, they may all pass optical energy 2108 simultaneously when energy is applied by the console. Optical assemblies 2104 whose openings 2106 do not align with an outer window 2103 may project optical energy 2108 into an inner wall of outer catheter 2101. The inner wall of outer catheter 2101 may made from or coated with a non-reflective material that absorbs light at the wavelength used by the system, ensuring that little or no optical energy will reflect back into the fiber 2105.

FIG. 22 provides a cross-sectional view of the two-catheter system 2100, looking towards the distal end of the catheter section shown in FIG. 21. Optical assemblies 2104 are shown with 2104A shaded darkest to indicate it is most proximal to the viewer, 2104B shaded lighter to indicate it is more distal than 2104A, and 2104C shaded lightest of all to indicate it is the most distal. This view clarifies the concept of rotational selection of the active optical measurement opening by the user.

Although partially reflecting turning mirrors are shown in FIGS. 21 and 22, the tapping of optical energy from fiber 2105 and re-combining of returning energy back into fiber 2105 may also be accomplished by other means. These include optical splitter/coupler devices, which can be designed to couple or split a desired portion of the total optical energy to/from the tap port. They may also include passive devices such as gratings or prisms to redirect light at different wavelengths to different spatial directions, used in combination with multi-wavelength or broadband light.

Obviously, additional optical assemblies 2104 may be disposed at different angles to allow more viewports in the catheter system 2100 as desired. While FIG. 21 and FIG. 22 do not show electrodes, it will be obvious that electrodes and wires may be added in a manner analogous or similar to those in the embodiments previously disclosed. For example, the cross-section of FIG. 22 may be modified to make outer catheter 2101 larger in diameter, in order to accommodate electrode wires as in the previous embodiments, either in a dedicated lumen or in the main lumen of 2101. Additionally, a rotating electrode selective switch analogous to the optical one depicted in FIG. 21 and FIG. 22 can easily be visualized, with a cam or other protruding inner electrode disposed in inner catheter 2102 that protrudes through an opening or otherwise contacts an outer stationary electrode only when a certain rotation angle is selected that causes the inner and outer electrodes to align. Rotationally aligning electrode and optical assemblies may be combined together within catheter 2101 so that both are engaged simultaneously when desired, similar to their previously described translational analogs. Any combination of multi- and single-fiber or wire combinations may be designed to meet specific user needs and manufacturing limitations.

The rotationally selectable two-catheter system described may be locked such that the inner catheter 2102 cannot translate within outer catheter 2101. Rotatable Inner catheter 2102 may be permanently fixed to the distal end of 2101 by any of a number of mechanical means. However, it will be apparent from this disclosure that a combinatory embodiments of the system that allow both translational and rotational motion of one catheter relative to the other are possible and may be employed for certain designs.

In other embodiments, the distal end of the PFA-OCR catheter may have a plurality of separate branches that do not form a continuous loop. The present disclosure's general principles are compatible with such multi-loop architectures. One may simply provide a separate parallel system for each branch within the same overall catheter system. Alternatively, one may create parallel branches of the stationary portion of the system, corresponding for example to fixed outer catheter body 800 in FIG. 9 or 1500 in FIG. 15. The parallel branches may come together at an intersection just proximal to the most proximal opening or electrode. A single movable inner catheter 1001 in FIG. 10 or 1504 in FIG. 16 may then be inserted up to the point of the intersection. Mechanical guide features may facilitate steering the movable inner catheter to the desired branch.

In other embodiments, the PFA-OCR catheter system of the present disclosure may be used with a distal end in the form of a three-dimensional basket, possibly shaped by a balloon device. In some embodiments, the basket may employ loops or branches, as described above.

The exemplary embodiments depicted in the figures show a single optical assembly (fiber, lens, etc) in the translatable inner catheter. In other embodiments, multiple fiber-lens assemblies may comprise the optical portion of the system and may be stationary and fixed to the body of either the movable or the stationary catheter. Multiple instances of an optical assembly of the type exemplified in FIG. 12 or FIG. 13 may be disposed in a single catheter. In one embodiment, multiple fibers may extend down the length of the catheter to at least one proximal optical connector. In another embodiment, a single optical fiber extends through most of the catheter length, but at a location near the distal end, the single fiber fans out to multiple fibers via an optical multiplexor, each downstream fiber connected at least one separate optical channel. Optical multiplexing/demultiplexing may be accomplished by arrangements of many micro-optical components, including: (i) wavelength division multiplexing using diffraction gratings, prisms to divert light spatially; (ii) beam steering using movable micro-mirrors; (iii) polarization division multiplexing using polarizing filters; (iv) tunable wavelength filters, including acousto-optic tunable filters; (v) liquid crystal switch devices. In some embodiments, the optical multiplexing and switching may be performed by a single multiplexing device proximal to the optical openings 1003, 1503 that fans out from one optical fiber to a plurality of fibers. Other embodiments may take the form of a single fiber that is tapped at each desired optical sensing location; the tapped optical energy 1002 may be routed to a short fiber/lens assembly through an optical switch. Taps may take the form of optical couplers/splitters, or partially reflective mirror arrangements. The individual optical pass/block switches may be implemented as wavelength filters, polarization filters, liquid crystal switches, acousto-optic switches, or other devices. Electronics control lines for embodiments that use such switches would be routed back to the electrical connector on the handle.

Just as the optical energy 1002 may be multiplexed to allow a small number of fibers to pass through most of the length of the catheter, electrical energy may be multiplexed to reduce the number of long wires needed to traverse the catheter. In such embodiments, an electronic multiplexor may be provided at a point far distal to the catheter proximal end, but proximal to the most proximal electronic components (electrodes 802, 1502, 1506 or control electronics for an optical multiplexor). Switching control may be augmented by any of myriad digital control methods and may include an integrated circuit. The physical switches may be implemented as micromechanical relays or solid state switches. Electrical switches may also be placed locally near each electrode. In one embodiment, a single wire may contact multiple electrodes, with each electrode having its own localized switch and control electronics, the control electronics opening its switch only when it detects a unique control signal on the single wire that is also used to carry stimulus power or signals. In this embodiment, the unique control signal may be a bit sequence or a unique frequency.

Electrodes may perform stimulus, measurement or monitoring functions as previously described. Electrodes may be configured to perform multiple functions or be dedicated to a single function. In one embodiment, different electrodes are configured to simultaneously stimulate and measure electrogram functionality. Electrodes may also monitor the patient's electrocardiogram (ECG) function and may inhibit PFA stimulus during portions of the ECG cycle during which external electrical stimulation may cause fibrillation or other unwanted reactions. An example of such a PFA stimulus inhibition system may include using one or more electrodes to monitor ECG, processing the signals to determine when the 'T' portion of the ECG cycle occurs, and inhibiting stimulus during the 'T' portion of the cycle. The system may delay the application of the stimulus until the next safe portion of the ECG cycle occurs, for example after the 'T' wave has ended. Signal processing may occur in the console, or may be carried out by electronics within the catheter. It may include measuring a well-defined event in the cardiac cycle, such as descent of the 'R' wave, and then inhibiting stimulus for a physiologically reasonable period after the 'R' wave. The length of the inhibition period may be the same for all cardiac cycles, or it may vary automatically based on recent measurements of heart rate or other parameters.

In other embodiments of the present disclosure, the catheter system may be configured to perform RF ablation (RFA) as well as PFA. The system may have uniquely placed electrodes for RFA functionality, and others for PFA functionality. Alternatively the same electrodes may be used for both PFA and RFA at discrete times by switching different electrical stimuli (PFA or RFA) into the desired electrodes using circuitry in the console. When used in RFA mode, a dispersive pad may be placed on the patient's back to disperse the RF current and provide a return path. In this case, only one of the present disclosure's electrodes may be energized with RF energy at a time. If desired, RFA may also be applied across two of the system's electrodes. The user may be provided with a control on the catheter or at the console to toggle the system between PFA and RFA mode. The optical system may measure and display the same optical parameters for both modes, or may be configured to measure and display unique parameters for each mode. Irrigation holes and channels may be provided on or near electrodes intended for RFA.

In other embodiments, the present disclosure may be modified to effect cryogenic ablation. In one embodiment, the catheter may have a balloon affixed to its distal end configured to fill with a cryogenic liquid such as liquid nitrogen provided by the console or other external device. The internal and external catheters of the present disclosure may be configured to surround the balloon in a continuous series pattern, or as a plurality of parallel distal sections that can be selected as previously described.

In RF, cryogenic, or PFA embodiments, this disclosure has the feature of flexibility of placement of optical viewing locations relative to ablation stimulus (electrical or cryogenic) locations. That is, a designer may select viewing locations around the created lesion that will be of most interest in assessing the lesion quality.

In some embodiments, a means may be provided to adjust the shape of the distal portion of the catheter of the present disclosure. This may include a pull wire or push rod controlled by the user. The adjustment means may be used to increase or decrease the diameter of the circular or size of the polygonal shape at the distal end of the catheter system.

Although cross-sections of the present disclosure shown in FIGS. 11, 19, 20, and 22, depict a circular cross-section, other geometries for the distal section may be advantageous. A half-circle, with the flat side facing the endocardium 901, may have the advantage of covering more area of the endocardial wall with each electrode, providing better electrical contact. It may also reduce distance between the optical openings and the endocardium to allow deeper penetration of the optical energy into the endocardial tissue.

In another embodiment, the outer catheter in various disclosed embodiments may be rotatable by the user to better position the outer catheter openings or electrodes to interface with the endocardium.

In other embodiments, various features may be added to the present disclosure to improve contact between the outer catheter openings and electrodes and the endocardial wall. They may include: a balloon or other mechanical structure to press the catheter distal sections to the wall; a slightly roughened or abrasive surface to reduce slipping.

The description of the present disclosure uses exemplary embodiments from cardiac pulse field and RF ablations, specifically ablations of endocardial tissue near the pulmonary vein ostium. However, the principles of the disclosure may apply to other anatomical structures where tissue ablation may have clinical value. These include but are not limited to: cancerous or pre-cancerous tumors; skin cells; nerve tissue for procedures such as renal denervation; other nerve cells; brain cells; or mucous or other congestive material that may cause, for example, pulmonary edema.

Additional Example Embodiments

Example Embodiment Set #1

Embodiment 1: A system for ablating tissue in a cardiac wall, said system comprising:
a catheter configured to be placed in an outer sheath such that its distal end is in a straight configuration compatible with vascular delivery, said distal end assuming a circular shape when pushed through said sheath, said circular shape in a plane parallel to said cardiac wall and configured to contact said cardiac wall;
a plurality of electrodes disposed on said distal end at a distance from one another, said electrodes connected by wire to an external electrical energy generating device via an electrical connector on the proximal end of said catheter, said electrodes configured to deliver electrical energy to said cardiac wall when energized by said electrical generating device;
at least one optical port, said port comprising optical components connected by an optical fiber to an external optical energy generating device via an optical connector on the proximal end of said catheter, said optical components configured to project optical energy into said cardiac wall when energized by said optical generating device, and to receive reflected optical energy back from said cardiac wall and transfer said reflected energy through said fiber and said optical connector to an external optical sensing device;
said at least one optical port positioned on said distal end of said catheter at a location relative to said electrodes, said location chosen for optimal measurement of optical parameter changes caused by tissue ablation by said energization of said electrodes.

Embodiment 2: The system of embodiment 1 wherein the side of said catheter configured to contact said cardiac wall is flattened to create a semi-circular cross section of said catheter, said flattened side maximizing contact area of said side with said cardiac wall.

Embodiment 3: The system of embodiment 1 wherein said circular shape is an ovular shape, a polygonal shape, or a combination of ovular and polygonal shapes.

Embodiment 4: The system of embodiment 1 wherein at least two electrodes within said plurality of electrodes are connected to dedicated wires, said plurality of dedicated wires connected to a multiplexor located proximal to said electrodes, said multiplexor configured to selectively switch between said dedicated electrode wires and at least one proximal wire, said proximal wire extending from said multiplexor to a connector on said proximal end of said catheter.

Embodiment 5: The system of embodiment 1 wherein a subset of said plurality of electrodes are wired together to form a single electrical node.

Embodiment 6: The system of embodiment 1 comprising a plurality of said optical ports, and further comprising an optical multiplexor located proximal to said optical ports, said optical multiplexor configured to selectively switch between a plurality of optical fibers, each said fiber dedicated to one of said optical ports, and at least one proximal fiber, said proximal fiber extending from said multiplexor to a connector on said proximal end of said catheter.

Embodiment 7: The system of embodiment 1 wherein said optical components are selected from: focusing lens, turning mirror, diffraction grating, GRIN lens, optical tap, optical coupler, optical polarizer.

Embodiment 8: The system of embodiment 1 wherein said electrical energy delivered to said cardiac wall by said plurality of electrodes is configured to ablate tissue in the cardiac wall by at least one process selected from the following: radiofrequency ablation, thermal ablation, pulse field ablation, or irreversible electroporation.

Embodiment 9: The system of embodiment 8 wherein a system operator may select the type of said electrical energy delivered by controls on said external electrical energy device.

Embodiment 10: The system of embodiment 1 wherein said external optical energy generating device, said at least one optical port, and said external optical sensing device are configured to perform said optical measurement of optical parameter changes by at least one process selected from the following: optical coherence tomography, optical coherence reflectometry, low coherence interferometry, degree of polarization uniformity measurement, polarization sensitive optical coherence tomography, reflection intensity, spectroscopy, Raman spectroscopy, and near infrared spectroscopy.

Embodiment 11: The system of embodiment 10 wherein said optical measurement may be processed and displayed by an external device to indicate at least one of: contact stability between said optical port and said cardiac wall, tissue viability, tissue type, tissue depth, tissue composition.

Embodiment 12: The system of embodiment 11 wherein said processed and displayed optical measurement provides data for a depth of at least 1 millimeter into the tissue being measured.

Embodiment 13: The system of embodiment 11 wherein said external device includes an algorithm for calculated and displaying estimated depth of a lesion.

Embodiment 14: The system of embodiment 10 wherein said system measures birefringence of tissue in said cardiac wall.

Embodiment 15: The system of embodiment 1 wherein said location chosen for optimal measurement of optical parameter changes is at a midpoint between two electrodes configured to serve as positive and negative nodes for pulse field ablation stimulus.

Embodiment 16: The system of embodiment 1 wherein at least one of said electrodes is configured to perform multiple functions when connected to at least one external device via said electrical connector on said proximal end of said catheter, said functions selected from the following: electrical stimulus, electrogram measurement, electrocardiogram measurement, tissue impedance measurement.

Embodiment 17: The system of embodiment 1 wherein said measurement of said optical parameter is taken before, during, or after said delivery of said electrical energy, in order to assess the effects of said delivery.

Embodiment 18: The system of embodiment 1 wherein distal end comprises a plurality of several distal ends, each distal end provided with its own electrodes and optical ports and configured in a parallel shape comprising multiple lines, circular shapes, or polygons.

Embodiment 19: The system of embodiment 18 wherein said plurality of distal ends are configured in a three dimensional spheroidal shape.

Example Embodiment Set #2

Embodiment 20: A system for ablating tissue in a cardiac wall, said system comprising:

a first catheter configured to be placed in an outer sheath such that its distal end is in a straight configuration compatible with vascular delivery, said distal end assuming a circular shape when pushed through said sheath, said circular shape in a plane parallel to said cardiac wall and configured to contact said cardiac wall;

a second catheter configured to connect to said first catheter longitudinally, and to translate distally or proximally along said first catheter;

said second catheter further comprising a plurality of electrodes disposed on said second catheter's distal end at a distance from one another, said electrodes connected by wire to an external electrical energy generating device via an electrical connector on the proximal end of said second catheter, said electrodes configured to deliver electrical energy to said cardiac wall when energized by said electrical generating device;

said second catheter further comprising at least one optical port, said port comprising optical components connected by an optical fiber to an external optical energy generating device via an optical connector on the proximal end of said second catheter, said optical components configured to project optical energy into said cardiac wall when energized by said optical generating device, and to receive reflected optical energy back from said cardiac wall and transfer said reflected energy through said fiber and said optical connector to an external optical sensing device;

said at least one optical port positioned on said distal end of said second catheter at a location relative to said electrodes, said location chosen for optimal measurement of optical parameter changes caused by tissue ablation by said energization of said electrodes.

Embodiment 21: The system of embodiment 20 wherein said first catheter is configured to provide a fixed planar path against said cardiac wall, and to remain in place while said second catheter is translated distally or proximally about said path by an operator.

Embodiment 22: The system of embodiment 20 wherein said second catheter connects to said first catheter by means of a lumen disposed on said second catheter, said first catheter configured to fit within said lumen.

Embodiment 23: The system of embodiment 20 wherein said second catheter connects to said first catheter by means of a lumen disposed on said first catheter, said second catheter configured to fit within said lumen.

Embodiment 24: The system of embodiment 20 wherein said first catheter further comprises at least one said electrode connected to said external electrical device or at least one said optical port connected to said external optical device.

Embodiment 25 The system of embodiment 20 wherein at least a portion of the side of said first catheter that faces said cardiac wall is provided with at least one optically transparent opening, said at least one optical port of said second catheter configured to align with said opening when translated to its location.

Embodiment 26: The system of embodiment 20 wherein said second catheter may be rotated about its longitudinal axis with respect to said first catheter.

Embodiment 27: The system of embodiment 20 wherein said second catheter is aligned rotationally within said first catheter to ensure its said optical ports are directed towards said cardiac wall, and further wherein said second catheter includes a means to prohibit rotation about its longitudinal axis relative to said first catheter.

Embodiment 28: The system of embodiment 20, wherein said first and said second catheters are each provided with at least one electrode, said pair of electrodes making electrical contact with one another when said second catheter is translated to a specific location, said electrical contact establishing a connection from an external electrical device to the one of said pair of electrodes that is in contact with said cardiac wall.

Embodiment 29: The system of embodiment 20 wherein said first and said second catheters' longitudinal axes are concentric.

Embodiment 30: The system of embodiment 20 wherein said first and said second catheters' longitudinal axes are separate and parallel.

Embodiment 31: The system of embodiment 20 wherein the side of said second catheter configured to contact said cardiac wall is flattened to create a semi-circular cross section of said catheter, said flattened side configured to maximize contact area of said side with said cardiac wall.

Embodiment 32: The system of embodiment 20 wherein said circular shape is an ovular shape, a polygonal shape, or a combination of ovular and polygonal shapes.

Embodiment 33: The system of embodiment 20 wherein said optical components are selected from: focusing lens, turning mirror, diffraction grating, GRIN lens, optical tap, optical coupler, optical polarizer.

Embodiment 34: The system of embodiment 20 wherein said electrical energy delivered to said cardiac wall by said plurality of electrodes is configured to ablate tissue in the cardiac wall by at least one process selected from the following: radiofrequency ablation, thermal ablation, pulse field ablation, or irreversible electroporation.

Embodiment 35: The system of embodiment 34 wherein a system operator may select the type of said electrical energy delivered by controls on said external electrical energy device.

Embodiment 36: The system of embodiment 20 wherein said external optical energy generating device, said at least one optical port, and said external optical sensing device are configured to perform said optical measurement of optical parameter changes by at least one process selected from the following: optical coherence tomography, optical coherence reflectometry, low coherence interferometry, degree of polarization uniformity measurement, polarization sensitive optical coherence tomography, reflection intensity, spectroscopy, Raman spectroscopy, and near infrared spectroscopy.

Embodiment 37: The system of embodiment 36 wherein said optical measurement may be processed and displayed by an external device to indicate at least one of: contact stability between said optical port and said cardiac wall, tissue viability, tissue type, tissue depth, tissue composition.

Embodiment 38: The system of embodiment 37 wherein said processed and displayed optical measurement provides data for a depth of at least 1 millimeter into the tissue being measured.

Embodiment 39: The system of embodiment 37 wherein said external device includes an algorithm for calculated and displaying estimated depth of a lesion.

Embodiment 40: The system of embodiment 36 wherein said system measures birefringence of tissue in said cardiac wall.

Embodiment 41: The system of embodiment 20 wherein said location chosen for optimal measurement of optical parameter changes is at a midpoint between two electrodes configured to serve as positive and negative nodes for pulse field ablation stimulus.

Embodiment 42: The system of embodiment 20 wherein at least one of said electrodes is configured to perform multiple functions when connected to at least one external device via said electrical connector on said proximal end of said catheter, said functions selected from the following: electrical stimulus, electrogram measurement, electrocardiogram measurement, tissue impedance measurement.

Embodiment 43: The system of embodiment 20 wherein said measurement of said optical parameter is taken before, during, or after said delivery of said electrical energy, in order to assess the effects of said delivery.

Embodiment 44: The system of embodiment 20 wherein said distal end comprises a plurality of several distal ends, each distal end provided with its own electrodes and optical ports and configured in a parallel shape comprising multiple lines, circular shapes, or polygons.

Embodiment 45: The system of embodiment 44 wherein said plurality of distal ends are configured in a three dimensional spheroidal shape.

Embodiment 46: The system of embodiment 44 wherein said second catheter is steerable to select the distal end it will translate into.

Embodiment 47: The system of embodiment 20 in which said second catheter is fully distally translated relative to said first catheter when.

Embodiment 48: The system of embodiment 20 in which said first catheter is inserted into said outer sheath during said vascular delivery without said second catheter, and said second catheter is translated to the distal portion of said first catheter after said first catheter is pushed through said sheath.

Embodiment 49: The system of embodiment 20, wherein said second catheter is fixed to prevent longitudinal translation relative to said first catheter.

Embodiment 50: The system of embodiment 49, wherein said second catheter is configured to selectively rotate relative to said first catheter, and further wherein said optical ports are disposed about the circumference of said second catheter such that no more than one port will directly face said cardiac wall for a given rotation angle.

Embodiment 51: The system of embodiment 20 further comprising a user control configured to facilitate precise movement of said second catheter relative to said first catheter.

Embodiment 52: The system of embodiment 51 wherein said user control is located in one of: a catheter handle of said system, an external device connected to said catheter.

Embodiment 53: The system of embodiment 51 wherein said user control comprises at least one of: motors, stepper motors, a gearing system, a rotational knob, a slider switch, a computer screen and input device, a display indicating precise location.

Example Embodiment Set #3

Embodiment 54: A method for ablating cardiac tissue, said method comprising the steps of:
inserting a sheath containing a first catheter device into a cardiac chamber;
pushing said first catheter device through said sheath, said first catheter configured to assume a planar shape, said plane of said shape being oriented parallel to the cardiac chamber wall;
translating a second catheter longitudinally along said first catheter, said second catheter configured to follow a path defined by said shape of said first catheter, said second catheter further disposed with electrodes configured to sense electrical parameters and deliver electrical energy, said second catheter further disposed with optical ports configured to delivery optical energy to said cardiac wall and transfer reflected optical energy back to externally connected optical measurement devices;
pausing translation of said second catheter at desired locations around said path of said planar shape to deliver electrical energy to selectively ablate cardiac wall tissue;
applying optical energy and measuring reflected energy to assess optical parameters that indicate contact stability, tissue viability, and lesion size and depth;
repeating the steps of distal or proximal translation of said second catheter, while fixing the position of said first catheter, applying electrical stimulation and taking optical measurements as needed to ensure a continuous lesion in the desired locations; and removing said catheter system.

Embodiment 55: The method of embodiment 54, wherein the catheter system comprises any of the catheter systems from embodiments 20-55.

Exemplary Computing Embodiments

Figure 23:
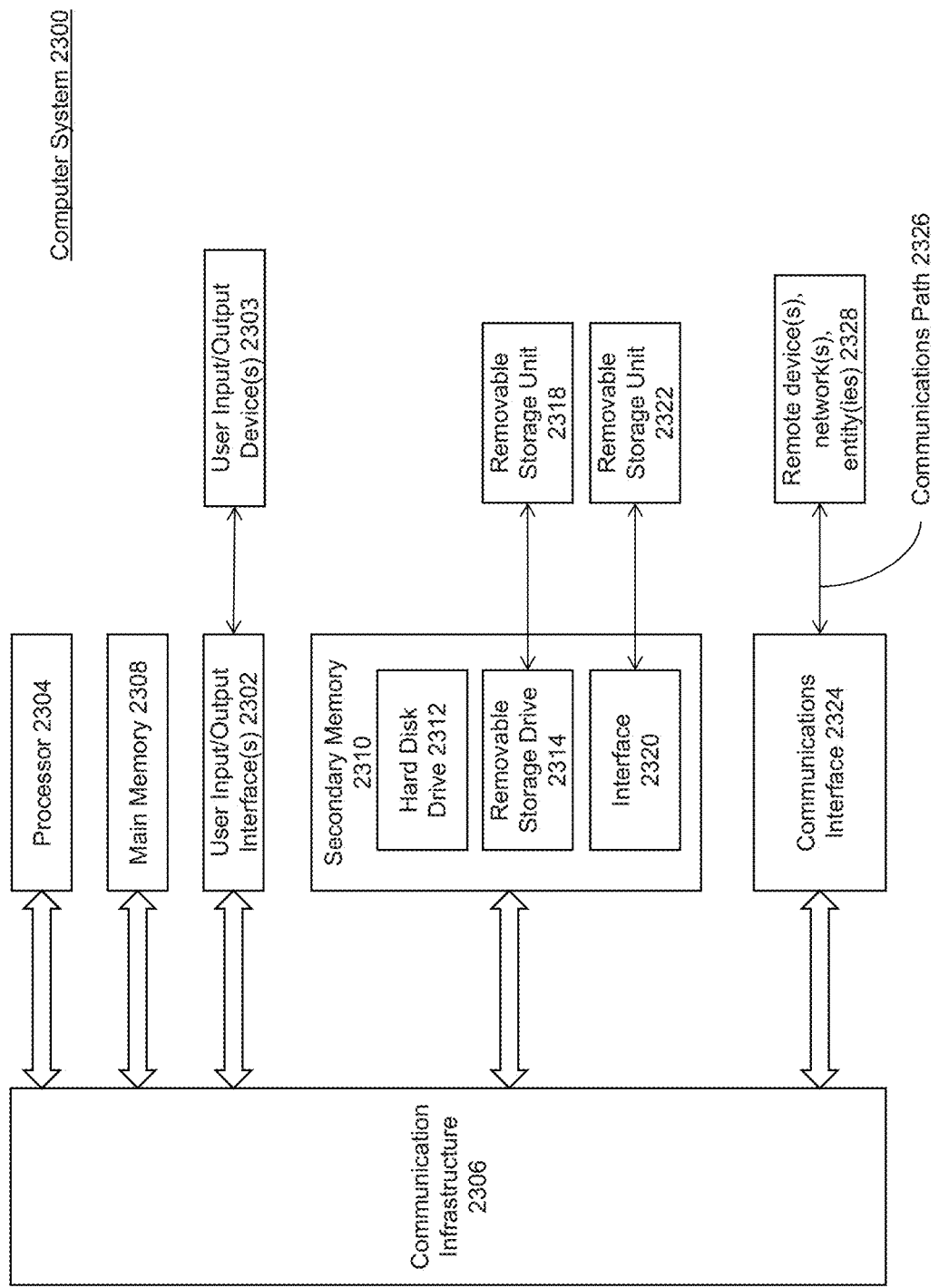
FIG. 23 illustrates a block diagram of example components of a computer system, according to embodiments of the present disclosure.

FIG. 23 is a block diagram of example components of computer system 2300. One or more computer systems 2300 may be used, for example, to implement any of the embodiments discussed herein, as well as combinations and sub-combinations thereof. In some embodiments, one or more computer systems 2300 may be used to implement the methods, computing, and processing devices, as described herein. Computer system 2300 may include one or more processors (also called central processing units, or CPUs), such as a processor 2304. Processor 2304 may be connected to a communication infrastructure or bus 2306.

Computer system 2300 may also include user input/output interface(s) 2302, such as monitors, keyboards, pointing devices, etc., which may communicate with communication infrastructure 2306 through user input/output interface(s) 2303.

One or more of processors 2304 may be a graphics processing unit (GPU). In an embodiment, a GPU may be a processor that is a specialized electronic circuit designed to process mathematically intensive applications. The GPU may have a parallel structure that is efficient for parallel processing of large blocks of data, such as mathematically intensive data common to computer graphics applications, images, videos, etc.

Computer system 2300 may also include a main or primary memory 2308, such as random access memory (RAM). Main memory 2308 may include one or more levels of cache. Main memory 2308 may have stored therein control logic (i.e., computer software) and/or data. In some embodiments, main memory 2308 may include optical logic configured to perform processing and analysis of optical measurements obtained from tissue by a catheter and determine lesion predictions.

Computer system 2300 may also include one or more secondary storage devices or memory 2310. Secondary memory 2310 may include, for example, a hard disk drive 2312 and/or a removable storage drive 2314.

Removable storage drive 2314 may interact with a removable storage unit 2318. Removable storage unit 2318 may include a computer usable or readable storage device having stored thereon computer software (control logic) and/or data. Removable storage unit 2318 may be a program cartridge and cartridge interface (such as that found in video game devices), a removable memory chip (such as an EPROM or PROM) and associated socket, a memory stick and USB port, a memory card and associated memory card slot, and/or any other removable storage unit and associated interface. Removable storage drive 2314 may read from and/or write to removable storage unit 2318.

Secondary memory 2310 may include other means, devices, components, instrumentalities or other approaches for allowing computer programs and/or other instructions and/or data to be accessed by computer system 2300. Such means, devices, components, instrumentalities or other approaches may include, for example, a removable storage unit 2322 and an interface 2320. Examples of the removable storage unit 2322 and the interface 2320 may include a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

Computer system 2300 may further include a communication or network interface 2324. Communication interface 2324 may enable computer system 2300 to communicate and interact with any combination of external devices, external networks, external entities, etc. (individually and collectively referenced by reference number 2328). For example, communication interface 2324 may allow computer system 2300 to communicate with external or remote devices 2328 over communications path 2326, which may be wired and/or wireless (or a combination thereof), and which may include any combination of LANs, WANs, the Internet, etc. Control logic and/or data may be transmitted to and from computer system 2300 via communication path 2326. In some embodiments, computer system 2300 may be coupled to a catheter via a connector and optical and electrical connections at communication interface 2324, including optical fibers and electrical wiring, pins, and/or components.

Computer system 2300 may also be any of a personal digital assistant (PDA), desktop workstation, laptop or notebook computer, netbook, tablet, smartphone, smartwatch or other wearables, appliance, part of the Internet-of-Things, and/or embedded system, to name a few non-limiting examples, or any combination thereof.

Computer system 2300 may be a client or server, accessing or hosting any applications and/or data through any delivery paradigm, including but not limited to remote or distributed cloud computing solutions; local or on-premises software ("on-premise" cloud-based solutions); "as a service" models (e.g., content as a service (CaaS), digital content as a service (DCaaS), software as a service (SaaS), managed software as a service (MSaaS), platform as a service (PaaS), desktop as a service (DaaS), framework as a service (FaaS), backend as a service (BaaS), mobile backend as a service (MBaaS), infrastructure as a service (IaaS), etc.); and/or a hybrid model including any combination of the foregoing examples or other services or delivery paradigms.

Any applicable data structures, file formats, and schemas in computer system 2300 may be derived from standards including but not limited to JavaScript Object Notation (JSON), Extensible Markup Language (XML), Yet Another Markup Language (YAML), Extensible Hypertext Markup Language (XHTML), Wireless Markup Language (WML), MessagePack, XML User Interface Language (XUL), or any other functionally similar representations alone or in combination. Alternatively, proprietary data structures, formats or schemas may be used, either exclusively or in combination with known or open standards.

In some embodiments, a tangible, non-transitory apparatus or article of manufacture comprising a tangible, non-transitory computer useable or readable medium having control logic (software) stored thereon may also be referred to herein as a computer program product or program storage device. This includes, but is not limited to, computer system 2300, main memory 2308, secondary memory 2310, and removable storage units 2318 and 2322, as well as tangible articles of manufacture embodying any combination of the foregoing. Such control logic, when executed by one or more data processing devices (such as computer system 2300), may cause such data processing devices to operate as described herein.

CONCLUSION

It is obvious to those skilled in the art that the clinical ablation procedures described above do not need to include all of the steps as described, and such steps do not need to be in the exact order which has been presented.

It is to be appreciated that the Detailed Description section, and not the Summary and Abstract sections, is intended to be used to interpret the claims. The Summary and Abstract sections may set forth one or more but not all exemplary embodiments of the present disclosure as contemplated by the inventor(s), and thus, are not intended to limit the present disclosure and the appended claims in any way.

Embodiments of the present disclosure have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

Furthermore, the following aspects are disclosed explicitly:

1. A system comprising:
   a catheter comprising:
   a proximal section;
   a distal section;
   a shaft coupled between the proximal section and the distal section; and
   an optical circuit configured to transport light at least partially from the proximal section to the distal section and back;
   a pulsed field ablation energy source coupled to the catheter and configured to transmit pulsed electrical signals to a tissue sample; and
   a processing device configured to:
   analyze one or more optical signals received from the optical circuit to determine changes in polarization or phase retardation of light reflected or scattered by the tissue sample; and determine changes in a birefringence of the tissue sample based on the changes in polarization or phase retardation.

2. The system of aspect 1, wherein the optical circuit is configured to transport light at least partially from the proximal section to the distal section and back using at least partially a polarization maintaining transmission medium in the shaft.

3. The system of aspect 1 or aspect 2, wherein the pulsed electrical signals transmitted by the pulsed field ablation energy source are monophasic or biphasic.

4. The system of one of the preceding aspects, wherein the changes in polarization or phase retardation of the light reflected or scattered by the tissue sample are in response to the pulsed electrical signals transmitted to the tissue sample.

5. The system of one of the preceding aspects, wherein the one or more optical signals comprises an optical coherence tomography (OCT) signal or an optical coherence reflectometry (OCR) signal acquired from the tissue sample.

6. The system of one of the preceding aspects, wherein the optical circuit is configured to transmit the light from the distal section to the tissue sample.

7. The system of one of the preceding aspects, wherein the distal section of the catheter comprises a plurality of optical ports configured to collect the light reflected or scattered from the tissue sample.

8. The system of one of the preceding aspects, wherein characteristics of the pulsed electrical signals are selected by a user of the catheter, wherein the characteristics comprise a frequency, amplitude, and duration of the pulsed electrical signals.

9. A method for performing ablation in a patient, the method comprising:
   inserting a catheter into vasculature of the patient;
   moving a distal end of the catheter to an ablation site in the vasculature of the patient;
   establishing tissue contact at the distal end of the catheter through optical means using light delivered to the ablation site through the distal end of the catheter;
   delivering energy from the distal end of the catheter into the tissue from an energy source coupled to the catheter;
   optically interrogating the ablation tissue site to determine changes in polarization or phase retardation of light delivered to the ablation tissue site through the catheter; and
   removing the catheter from the vasculature.

10. The method of aspect 9, wherein the energy comprises a pulse train, the energy source comprises a pulse field ablation energy source, and the pulse train comprises pulsed electrical signals that are monophasic or biphasic.

11. The method of aspect 10, wherein the changes in polarization or phase retardation of the light are in response to the pulsed electrical signals delivered to the tissue.

12. The method of aspect 11, wherein characteristics of the pulsed electrical signals are selected by a user of the catheter, wherein the characteristics comprise a frequency, amplitude, and duration of the pulsed electrical signals.

13. The method of one of aspects 9 to 12, wherein the energy comprises radiofrequency (RF), and the energy source comprises an RF energy source.

14. The method of one of aspects 9 to 13, wherein the catheter comprises a shaft with a multimode-transmission media disposed in the shaft, wherein the multimode-transmission media is used to enable a use of tissue spectrometry to determine a depth of anatomical structures in the patient.

15. A catheter for ablating tissue in a cardiac wall, the catheter comprising:
   a proximal end;
   a distal end;
   a plurality of electrodes disposed on the distal end at a distance from each other; and
   at least one optical port positioned on the distal end at a location relative to the plurality of electrodes, wherein the catheter is configured to be placed in an outer sheath such that the distal end is in a straight configuration compatible with vascular delivery, the distal end assuming a circular shape when pushed through the sheath, wherein the plurality of electrodes are connected by wire to an external electrical energy generating device via an electrical connector on the proximal end of the catheter, wherein the plurality of electrodes are configured to deliver electrical energy to the cardiac wall when energized by the external electrical energy generating device, wherein the at least one optical port comprises optical components connected by an optical fiber to an external optical energy generating device via an optical connector on the proximal end of the catheter, wherein the optical components are configured to: project optical energy into the cardiac wall when energized by the optical energy generating device, receive reflected optical energy back from the cardiac wall, and transfer the reflected optical energy through the optical fiber and the optical connector to an external optical sensing device, 16. The catheter of aspect 15, wherein the circular shape of the distal end is in a plane parallel to the cardiac wall and configured to contact the cardiac wall.

17. The catheter of aspect 15 or aspect 16, wherein the location of the at least one optical port is chosen for optimal observation of optical parameter changes caused by tissue ablation by energization of the plurality of electrodes.

18. The catheter of one of aspects 15 to 17, wherein the electrical energy delivered by the external electrical energy generating device comprises pulsed electrical signals.

19. The catheter of aspect 18, wherein the pulsed electrical signals are monophasic or biphasic.

20. The catheter of one of aspects 15 to 19, wherein the electrical energy delivered by the external electrical energy generating device comprises radiofrequency (RF) energy.

What is claimed is:

1. A system comprising:
    a catheter comprising:
        a proximal section;
        a distal section;
        a shaft coupled between the proximal section and the distal section; and
        an optical circuit configured to transport light at least partially from the proximal section to the distal section and back;
    a pulsed field ablation energy source coupled to the catheter and configured to transmit pulsed electrical signals to a tissue sample, the pulsed electrical signals causing electroporation of the tissue sample; and
    a processing device configured to:
        after a predetermined period of time, analyze one or more optical signals received from the optical circuit to determine changes in polarization or phase retardation of light reflected or scattered by the tissue sample, the predetermined period of time comprising a length of time needed for a non-thermal lesion to begin forming in the tissue sample, the non-thermal lesion resulting from the electroporation of the tissue sample; and
        determine changes in a birefringence of the tissue sample based on the changes in polarization or phase retardation.

2. The system of claim 1, wherein the optical circuit is configured to transport light at least partially from the proximal section to the distal section and back using at least partially a polarization maintaining transmission medium in the shaft.

3. The system of claim 1, wherein the pulsed electrical signals transmitted by the pulsed field ablation energy source are monophasic or biphasic.

4. The system of claim 1, wherein the changes in polarization or phase retardation of the light reflected or scattered by the tissue sample are in response to the pulsed electrical signals transmitted to the tissue sample.

5. The system of claim 1, wherein the one or more optical signals comprise a polarization-sensitive optical coherence tomography (PS-OCT) signal or a polarization-sensitive optical coherence reflectometry (PS-OCR) signal acquired from the tissue sample.

6. The system of claim 1, wherein the optical circuit is configured to transmit the light from the distal section to the tissue sample.

7. The system of claim 1, wherein the distal section of the catheter comprises a plurality of optical ports configured to collect the light reflected or scattered from the tissue sample.

8. The system of claim 1, wherein characteristics of the pulsed electrical signals are selected by a user of the catheter, wherein the characteristics comprise a frequency, amplitude, and duration of the pulsed electrical signals.

9. The system of claim 1, wherein the pulsed electrical signals transmitted to the tissue sample by the pulsed field ablation energy source comprise a predetermined number of pulses that causes cellular or structural changes in the tissue sample.

10. The system of claim 9, wherein the pulsed field ablation energy source is configured to transmit the predetermined number of pulses to the tissue sample over the predetermined period of time.

11. The system of claim 1, wherein the processing device is further configured to use the one or more optical signals and the changes in the birefringence of the tissue sample to predict a permanence of the non-thermal lesion formation in the tissue sample after delivery of the pulsed electrical signals to the tissue sample.

12. The system of claim 1, wherein the processing device is further configured to detect a loss in anisotropy of the tissue sample after delivery of the pulsed electrical signals to the tissue sample by analyzing the one or more optical signals.

13. The system of claim 1, wherein the processing device is configured to detect the changes in the birefringence of the tissue sample after protein denaturation in the tissue sample resulting from delivery of the pulsed electrical signals to the tissue sample.

14. A method for performing ablation in a patient, the method comprising:
    inserting a catheter into vasculature of the patient;
    moving a distal end of the catheter to an ablation site in the vasculature of the patient, the distal end comprising a plurality of electrodes;
    establishing tissue contact with the plurality of electrodes through optical means using light delivered to the ablation site through the distal end of the catheter;
    delivering energy from the distal end of the catheter into tissue at the ablation site from an energy source coupled to the catheter, the energy causing electroporation of the tissue;
    after a predetermined period of time, optically interrogating the tissue at the ablation site to determine changes in polarization or phase retardation of light delivered to the tissue at the ablation site through the catheter, the predetermined period of time comprising a length of time needed for a non-thermal lesion to begin forming in the tissue, the non-thermal lesion resulting from the electroporation of the tissue; and removing the catheter from the vasculature.

15. The method of claim 14, wherein the energy comprises a pulse train, the energy source comprises a pulse field ablation energy source, and the pulse train comprises pulsed electrical signals that are monophasic or biphasic.

16. The method of claim 15, wherein the changes in polarization or phase retardation of the light are in response to the pulsed electrical signals delivered to the tissue.

17. The method of claim 16, wherein characteristics of the pulsed electrical signals are selected by a user of the catheter, wherein the characteristics comprise a frequency, amplitude, and duration of the pulsed electrical signals.

18. The method of claim 14, wherein the energy comprises radiofrequency (RF), and the energy source comprises an RF energy source.

19. The method of claim 14, wherein the catheter comprises a shaft with a multimode-transmission media disposed in the shaft, wherein the multimode-transmission media is used to enable a use of tissue spectrometry to determine a depth of anatomical structures in the patient.

20. A catheter for ablating tissue in a cardiac wall, the catheter comprising:
a proximal end;
a distal end;
a plurality of electrodes disposed on the distal end at a distance from each other; and
at least one optical port positioned on the distal end at a location relative to the plurality of electrodes,
wherein the catheter is configured to be placed in an outer sheath such that the distal end is in a straight configuration compatible with vascular delivery, the distal end assuming a circular shape when pushed through the outer sheath,
wherein the plurality of electrodes are connected by wire to an external electrical energy generating device via an electrical connector on the proximal end of the catheter,
wherein the plurality of electrodes are configured to deliver electrical energy to a cardiac wall when energized by the external electrical energy generating device, the electrical energy causing electroporation of tissue in the cardiac wall,
wherein the at least one optical port comprises optical components connected by an optical fiber to an external optical energy generating device via an optical connector on the proximal end of the catheter, wherein the optical components are configured to:
project optical energy into the cardiac wall when energized by the external optical energy generating device after a predetermined period of time comprising a length of time needed for a non-thermal lesion to begin forming in the tissue, the non-thermal lesion resulting from the electroporation of the tissue,
receive reflected optical energy back from the cardiac wall, and
transfer the reflected optical energy through the optical fiber and the optical connector to an external optical sensing device, the external optical sensing device being configured to determine changes in polarization or phase retardation of the reflected optical energy resulting from the electroporation of tissue in the cardiac wall.

21. The catheter of claim 20, wherein the circular shape of the distal end is configured to contact the cardiac wall in a plane parallel to the cardiac wall.

22. The catheter of claim 20, wherein the location of the at least one optical port is chosen for optimal observation of optical parameter changes caused by tissue ablation by energization of the plurality of electrodes.

23. The catheter of claim 20, wherein the electrical energy delivered by the external electrical energy generating device comprises pulsed electrical signals.

24. The catheter of claim 23, wherein the pulsed electrical signals are monophasic or biphasic.

25. The catheter of claim 20, wherein the electrical energy delivered by the external electrical energy generating device comprises radiofrequency (RF) energy.

* * * * *